United States Patent [19]

Yokoyama et al.

[11] Patent Number: 4,734,418
[45] Date of Patent: Mar. 29, 1988

[54] QUINAZOLINE COMPOUNDS AND ANTIHYPERTENSIVES

[75] Inventors: Keiichi Yokoyama, Iwakuni; Koji Kato, Kuga; Takumi Kitahara, Ohtake; Hiroyasu Ohno, Iwakuni; Takashi Nishina; Mikio Kumakura, both of Mobara; Akira Awaya; Takuo Nakano, both of Yokohama; Kazuyuki Watanabe; Sakae Saruta, both of Mobara, all of Japan

[73] Assignee: Mitsui Petrochemical Industries, Ltd., Tokyo, Japan

[21] Appl. No.: 805,905

[22] Filed: Dec. 6, 1985

[30] Foreign Application Priority Data

Dec. 14, 1984 [JP] Japan ............... 59-263015
Sep. 5, 1985 [JP] Japan ............... 60-194968
Sep. 18, 1985 [JP] Japan ............... 60-204463

[51] Int. Cl.$^4$ ............... A61K 31/55; A61K 31/505; C07D 403/14; C07D 401/04
[52] U.S. Cl. ............... 514/258; 514/215; 514/218; 540/521; 540/575; 544/279; 544/280; 544/284
[58] Field of Search ............... 544/284, 279, 280; 514/215, 218, 260, 258; 540/575, 521

[56] References Cited

U.S. PATENT DOCUMENTS 4,351,832  9/1982  Rakhit et al. ............... 544/284
4,435,401  3/1984  Campbell et al. ............... 544/284
4,483,857 11/1984  Campbell et al. ............... 514/222
4,483,859 11/1984  Campbell et al. ............... 514/222

Primary Examiner—Donald G. Daus
Assistant Examiner—Barbara Cassatt
Attorney, Agent, or Firm—Cushman, Darby & Cushman

[57] ABSTRACT

Disclosed herein is an antihypertensive preparation containing, as an active component, a novel quinazoline derivative represented by the following general formula or a salt thereof:

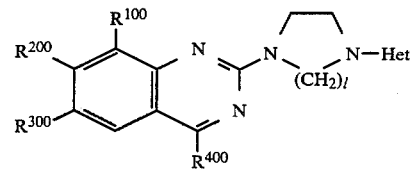

wherein $R^{100}$ means a hydrogen atom or methoxy group, $R^{200}$ and $R^{300}$ denote individually a hydrogen atom or lower alkoxy group, $R^{400}$ is a hydrogen atom or amino group, l stands for 2 or 3, and Het is a specific hetero ring group.

18 Claims, No Drawings

QUINAZOLINE COMPOUNDS AND ANTIHYPERTENSIVES

BACKGROUND OF THE INVENTION (1) Field of the Invention

This invention relates to novel quinazoline derivatives useful for the treatment of hypertension.

(2) Description of the Prior Art

Numerous quinazoline derivatives have been known to date, including especially piperazinoquinazolines such as various acid amide compounds, e.g., prazosin (Japanese Patent Publication No. 22135/1970; U.S. Pat. No. 3,511,836), terazosin (Japanese Patent Laid-Open No. 27588/1979; U.S. Pat. Nos. 4,026,894 and 4,112,097) and those disclosed in Japanese Patent Laid-Open No 116052/1982 as well as piperazinoquinazoline of the pyrimidine structure such as those disclosed in Japanese Patent Laid-Open No. 181068/1982 (U.S. Pat. Nos. 4,435,301, 4,483,857 and 4,483,859). These conventional quinazoline derivatives have been subjected to further investigations, whereby some of the quinazoline derivatives have already been clinically applied as antihypertensive agents. They are classified as α-adrenergic antihypertensive agents. Although they have excellent clinical effects, some drawbacks have been observed that they lack long-acting properties and develop orthostatic hypotension as an undesirable side effect.

SUMMARY OF THE INVENTION

An object of this invention is to provide novel quinazoline derivatives and their salts.

Another object of this invention is to provide antihypertensive preparations which contain these compounds as active components.

A further object of this invention is to provide a process for the preparation of these compounds.

The present inventors have found through treating hypertension in mammals that compounds represented by the below-described general formula [I] have extremely strong and long-acting antihypertensive effects and can reduce or substantially avoid the development of the above-mentioned orthostatic hypotension compared with the conventional compounds, leading to completion of this invention.

This invention provides, as an invention on materials, a quinazoline compound represented by the following formula [I] or a pharmacologically acceptable salt thereof:

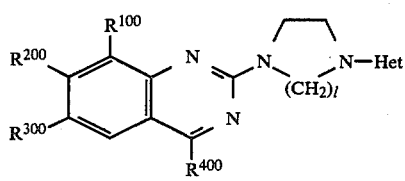

wherein $R^{100}$ means a hydrogen atom or methoxy group, $R^{200}$ and $R^{300}$ denote individually a hydrogen atom or lower alkoxy group, $R^{400}$ is a hydrogen atom or amino group, l stands for 2 or 3, and Het is represented by any one of the following formulae [II] through [XIX]:

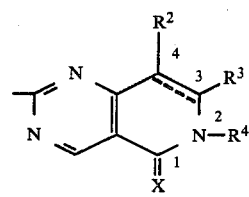

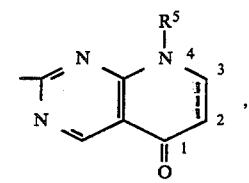

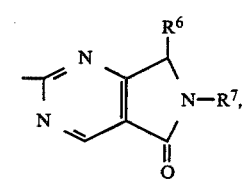

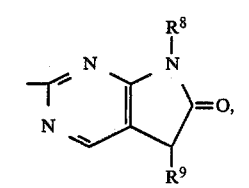

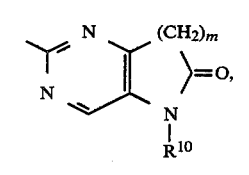

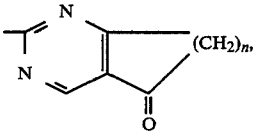

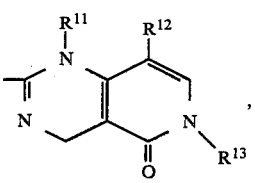

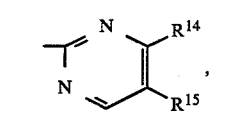

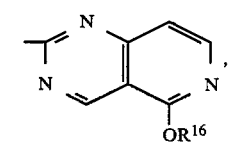

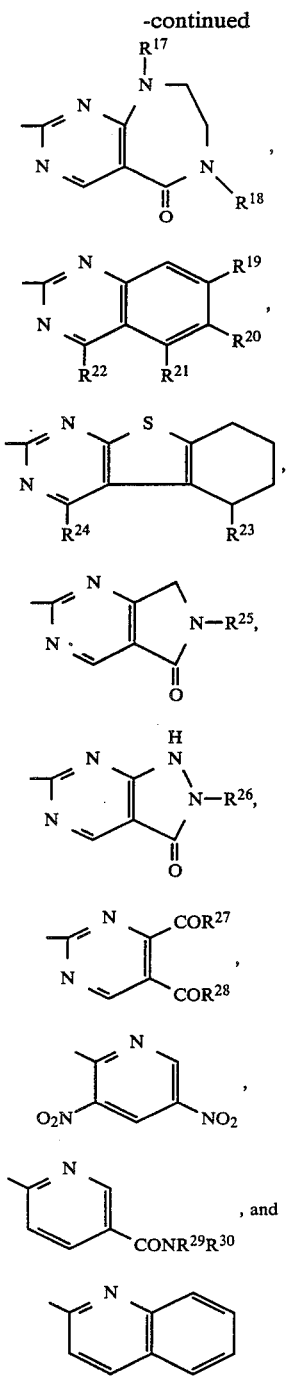

wherein, in the formula [II], either single or double bond is formed between the 3- and 4-positions, $R^2$ means a hydrogen atom or a lower alkyl, aralkyl in which alkyl is $C_1$–$C_4$ and aryl is $C_6$–$C_8$, cyano or formyl group, $R^3$ denotes a hydrogen atom or a lower alkoxycarbonyl or phenyl group, $R^4$ is a hydrogen atom or a lower alkyl, lower cycloalkyl, hydroxy-substituted lower alkyl, lower alkoxy-substituted lower alkyl, phenyl or aralkyl in which alkyl is $C_1$–$C_4$ and aryl is $C_6$–$C_8$, and X stands for an oxygen or sulfur atom, in the formula [III], either single or double bond is formed between the 2- and 3-positions, and $R^5$ means a hydrogen atom or a lower alkyl group, in the formula [IV], $R^6$ and $R^7$ mean individually a hydrogen atom or a lower alkyl group, in the formula [V], $R^8$ and $R^9$ mean individually a hydrogen atom or a lower alkyl group, in the formula [VI], m stands for 2 or 3, and $R^{10}$ means a hydrogen atom or a lower alkyl group, in the formula [VII], n stands for an integer of from 2 to 4, in the formula [VIII], $R^{11}$, $R^{12}$ and $R^{13}$ mean individually a hydrogen atom or a lower alkyl group, in the formula [IX], $R^{14}$ means a hydrogen atom or a hydroxyl, lower alkyl, —$NR^{31}R^{32}$ in which $R^{31}$ is a hydrogen atom or a lower alkyl group and $R^{32}$ is a hydrogen atom or a lower alkyl or lower alkanoyl group, lower alkylthio or lower alkoxy group, $R^{15}$ denotes a lower alkanoyl, lower alkoxycarbonyl, —$CONR^{33}R^{34}$ in which $R^{33}$ is a hydrogen atom or a lower alkyl group, $R^{34}$ is a hydrogen atom or a lower alkyl, phenyl, aralkyl in which alkyl is $C_1$–$C_4$ and aryl is $C_6$–$C_8$, halogen-substituted lower alkyl or $C_4$–$C_7$ cycloalkyl group or $R^{33}$ and $R^{34}$ couples together to form a methylene moiety which in turn forms a ring having 4 to 5 carbon atoms together with the associated nitrogen atom, —$CONHNR^{35}R^{36}$ in which $R^{35}$ and $R^{36}$ are individually a lower alkyl group, —$CH_2CONHR^{37}$ in which $R^{37}$ is a lower alkyl, or cyano group, in the formula [X], $R^{16}$ means a lower alkyl group, in the formula [XI], $R^{17}$ and $R^{18}$ mean individually a hydrogen atom or a lower alkyl group, in the formula [XII], $R^{19}$ through $R^{21}$ means a hydrogen atom or a lower alkoxy group, and $R^{22}$ denotes —$NR^{38}R^{39}$ in which $R^{38}$ and $R^{39}$ are individually a hydrogen atom or a lower alkyl group, or a hydrogen atom, in the formula [XIII], $R^{23}$ means a hydrogen atom or a lower alkyl group, and $R^{24}$ denotes a hydrogen atom or a lower alkylthio group, in the formula [XIV], $R^{25}$ means a $C_5$–$C_8$ alkyl, $C_4$–$C_7$ cycloalkyl, hydroxy-substituted lower alkyl group, lower alkoxy-substituted lower alkyl, di(-lower alkylamino)-substituted lower alkyl or aralkyl in which alkyl is $C_1$–$C_4$ and aryl is $C_6$–$C_8$, in the formula [XV], $R^{26}$ means a lower alkyl group, in the formula [XVI], $R^{27}$ and $R^{28}$ are either same or different and mean individually a lower alkoxy, hydroxyl or lower alkylamino group, or $R^{27}$ and $R^{28}$ couples together to form a lower alkyl-substituted imino group, and in the formula [XVIII], $R^{29}$ and $R^{30}$ are either same or different and mean individually a lower alkyl group; and as an invention on utility, an antihypertensive preparation containing the quinazoline derivative or its pharmacologically acceptable salt as an active component.

Particularly preferred compounds include those having the general formula [I] in which $R^{200}$ and $R^{300}$ are individually a methoxy group, $R^{400}$ denotes an amino group and Het is represented by any one of the formulae [II] through [XIII]; those having the general formula [I] in which $R^{100}$ denotes a hydrogen atom, $R^{200}$ and $R^{300}$ denote individually a methoxy group, $R^{400}$ is an amino group, l stands for 2 and Het is represented by any one of the formulae [XIV] through [XIX]; and those having the general formula [I] in which $R^{100}$ and $R^{400}$ mean individually a hydrogen atom, l stands for 2 and Het is represented by the formula [II] wherein a double bond is formed between the 3- and 4-positions, $R^2$ and $R^3$ mean individually a hydrogen atom, X denotes an oxygen atom and $R^4$ is a lower alkyl group.

DETAILED DESCRIPTION OF THE PREFERRED EMBODIMENTS

[Materials of the Invention]

Although materials of the present invention are the compounds represented by the general formula [I], the compounds represented by the following formula [I'] will next be mentioned as one of preferred embodiments of this invention:

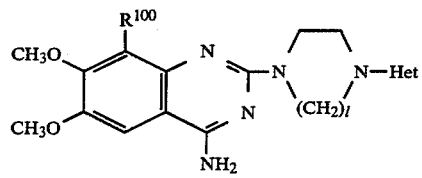

wherein $R^{100}$ means a hydrogen atom or methoxy group, the former being preferred, and l stands for 2 or 3 with 2 being preferred.

In the above formula [I'], Het is represented by any one of the formulae [II] to [XIII].

In the formula [II], as the lower alkyl group represented by $R^2$, may be mentioned by way of example methyl group, ethyl group, propyl group, isopropyl group, butyl group, isobutyl group, sec-butyl group, tert-butyl group or the like with methyl group being preferred. As an exemplary aralkyl group, may be mentioned benzyl group, diphenyl methyl group or the like with benzyl group being preferred. $R^3$ is a hydrogen atom or a lower alkoxycarbonyl or phenyl group with a hydrogen atom being preferred. Illustrative of the lower alkoxycarbonyl group may be methoxycarbonyl group, ethoxycarbonyl group, propoxycarbonyl group and the like. Among these groups, ethoxycarbonyl group is preferred. As the lower alkyl group represented by $R^4$, the lower alkyl group represented above by $R^2$ may be mentioned. The lower cycloalkyl group contains 3-5 carbon atoms with cyclopropyl group being preferred. As an exemplary hydroxy-substituted lower alkyl group, may be mentioned a methylol group, ethylol group or the like with an ethylol group being preferred. Illustrative of the lower alkoxy-substituted lower alkyl group may be a methoxymethyl group, ethoxymethyl group, methoxyethyl group, ethoxyethyl group and so on. Of these, a methoxyethyl group is preferred. As the aralkyl group, may be mentioned that represented above by $R^2$.

In the formula [III], as the lower alkyl group represented by $R^5$, may be mentioned the lower alkyl group represented above by $R^2$ with an ethyl group being preferred.

In the formula [IV], as the lower alkyl group represented by each of $R^6$ and $R^7$, may be mentioned the lower alkyl group represented above by $R^2$. A hydrogen atom is preferred as $R^6$.

As the lower alkyl groups represented respectively by $R^8$ through $R^{14}$ in the formulae [V], [VI], [VIII] and [IX], may be mentioned those represented above by $R^2$. In the formula [V], a lower alkyl group is preferred as $R^8$ while a hydrogen atom is preferred as $R^9$. In the formula [VI], m is preferably 3 and $R^{10}$ denotes preferably a lower alkyl group. In the formula [VII], n stands preferably for 3. In the formula [VIII], $R^{11}$ and $R^{12}$ mean individually and preferably a hydrogen atom and $R^{13}$ is preferably a lower alkyl group.

In $-NR^{31}R^{32}$ as $R^{14}$ in the formula [IX], as exemplary lower alkyl groups represented respectively by $R^{31}$, $R^{32}$, may be mentioned those represented above by $R^2$. Illustrative of the lower acyl group represented by $R^{32}$ may be an acetyl group, propionyl group, butyryl group and the like. Of these, an acetyl group is preferred. As exemplary lower alkylthio groups represented by $R^{14}$, may be mentioned a methylthio group, ethylthio group and the like and the former group being preferred. As the lower alkoxy group, may for example be mentioned a methoxy group, ethoxy group, propoxy group, isopropoxy group, butoxy group or the like with a methoxy group being preferred. As the lower acyl group represented by $R^{15}$, may be mentioned that represented above by $R^{32}$ with an acetyl group being preferred. Illustrative of the lower alkoxycarbonyl group may be a methoxycarbonyl group, ethoxycarbonyl group, propoxycarbonyl group, isopropoxycarbonyl group, butoxycarbonyl group and the like. As the lower alkyl groups represented respectively by $R^{33}$ and $R^{34}$, may be mentioned those represented above by $R^2$. $R^{33}$ and $R^{34}$ may be either same or different. Illustrative of the aralkyl represented by $R^{34}$ may be those represented above by $R^2$. A benzyl group is preferred as the aralkyl group. As exemplary halogen-substituted lower alkyl groups, may be mentioned a trifluoromethyl group, 2-fluoroethyl group, 2,2,2-trifluoroethyl group, 2,2,3,3,3-pentafluoropropyl group, 2-chloroethyl group, and so on. Of these, a 2,2,2-trifluoroethyl group is preferred. As the cycloalkyl group, may for example be mentioned a cyclobutyl group, cyclopentyl group, cyclohexyl group, cycloheptyl group or the like with a cyclohexyl group being preferred. As the lower alkyl groups represented respectively by $R^{35}$ to $R^{37}$ in $-CONHNR^{35}R^{36}$ and $-CH_2CONHR^{37}$, may be mentioned those represented above by $R^2$.

In the formulae [X] through [XIII], illustrative of the lower alkyl groups represented by $R^{16}$ to $R^{21}$, $R^{23}$, $R^{38}$ and $R^{39}$ may be those represented above by $R^2$. As the alkylthio group represented by $R^{24}$, may be mentioned that represented above by $R^{14}$. In the formula [XI], each of $R^{17}$ and $R^{18}$ is preferably a lower alkyl group. As $R^{23}$ in the formula [XIII], a lower alkyl group is preferred. As $R^{24}$, a lower alkythio group is preferred.

Furthermore, the compounds represented by the following formula [I''] may also be mentioned as another preferred embodiment of this invention.

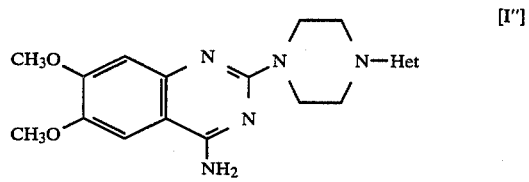

In the above formula [I''], Het is represented by the formula [XIV] or [XIX].

In the formula [XIV], the alkyl group represented by $R^{25}$ contains 5 or more carbon atoms. As such alkyl groups, may for example be mentioned amyl groups such as n-amyl group, hexyl groups such as n-hexyl groups, heptyl groups such as n-heptyl group, octyl groups such as n-octyl groups, etc. Among these alkyl groups, n-heptyl group is particularly preferred. As exemplary cycloalkyl groups represented by $R^{25}$, may be mentioned those containing 4 to 7 carbon atoms with cyclohexyl group containing 6 carbon atoms being particularly preferred. As illustrative hydroxy-substituted lower alkyl groups represented by $R^{25}$, may be mentioned methylol group and ethylol groups. Of these, the latter group is preferred. As exemplary lower alkoxy-substituted lower alkyl groups represented by $R^{25}$, may be mentioned those containing 2–8 carbon atoms, for example, methoxymethyl group, ethoxy-methyl group, methoxyethyl group, ethoxyethyl group and so on. Of these, methoxyethyl group is preferred. As the lower-(alkyl)amino-substituted lower alkyl group represented by $R^{25}$, may for example be mentioned 2-dimethylaminoethyl group, 2-diethylaminoethyl group or the like. Of these, the former is preferred. As illustrative aralkyl groups represented by $R^{25}$, may be mentioned benzyl group, diphenylmethyl group, triphenyl methyl group, 2-phenylethyl group and so on. Of these, benzyl group and 2-phenylethyl group are preferred. In the formula [XV], illustrative of the lower alkyl group represented by $R^{26}$ may be methyl group, ethyl group, propyl group, isopropyl group, n-butyl group, isobutyl group, sec-butyl group and tert-butyl group with methyl group being preferred.

In the formula [XVI], as exemplary lower alkoxy groups represented by $R^{27}$ or $R^{28}$ may be mentioned methoxy group, ethoxy group, propoxy group, isopropoxy group, butoxy group, etc. Among these groups, ethoxy groups is especially preferred. In addition, illustrative of the lower(alkyl)amino group represented by $R^{27}$ or $R^{28}$ may be methylamino group, ethylamino group, n-propylamino group, isopropylamino group, n-butylamino group, isobutylamino group, sec-butylamino group, tert-butylamino group and so on. Among these groups, ethylamino group is particularly preferred. As the lower alkyl group in the lower(alkyl)-substituted imino group represented by $R^{27}$ or $R^{28}$, any one of the lower alkyl groups referred to above by way of example for $R^{26}$ may be mentioned with ethyl group being preferred.

In the formula [XVIII], the lower alkyl groups mentioned above for $R^{26}$ may be mentioned as exemplary lower alkyl groups represented by $R^{29}$ and $R^{30}$.

As a further preferred embodiment of this invention, may be mentioned the compounds represented by the following formula [I''']:

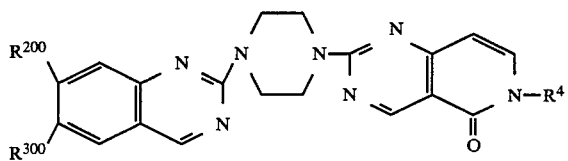

In the above formula [I'''], $R^{200}$ and $R^{300}$ individually means a hydrogen atom or lower alkoxy group and $R^4$ denotes a lower alkyl group. As exemplary lower alkoxy groups represented by $R^{200}$ or $R^{300}$, may be mentioned methoxy group, ethoxy group, propoxy group, isopropoxy group, butoxy group and the like with methoxy group being preferred. Where $R^{200}$ stands for a hydrogen atom, it is preferred that $R^{300}$ stands also for a hydrogen atom. Similarly, where $R^{200}$ stands for a lower alkoxy group, it is preferred that $R^{300}$ is also a lower alkoxy group. In the latter case, $R^{200}$ and $R^{300}$ may be different from each other. Furthermore, as exemplary lower alkyl groups represented by $R^4$, methyl group, ethyl group, propyl group, isopropyl group, n-butyl group, isobutyl group, sec-butyl group and tert-butyl group may be mentioned by way of example. Among these groups, ethyl group is preferred.

Certain specific exemplary compounds of this invention will be described in Examples, which will be given later in this specification. As pharmacologically acceptable salts of the compound [I] of this invention, may be mentioned, by way of example, those obtained in combination with acids capable of forming pharmacologically-acceptable nontoxic acid addition salts which may optionally contain anions, such as its hydrochloride, hydrobromide, sulfate, bisulfate, phosphate, acid phosphate, acetate, maleate, fumarate, succinate, lactate, tartrate, benzoate, citrate, gluconate, saccharate, methanesulfonate and p-toluenesulfonate. Hydrates of such salts are also embraced in the compounds of this invention.

[Preparation process]

The compounds of this invention may be prepared in a process known per se in the art, for example, in accordance with the process described in Japanese Patent Laid-Open No. 181068/1982. Namely, an exemplary preparation process may be indicated by the following equation.

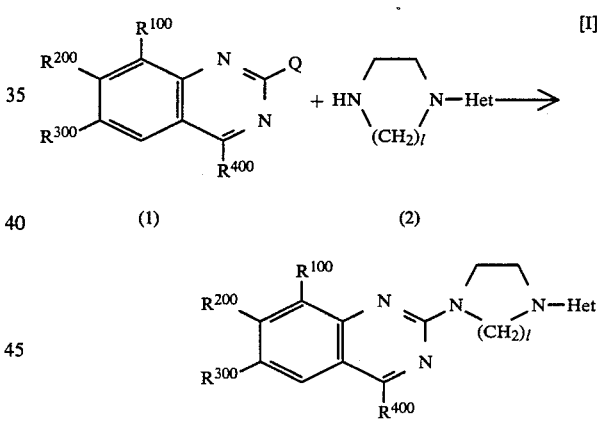

wherein Q means a readily-removable group such as a halogen atom, $C_{1-4}$ alkoxy group or $C_{1-4}$ alkylthio group with Cl being preferred.

The compound (1) employed in the above reaction is a known material, while as the compound (2), any one of compounds synthesized respectively in the below-given Referential Examples may be used. Compounds which will not be found in the Referential Examples but fall within the definition for the compound (2) may also be synthesized following the Referential Examples and may also be used.

The reaction may be carried out by reacting the compounds (1) and (2), for example, in a suitable solvent such as isoamyl alcohol or n-butanol, under reflux, for example, at 100° to 150° C. and for about 1 to 6 hours. The temperature and time and type of the solvent may be changed suitably in accordance with the types of the compounds (1) and (2). In the above reaction, the compound [I] can usually be obtained as a free base by adding a tertiary amine such as triethylamine or the like to the reaction system. Alternatively, the above reaction can directly provide the hydrochloride of the compound [I] unless such a tertiary amine is employed.

The compound [I] may also be synthetically prepared by the following reaction:

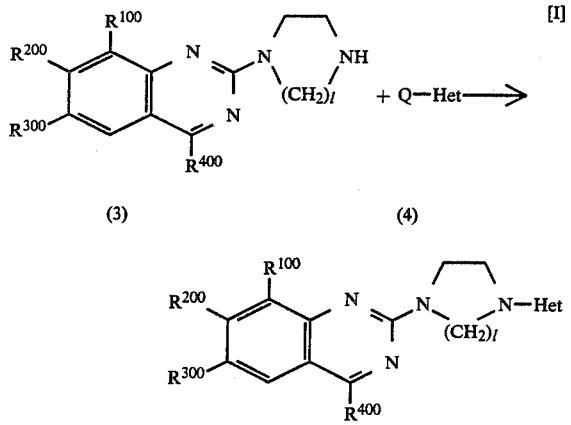

wherein Q is as defined above.

The thus-prepared compound [I] may be isolated and purified by a usual method. Furthermore, its acid addition salts led by its hydrochloride may also be obtained by a usual method, for example, by reacting the compound [I] with an acid in an inert organic solvent, isolating the resulting precipitate, and if necessary purifying same.

[Invention on Drug]

As already described above, the compound [I] of this invention has a strong antihypertensive effect. It is also expected to show some effects for the improvement of heart failure. The compound of the formula [I] is generally used in the form of pharmaceutical preparations and administered through various routes such as oral, subcutaneous, intramuscular, intravenous, endonasal, skin-penetrative and rectal routes.

The present invention includes pharmaceutical preparations each of which is composed of a pharmaceutically-acceptable carrier and as an active component, the compound of the general formula [I] or its acid addition salt. When producing preparations of this invention, they may be formed into tablets, capsules, powders, granules, troches, sansi (synchyses), cachets, elixirs, emulsions, solutions, syrups, suspensions, aerosols, ointments, formed poultices, tapes, soft and hard gelatin capsules, suppositories, sterile parenteral solutions, packed sterile powders, etc. Examples of the pharmaceutically-acceptable carrier include lactose, glucose, sucrose, sorbitol, mannitol, corn starch, crystalline cellulose, gum arabic, calcium phosphate, alginate, calcium silicate, microcrystalline cellulose, polyvinyl pyrrolidone, tragacanth gum, gelatin, syrup, methylcellulose, carboxymethylcellulose, methyl hydroxybenzoate, propyl hydroxybenzoate, talc, magnesium stearate, inert polymers, water, mineral oil, etc.

Both solid and liquid preparations may contain one or more of the above-mentioned fillers, binders, lubricants, wetting agents, disintegrators, emulsifying and suspending agents, preservatives, sweetening agents and/or aromatics. The preparations may each be formulated in such a way that after administration to patients, its active component is released in a rapid, long-acting or sustained fashion.

For oral administration, the compound of the formula [I] is mixed with a carrier and diluent and is then formed into tablets, capsules or the like. For parenteral administration, the active component is dissolved in a 10% aqueous solution of glucose, isotonic saline, sterilized water or an analogous liquid and is then sealed in vials or ampuls for its administration into veins by drip infusion or injection or its intramuscular injection. Advantageously, a solubilizer, local anesthetic, preservative and/or buffer may also be incorporated in the medium. It is also feasible to lyophilize the preparation after its sealing in vials or ampuls. As other preparation forms for parenteral administration, may be mentioned those administrable percutaneously, such as ointments and cataplasms. For such parenteral administration, formed poultices and tapes are advantageous.

The preparation of this invention may contain an active component in an amount of 0.005-200 mg, more generally, 0.02-50 mg per unit dosage.

The compound of the general formula [I] is effective over a wide range of dosage. For example, its dosage per day may generally range from 0.0001 mg/Kg to 200 mg/Kg. The amount of the compound to be administered actually varies depending on the type of the compound and may be determined by physician depending on the age, weight and sensitivity of each patient, the seriousness in symptom of the patient, the administration route, etc. Therefore, the above dosage range shall not be interpreted as limiting the scope of this invention. The preparation of this invention may be administered 1-6 times a day with 1-4 times being usually suitable.

Although the compound of the formula [I] is by itself an effective antihypertensive agent, it may be administered, if necessary, in combination with one or more other antihypertensive agents and/or diuretics. Such additional drugs may include methyldopa, hydralazine, nifedipine, nicardipine, amyloride, propranolol, pindolol, timolol, reserpine, indapamide, hydrochlorothiazide, trichloromethiazide, indaclinone and their analogous drugs.

Physical properties and biological activities of certain compounds of this invention will hereinafter be described in the following Referential Examples, Examples and Tests. It should however be borne in mind that the present invention is not limited to the following Examples and Tests. The following Referential Examples relate to the preparation of intermediates for some compounds of the general formula [I], while the following Examples are concerned with the preparation of certain compounds of the general formula [I]. Tests will be described in the [Effects of the Invention].

REFERENTIAL EXAMPLE 1

Methyl 2-(4-benzylpiperazino)-4-methylpyrimidine-5-carboxylate

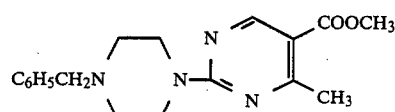

One hundred milliliters of a 1M solution of sodium hydroxide in methanol were added to a suspension (60 ml) of 26.8 g (0.1 mol) of 1-amidino-4-benzylpiperazine sulfate [which had been synthesized in accordance with the process disclosed in J. Am. Chem. Soc., 66, 263 (1944)] in methanol, followed by a dropwise addition of 15.8 g (0.1 mol) of methyl α-methoxymethyleneacetoacetate. After stirring the resultant mixture overnight at room temperature, the precipitated sodium sulfate was filtered off. After distilling off methanol, the residue was dissolved in 500 ml of ethyl acetate. The resultant solution was washed twice with 100 ml of water. The ethyl acetate layer was washed with saturated saline and then dried with anhydrous magnesium sulfate. Upon distilling off ethyl acetate, 28.7 g of the intended compound was obtained as an orange-colored oily substance (yield: 88%). When the oily substance was left over at room temperature subsequent to its distillation under a reduced pressure, it was crystallized.

Boiling point: 205°-208° C./1 mmHg.
Melting point: 38°-40° C.
Infrared absorption spectrum (neat, cm$^{-1}$): 1710, 1580, 1520.
$^1$H-NMR spectrum (CDCl$_3$ solution, δ ppm): 2.50 (4H, m), 2.63 (3H, s), 3.54 (2H, s), 3.83 (3H, s), 3.94 (4H, m), 7.32 (5H, s), 8.78 (1H, s).

The following compounds were synthesized in a similar manner.

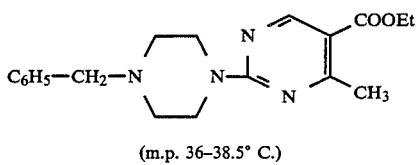

(m.p. 36-38.5° C.)

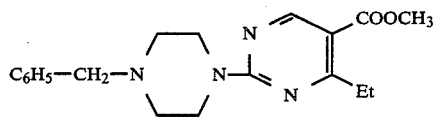

(Yellow oil. The raw material was synthesized by the process of Referential Example 2.)

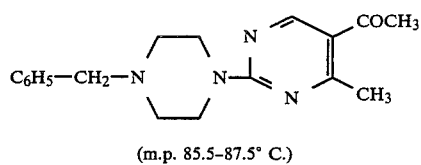

(m.p. 85.5-87.5° C.)

REFERENTIAL EXAMPLE 2

Methyl 2-methoxymethylene-3-oxo-n-valerate

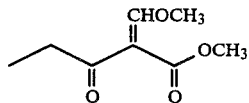

A mixture of 1.95 g of methyl 3-oxo-n-valerate [15 mmol; synthesized in accordance with the process disclosed in J. Am. Chem. Soc., 96, 1082 (1974)], 3.18 g (30 mmol) of methyl orthoformate and 4.59 g (45 mmol) of acetic anhydride was heated under reflux for 8 hours, and low b.p. fractions were then distilled off (bath temperature: 100° C.). The residue was distilled under reduced pressure to obtain 1.97 g of the intended compound as a yellowish oily substance (yield: 76%). This compound was used in the synthesis of the compound of Referential Example 1.

Boiling point: 86°-90° C./3 mmHg.
Infrared absorption spectrum (neat, cm$^{-1}$): 1710, 1625.
$^1$H-NMR spectrum (CDCl$_3$ solution, δ ppm): 1.07 and 1.08 (total 3H, t, J=7.0 HZ), 2.68 and 2.71 (total 2H, q, J=7.0 HZ), 3.74 and 3.81 (total 3H, s), 3.96 and 4.00 (total 3H, s), 7.51 and 7.56 (total 1H, s).

REFERENTIAL EXAMPLE 3

2-(4-Benzylpiperazino)-4-methylpyrimidine-5-carboxylic acid

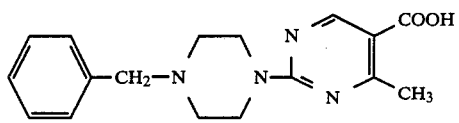

Added to a 1 l flask were 40 g (0.128 mol) of the ethyl 2-(4-benzylpiperazino)-4-methylpyrimidine-5-carboxylate, 11 g of KOH, 200 ml of H$_2$O and 500 ml of EtOH. The contents were stirred at 100° C. for 0.5 hr. Thereafter, the solvent was distilled off under reduced pressure. One liter of H$_2$O was then added to the residue and the resulting mixture was adjusted to pH 4 with conc. hydrochloric acid. The precipitated crystals were filtered off and the filtrate was dried under reduced pressure, thereby obtaining 36 g of the intended compound as a white solid substance (yield: 98%).

Melting point: 192° C.
Mass spectrum (m/z): 312 (molecular ion peak).
Infrared absorption spectrum (KBr tablet, cm$^{-1}$): 3424, 1700, 1652, 1576.
$^1$H-NMR spectrum (DMSO-d$_6$ solution, δ ppm): 2.56 (3H, s), 2.77 (4H, m), 3.87 (2H, s), 4.00 (4H, m), 7.36 (5H, s), 8.71 (1H, s).

REFERENTIAL EXAMPLE 4

2-(4-(Benzylpiperazino)-4-methyl-N-phenylpyrimidine-5-carboxylic acid amide

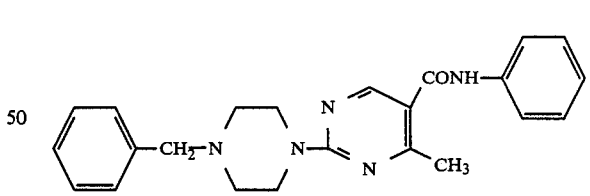

Added with ice cooling to a suspension (100 ml) of 16.1 g (60 mmol) of 1-amidino-4-benzylpiperazine sulfate in methanol was 100 ml of a methanol solution of 2.4 g (60 mmol) of sodium hydroxide, followed by a dropwise addition of 200 ml of a methanol solution of 14.0 g (60 mmol) of α-ethoxymethyleneacetoacetic anilide (Referential Example 6). After stirring the resultant mixture overnight at room temperature, the precipitated salt was filtered off. The salt was washed with methanol. The filtrate and washing were combined together. After distilling off methanol, the residue was recrystallized from chloroform-hexane to obtain 17.26 g of the intended product as colorless crystals (yield: 74%). This compound was used for the synthesis of the compounds described in Referential Examples 10 and 11.

Melting point: 176°–177° C.

Infrared absorption spectrum (KBr tablet, cm$^{-1}$): 3300, 1653, 1595.

$^1$H-NMR spectrum (CDCl$_3$ solution, δ ppm): 2.48 (4H, m), 2.53 (3H, s), 3.54 (2H, s), 3.89 (4H, m), 7.1–7.6 (5H, m), 7.32 (5H, s), 7.70 (1H, br), 8.39 (1H, s).

REFERENTIAL EXAMPLE 5

2-(4-Benzylpiperazino)-N-ethyl-4-methylpyrimidine-5-carboxylic acid amide

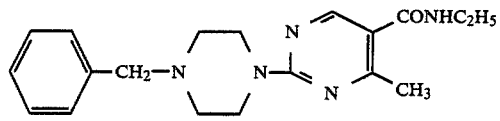

Placed in a 50 ml autoclave and reacted at 100° C. for 3.5 hours were 8.16 g (25 mmol) of the methyl 2-(4-benzylpiperazino)-4-methylpyrimidine-5-carboxylate obtained in Referential Example 1, 5.64 g (125 mmol) of ethyl amine and 1.24 g (5 mmol) of a 21.8 wt.% solution of sodium methoxide in methanol. The thus-obtained reaction mixture was poured in 150 ml of water, followed by extraction with ethyl acetate. The ethyl acetate layer was washed with saturated saline and then dried with magnesium sulfate. Thereafter, ethyl acetate was distilled off. The residue was recrystallized from ethyl acetate-hexane to obtain 7.71 g of the intended product as light yellowish crystals (yield: 91%).

Melting point: 110°–111° C.

Infrared absorption spectrum (KBr tablet, cm$^{-1}$): 3290, 1625, 1585.

$^1$H-NMR spectrum (CDCl$_3$ solution, δ ppm): 1.22 (3H, t, J=7.0 HZ), 2.49 (4H, m), 2.51 (3H, s), 3.42 (2H, m), 3.55 (2H, s), 3.88 (4H, m), 5.76 (1H, m), 7.32 (5H, s), 8.30 (1H, s).

The following compounds were also prepared in a similar manner.

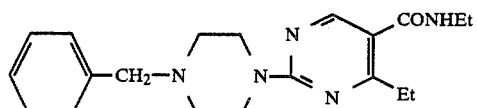

(m.p. 131–132° C.)

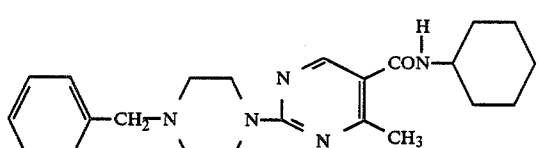

(m.p. 172–173° C.)

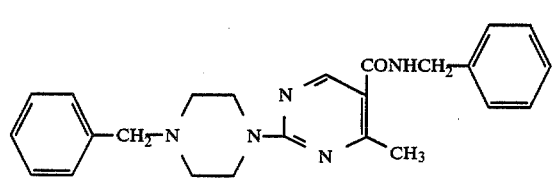

(m.p. 116–117° C.)

REFERENTIAL EXAMPLE 6

Synthesis of α-ethoxymethyleneacetoacetic anilide

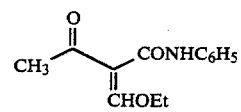

A mixture of 26.6 g (0.15 mol) of acetoacetic anilide, 44.5 g (0.3 mol) of ethyl orthoformate and 45.9 g (0.3 mol) of acetic anhydride was heated under reflux for 2 hours. After cooling the reaction mixture to room temperature, hexane was added. The precipitated crystals were collected by filtration. Upon their drying, 14.3 g of the intended product was obtained as light brownish needles (yield: 41%).

Melting point: 88°–89° C.

Infrared absorption spectrum (KBr tablet, cm$^{-1}$): 3160, 1660, 1585.

$^1$H-NMR spectrum (CDCl$_3$ solution, δ ppm): 1.46 (3H, t, J=7.0 HZ), 2.50 (3H, s), 4.37 (2H, q, J=7.0 HZ), 7.0–7.77 (6H), 8.46 (1H, s).

REFERENTIAL EXAMPLE 7

2-(4-Benzylpiperazino)-N-(2-hydroxyethyl)-4-methylpyrimidine-5-carboxylic acid amide Reacted at 170° C. for 1.5 hours were 0.34 g (1.0 mmol) of the ethyl 2-(4-benzylpiperazino)-4-methylpyrimidine-5-carboxylate and 1.22 g (20 mmol) of ethanol amine. After adding 50 ml of water, the resultant mixture was extracted with ethyl acetate. After washing the ethyl acetate layer with saturated saline, the ethyl acetate solution was dried with magnesium sulfate. Ethyl acetate was distilled off under reduced pressure and upon recrystallization of the residue from ethyl acetate-hexane, 0.25 g of the intended product was obtained as white crystals (yield: 72%).

Melting point: 123° C.

Infrared absorption spectrum (KBr tablet, cm$^{-1}$): 3280, 1630, 1594.

$^1$H-NMR spectrum (CDCl$_3$ solution, δ ppm): 2.48 (4H, m), 2.51 (3H, s), 2.46–2.62 (4H, m), 2.73–2.83 (6H, m), 6.39 (1H, brs), 7.32 (5H, s), 8.35 (1H, s).

REFERENTIAL EXAMPLE 8

2-(4-Benzylpiperazino)-4-methyl-N-[2-(2'-tetrahydropyranyloxy)ethyl]pyrimidine-5-carboxylic acid amide

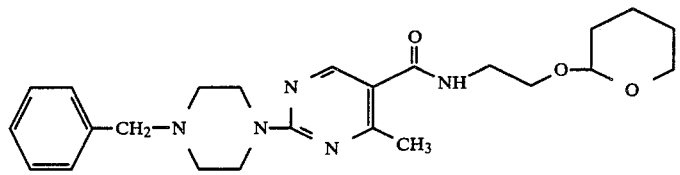

To an ethyl acetate solution (160 ml) of 2.76 g (7.75 mmol) of the 2-(4-benzylpiperazino)-N-(2-hydroxyethyl)-4-methylpyrimidine-5-carboxylic acid amide obtained in Referential Example 7, 6.52 g (77.5 mmol) of 2,3-dihydropyran and 1.77 g (9.30 mmol) of p-toluenesulfonic acid monohydrate were added. The resultant mixture was stirred at room temperature for 2 days. The thus-obtained reaction mixture was washed with a saturated solution of sodium bicarbonate and was then dried with magnesium sulfate. Thereafter, ethyl acetate was distilled off under reduced pressure. The residue was purified by silica gel chromatography (eluent: ethyl acetate), thereby obtaining 3.24 g of the intended product as light yellowish crystals (yield: 95%).

Melting point: 87°–88° C.

Infrared absorption spectrum (KBr tablet, cm$^{-1}$): 3280, 1622, 1588.

$^1$H-NMR spectrum (CDCl$_3$ solution, δ ppm): 1.3–2.0 (6H), 2.48 (4H, m), 2.52 (3H, s), 3.54 (2H, s), 3.5–3.9 (6H), 3.89 (4H, m), 4.56 (1H, m), 6.54 (1H, m), 7.31 (5H, s), 8.35 (1H, s).

REFERENTIAL EXAMPLE 9

2-(4-Benzylpiperazino)-4-methyl-pyrimidine-5-carboxylic acid amide

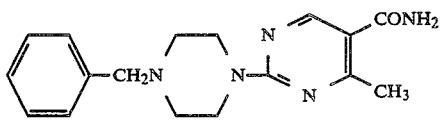

To 80 ml of pyridine containing, in a suspended state, 4.69 g (15 mmol) of the 2-(4-benzylpiperazino)-4-methylpyrimidine-5-carboxylic acid obtained in Referential Example 3, 4.45 g (37.5 mmol) of SOCl$_2$ was added. The resultant mixture was stirred at room temperature for 1 hour. Thereafter, 2.2 g (37.5 mmol) of 30% aqueous ammonia solution was added and the resultant mixture was stirred overnight at room temperature. After distilling off pyridine from the reaction mixture under reduced pressure, 200 ml of water was added, the pH of the resultant mixture was adjusted with K$_2$CO$_3$ to pH 8, and the thus-treated mixture was extracted with ethyl acetate. The ethyl acetate layer was washed with saturated saline. After drying the ethyl acetate solution with magnesium sulfate, ethyl acetate was distilled off under reduced pressure. The residue was recrystallized from chloroform-hexane to obtain 1.17 g of the intended product (yield: 25%).

Melting point: 195°–196° C.

Mass spectrum (m/z): 311 (molecular ion peak).

Infrared absorption spectrum (KBr tablet, cm$^{-1}$): 3497, 3367, 1611, 1577.

$^1$H-NMR spectrum (CDCl$_3$ solution, δ ppm): 2.48 (4H, m), 2.56 (3H, s), 3.54 (2H, s), 3.90 (4H, m), 7.31 (5H, s), 8.43 (1H, s).

The following compounds were also synthesized in a similar manner:

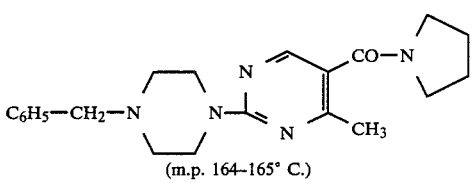
(m.p. 164–165° C.)

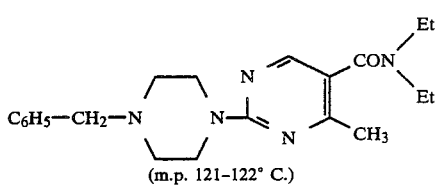
(m.p. 121–122° C.)

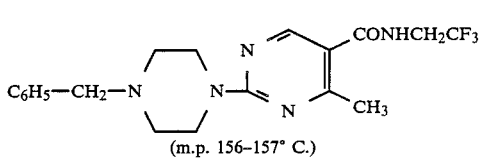
(m.p. 156–157° C.)

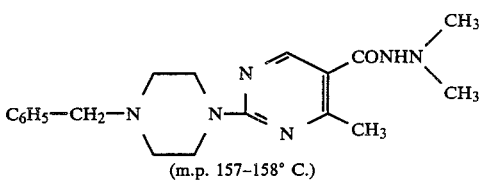
(m.p. 157–158° C.)

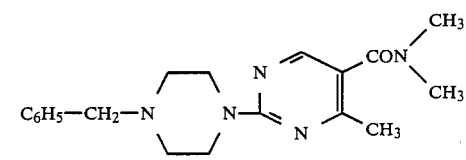

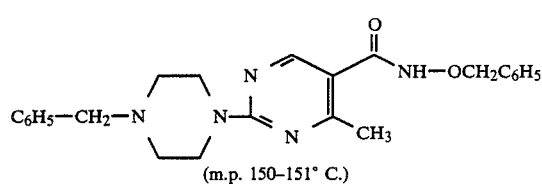
(m.p. 150–151° C.)

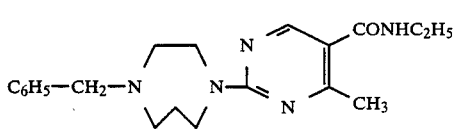

(The raw material was obtained in Referential Example 78.)

REFERENTIAL EXAMPLE 10

4-Methyl-2-piperazino-N-tetramethylenepyrimidine-5-carboxylic acid amide

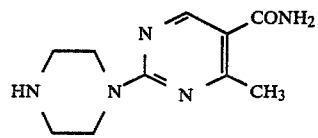

Placed in a two-necked 100 ml flask were 1.00 g of the 2-(4-benzylpiperazino)-4-methyl-N-tetramethylenepyrimidine-5-carboxylic acid amide obtained in Referential Example 9 and 0.1 g of 10% Pd-C, followed by hydrogen substitution under reduced pressure. Then, 20 ml of absolute ethanol and 20 ml of glacial acetic acid were added and the resultant mixture was stirred at 60°–65° C., under normal pressure for 1 hour. The reaction mixture was filtered and the catalyst was washed with ethanol. The filtrate was distilled to dryness under reduced pressure to obtain a viscous oily substance. The oily substance was purified by silica gel column chromatography (developed with EtOH), thereby obtaining 0.70 g of colorless crystals (yield: 93%).

Melting point: 228° C.
Infrared absorption spectrum (KBr tablet, cm$^{-1}$): 3420, 3300, 1625, 1585.
$^1$H-NMR spectrum (CDCl$_3$ solution, δ ppm): 1.82 (4H, br), 2.25 (3H, s), 2.73 (4H, m), 3.3 (4H, m), 3.70 (4H, m), 8.20 (1H, s).

The following compounds were also synthesized in a similar manner.

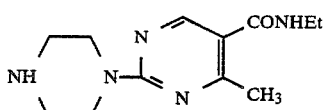

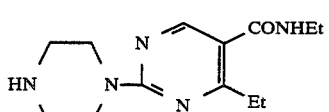

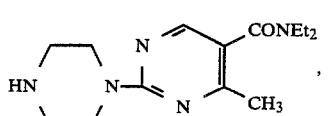

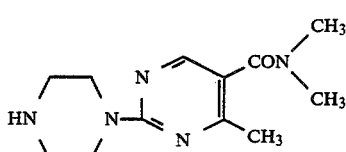

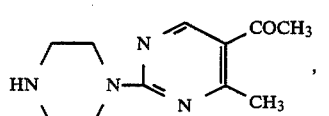

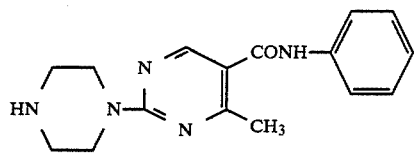

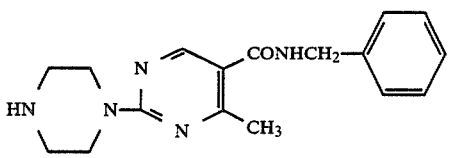

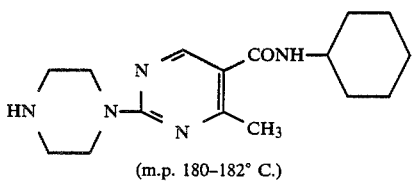

(m.p. 180–182° C.)

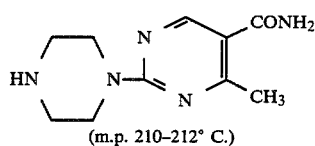

(m.p. 210–212° C.)

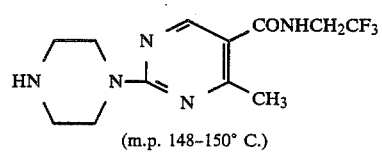

(m.p. 148–150° C.)

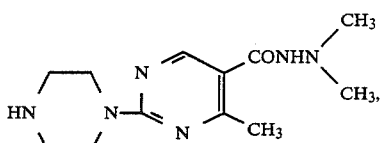

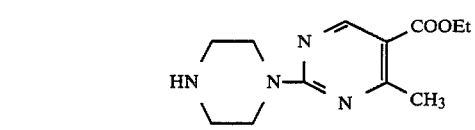

REFERENTIAL EXAMPLE 11

6-Ethyl-2-(4-benzylpiperazino)pyrido[4,3-d]pyrimidin-5(6H)-one

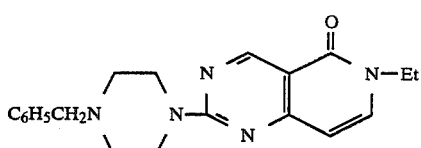

After washing 240 mg of sodium hydride (60% in oil, 6 mmol) with hexane, it was suspended in 3 ml of N,N-dimethylformamide (DMF). Thereafter, a DMF solution (10 ml) of 1.7 g (5 mmol) of 2-(4-benzylpiperazino)-N-ethyl-4-methylpyrimidine-5-carboxylic acid amide (Referential Example 5) was added and the reactants were reacted at 150° C. for 1.5 hours. After distilling off DMF under reduced pressure, 100 ml of water was added, followed by extraction with ethyl acetate. The ethyl acetate layer was washed with saturated saline and dried with magnesium sulfate, and ethyl acetate was distilled off under reduced pressure. The residue was recrystallized from ethyl acetate-hexane to obtain 1.5 g of the intended product as light yellowish crystals (yield: 87%).

Melting point: 116°–118° C.

Infrared absorption spectrum (KBr tablet, cm$^{-1}$): 1660, 1638.

$^1$H-NMR spectrum (CDCl$_3$ solution, δ ppm): 1.32 (3H, t, J=7 HZ), 2.50 (4H, t, J=6 HZ), 3.54 (2H, s), 3.76–4.08 (6H, m), 6.24 (1H, d, J=7 HZ), 7.23 (1H, d, J=7 HZ), 7.31 (5H, s), 9.20 (1H, s).

The following compounds were also synthesized in a similar manner.

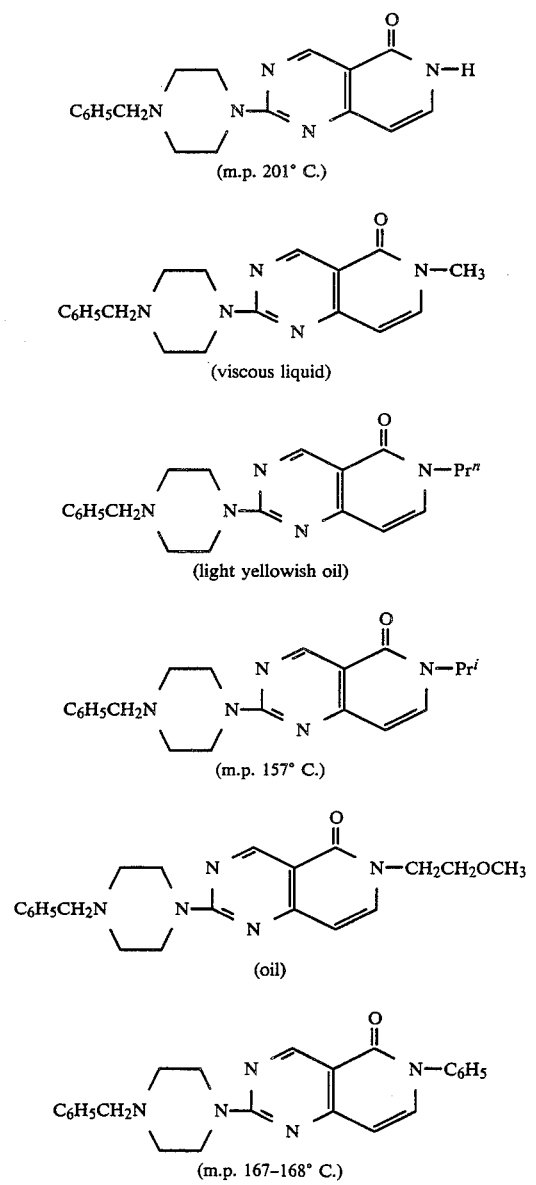

REFERENTIAL EXAMPLE 12

2-(4-Benzylpiperazino)-N-ethyl-N-ethyloxaloyl-4-methylpyrimidine-5-carboxylic acid amide Five milliliters of a tetrahydrofuran solution of 0.335 g (1 mmol) of the 2-(4-benzylpiperazino)-N-ethyl-4-methylpyrimidine-5-carboxylic acid amide obtained in Referential Example 5 were cooled in an ice bath, to which 0.048 g (60% in oil, 1.2 mmol) of sodium hydride was added. The resultant mixture was stirred for 10 minutes. Thereafter, 1 ml of a tetrahydrofuran solution of 0.15 g (1.1 mmol) of ethyloxalyl chloride was added dropwise. The thus-prepared mixture was stirred at room temperature for 1 hour and then at 70° C. for further 4 hours. The thus-obtained reaction mixture was poured in 50 g of ice water, followed by extraction with ethyl acetate. The organic layer was washed with saturated saline and then dried with sodium sulfate. Thereafter, the solvent was distilled off under reduced pressure. The residue was purified by silica gel column chromatography (eluent: ethyl acetate/hexane=3/2) to obtain 0.306 g of the intended product as a light blue oil (yield: 71%).

Infrared absorption spectrum (neat, cm$^{-1}$): 1740, 1712, 1672, 1590.

$^1$H-NMR spectrum (CDCl$_3$ solution, δ ppm): 1.18 (3H, t, J=7.2 Hz), 1.24 (3H, t, J=7.2 Hz), 2.47 (3H, s), 2.51 (4H, m), 3.58 (2H, s), 3.72-4.16 (8H, m), 7.34 (5H, s), 8.23 (1H, s).

REFERENTIAL EXAMPLE 13

Ethyl 2-(4-benzylpiperazino)-5,6-dihydro-6-ethyl-5-oxopyrido[4,3-d]pyrimidine-7-carboxylate

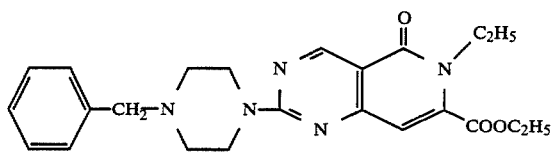

A mixture of 0.3 g (0.68 mmol) of the 2-(4-benzyl-piperazino)-N-ethyl-N-ethyloxaloyl-4-methylpyrimidine-5-carboxylic acid amide obtained in Referential Example 12, 0.027 g (60% in oil, 0.68 mmol) of sodium hydride and 5 ml of dimethylformamide was reacted at 120° C. for 2 hours. Fifty grams of ice water were added, followed be extraction with ethyl acetate. The oil layer was washed with saturated saline and was then dried with sodium sulfate. Ethyl acetate was distilled off under reduced pressure and the residue was purified by silica gel column chromatography (eluent: ethyl acetate), thereby obtaining 0.095 g of a light yellowish oil (yield: 33%). This compound was used for the preparation of the compound described in Referential Example 14.

Infrared absorption spectrum (neat, cm$^{-1}$): 1730, 1660, 1613, 1574.

$^1$H-NMR spectrum (CDCl$_3$ solution, δ ppm): 1.35 (3H, t, J=7 Hz), 1.42 (3H, t, J=7 Hz), 2.51 (4H, t, J=5.5 Hz), 3.55 (2H, s), 3.98 (4H, t, J=5.5 Hz), 4.26 (2H, q, J=7 Hz), 4.40 (2H, q, J=7 Hz), 6.75 (1H, s), 7.37 (5H, s), 9.22 (1H, s).

Mass spectrum: 421 (molecular ion peak).

REFERENTIAL EXAMPLE 14

5,6-Dihydro-6-ethyl-8-methyl-5-oxo-2-piperazinopyrido[4,3-d]pyrimidine-5(6H)-one

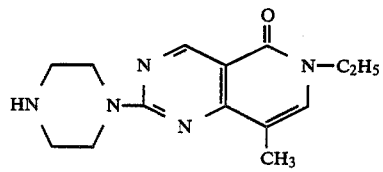

Added to 300 mg (0.83 mmol) of the 2-(4-benzyl-piperazino)-6-ethyl-8-methylpyrido[4,3-d]pyrimidine-5(6H)-one obtained in Referential Example 11 were 6 ml of ethanol, 2 ml of acetic acid and 30 mg of 10% Pd-C. The resultant mixture was stirred at 45° C. for 3.5 hours in a hydrogen atmosphere. The Pd-C was removed from the reaction mixture, followed by concentration under reduced pressure. The concentrate was added with 20 ml of water, to which potassium carbonate was added until no foams were developed. The resultant mixture was extracted three times with 50 ml of chloroform. The chloroform layer was dried with sodium sulfate and then concentrated under reduced pressure, thereby obtaining 200 mg of 6-ethyl-8-methyl-2-piperazinopyrido[4,3-d]pyrimidine-5(6H)-one as colorless crystals (yield: 88%).

Melting point: 170°-172° C.

Infrared absorption spectrum (KBr tablet, cm$^{-1}$): 1657, 1618, 1578.

$^1$H-NMR spectrum (CDCl$_3$ solution, δ ppm): 1.33 (3H, t, J=7.2 Hz), 1.66 (1H, s), 2.17 (3H, d, J=1.3 Hz), 2.94 (4H, m), 3.97 (6H, m), 7.10 (1H, q, J=1.3 Hz), 9.24 (1H, s).

The following compounds were also prepared in a similar manner.

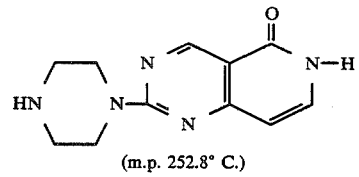

(m.p. 252.8° C.)

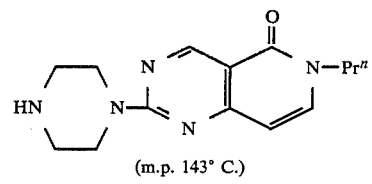

(m.p. 143° C.)

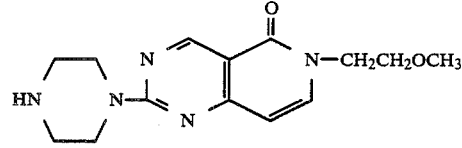

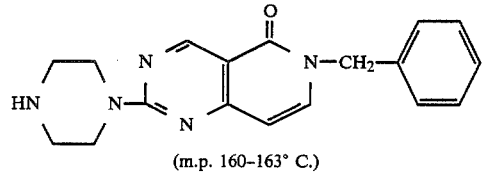

(m.p. 160-163° C.)

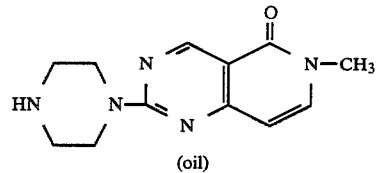

(oil)

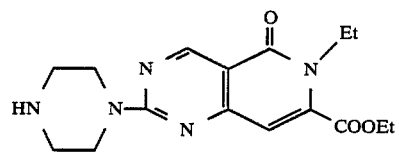

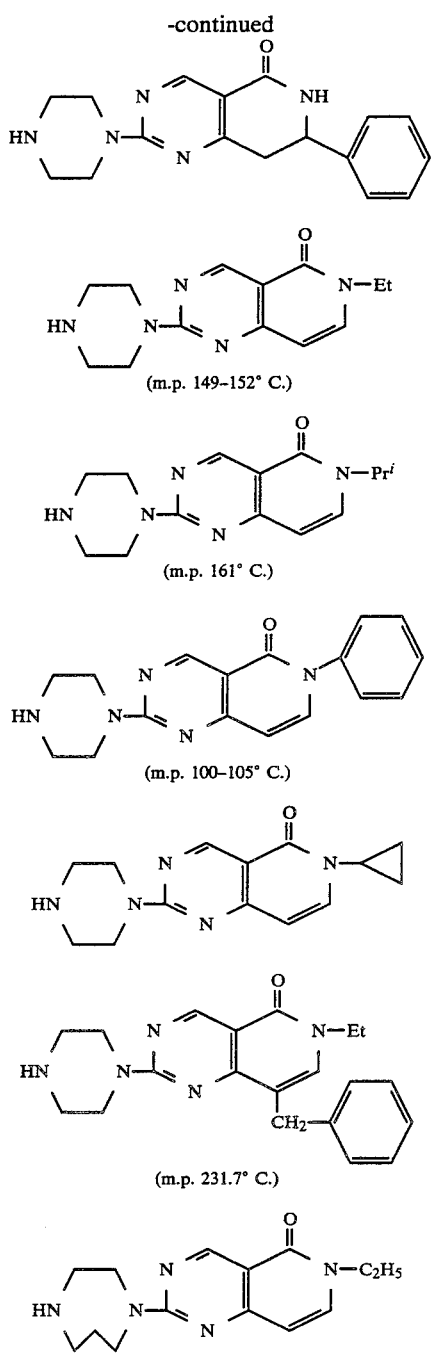

REFERENTIAL EXAMPLE 15

2-(4-Benzylpiperazino)-6-(2-(2'-tetrahydropyranyloxy)ethyl)pyrido[4,3-d]pyrimidine-5(6H)-one

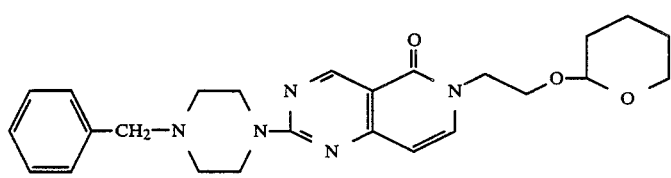

After washing 240 mg of sodium hydride (60% in oil, 6 mmol) with hexane, it was suspended in 2 ml of DMF. Thereafter, a DMF solution (10 ml) of 1.76 g (3 mmol) of 2-(4-benzylpiperazino)-4-methyl-N-(2-(2'-tetrahydropyranyloxy)ethyl)pyrimidine-5-carboxylic acid amide (Referential Example 8) was added. The resultant mixture was stirred at 150° C. for 7 hours. After driving off DMF under reduced pressure, 100 ml of water was added, followed by extraction with ethyl acetate. The ethyl acetate layer was washed with saturated saline and dried with MgSO$_4$, and the solvent was then distilled off under reduced pressure. The residue was purified by silica gel column chromatography (eluent: ethyl acetate) to obtain 0.86 g of the intended product as a yellowish oily substance (yield: 64%).

Infrared absorption spectrum (neat, cm$^{-1}$): 1650, 1615, 1573, 1540, 1505.

$^1$H-NMR spectrum (CDCl$_3$ solution, δ ppm): 1.3–2.0 (6H, m), 2.52 (4H, m), 3.56 (2H, s), 3.4–4.3 (10H, m), 4.56 (1H, m), 6.26 (1H, d, J=7.4 Hz), 7.33 (5H, s), 7.40 (1H, d, J=7.4 Hz), 9.22 (1H, s).

REFERENTIAL EXAMPLE 16

2-Piperazino-6-(2-hydroxyethyl)pyrido[4,3-d]pyrimidine-5(6H)-one

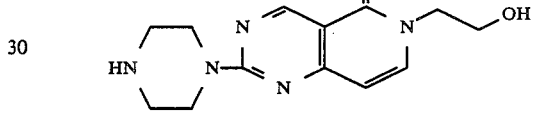

An ethanol-acetic acid solution [15 ml, ethanol/acetic acid=2 (volume ratio] of 450 mg (1 mmol) of the 2-(4-benzylpiperazino)-6-(2(2'-tetrahydropyranyloxy)ethyl)-pyrido[4,3-d]pyrimidine-5(6H)-one obtained in Referential Example 15 was added with 10% Pd-C, to which hydrogen was introduced under atmospheric pressure at 80° C. for 6.5 hours to effect debenzylation. After the reaction, the catalyst was filtered off and the filtrate was concentrated under reduced pressure to obtain the above-identified compound.

REFERENTIAL EXAMPLE 17

2-(4-Benzylpiperazino)-5,6-dihydro-6-ethyl-5-oxopyrido[4,3-d]pyrimidine-8-carbaldehyde

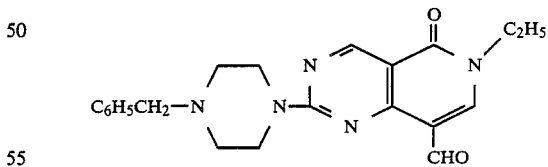

Dissolved in 4.0 ml of diethylformamide was 0.4 g of the 2-(4-benzylpiperazino)-4-methylpyrimidine-5-carboxylic acid obtained in Referential Example 3. At room temperature, 0.5 ml of phosphorus oxychloride was added dropwise. Thereafter, the contents were heated and reacted at 100° C. for 1.5 hours. After cooling, the reaction mixture was poured in an aqueous solution of sodium carbonate to neutralize same, followed by extraction with chloroform. After washing the chloroform layer with water, it was dried with anhydrous magnesium sulfate. Chloroform was distilled off under reduced pressure to obtain 0.29 g of the intended product (yield: 60%).

Melting point: 151.9° C.

Mass spectrum: 377 (molecular ion peak).

Infrared absorption spectrum (KBr tablet, cm$^{-1}$): 1690, 1662, 1628, 1570.

$^1$H-NMR spectrum (CDCl$_3$ solution, δ ppm): 1.39 (3H, t, J=7 Hz), 2.52 (4H, m), 3.58 (2H, s), 4.02 (4H, m), 4.05 (2H, q, J=7 Hz), 7.33 (5H, s), 8.18 (1H, s), 9.19 (1H, s), 10.33 (1H, s).

REFERENTIAL EXAMPLE 18

2-(4-Benzylpiperazino)-5,6-dihydro-6-ethyl-5-oxopyrido[4,3-d]pyrimidine-8-carbaldehydooxime

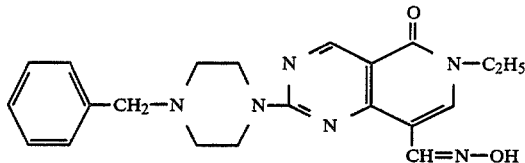

Dissolved in dimethylsulfoxide was 3.0 g of the 2-(4-benzylpiperazino)-5,6-dihydro-6-ethyl-5-oxopyrido[4,3-d]pyrimidine-8-carbaldehyde obtained in Referential Example 17. The solution was heated to 50° C., at which an aqueous solution (10 ml) containing 0.83 g of hydroxylamine hydrochloride and 0.7 g of potassium hydroxide was added dropwise. Thereafter, the contents were stirred and reacted for further 30 minutes. The reaction mixture was poured in water, and the precipitate was collected by filtration and then washed with methanol. It was dried under reduced pressure to obtain 2.65 g of light yellowish crystals (yield: 82%).

Melting point: 226.6° C.

Mass spectrum: 392 (molecular ion peak).

Infrared absorption spectrum (KBr tablet, cm$^{-1}$): 3355, 3174, 1654, 1645, 1582.

$^1$H-NMR spectrum (DMSO-d$_6$ solution, δ ppm): 1.32 (3H, t, J=7 Hz), 2.56 (4H, brs), 3.62 (2H, s), 3.80–4.10 (6H, m), 7.32 (5H, s), 8.06 (1H, s), 8.42 (1H, s), 9.06 (1H, s), 10.87 (1H, s).

REFERENTIAL EXAMPLE 19

Preparation of 2-(4-benzylpiperazino)-5,6-dihydro-6-ethyl-5-oxopyrido[4,3-d]pyrimidinecarbonitrile

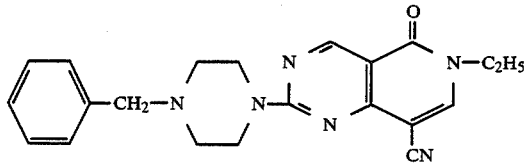

Added to 100 g of phosphorus oxychloride was 3.13 g of the 2-(4-benzylpiperazino)-5,6-dihydro-6-ethyl-5-oxopyrido[4,3-d]pyrimidine-8-carbaldehydooxime obtained in Referential Example 18. The resultant mixture was heated under reflux for 0.5 hr. Excess phosphorus oxychloride was distilled off. Chloroform and a 10% aqueous solution of sodium hydroxide were added to the reaction mixture to neutralize same, followed by extraction with chloroform. The chloroform layer was dried with anhydrous magnesium sulfate. Chloroform was distilled off under reduced pressure and the extract was recrystallized from toluene, thereby obtaining 2.2 g of light yellowish crystals (yield: 74%).

Melting point: 218.3° C.

Mass spectrum: 374 (molecular ion peak).

$^1$H-NMR spectrum (CDCl$_3$ solution, δ ppm): 1.39 (3H, t, J=7 Hz), 2.53 (4H, m), 3.57 (2H, s), 3.90–4.20 (6H, m), 7.33 (5H, s), 7.87 (1H, s), 9.15 (1H, s).

REFERENTIAL EXAMPLE 20

2-(4-Benzyloxycarbonylpiperazino)-5,6-dihydro-6-ethyl-5-oxopyrido[4,3-d]pyrimidine-8-carbaldehyde

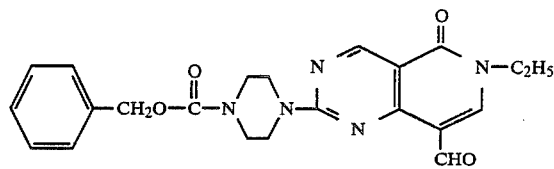

Dissolved in 5.0 ml of tetrahydrofuran was 0.55 g of the 2-(4-benzylpiperazino)-5,6-dihydro-6-ethyl-5-oxopyrido[4,3-d]pyrimidine-8-carbaldehyde obtained in Referential Example 17, to which 0.31 g of benzyl chlorocarbonate was added dropwise at room temperature. The resultant mixture was stirred at 50° C. for further 3 hours. After allowing the reaction mixture to cool, tetrahydrofuran was distilled off under reduced pressure and the residue was washed with n-hexane to obtain 0.55 g of light yellowish crystals (yield: 91%).

Melting point: 208.0°–208.9° C.

Mass spectrum: 421 (molecular ion peak).

Infrared absorption spectrum (nujol, cm$^{-1}$): 1711, 1691, 1657.

$^1$H-NMR spectrum (CDCl$_3$ solution, δ ppm): 1.41 (3H, t, J=7 Hz), 3.62 (4H, m), 4.01 (6H, m), 5.20 (2H, s), 7.38 (5H, s), 8.23 (1H, s), 9.24 (1H, s), 10.56 (1H, s).

The following compound was synthesized in the same manner except that the reaction was carried out at 50° C. for 12 hours by using 2-(4-benzyl-piperazino)-4-methylthiopyrimidine-5-carboxylic acid diethylamide obtained in Referential Example 68 in place of 2-(4-benzylpiperazino)-5,6-dihydro-6-ethyl-5-oxopyrido[4,3-d]pyrimidine-8-carbaldehyde.

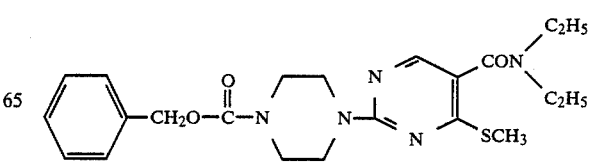

REFERENTIAL EXAMPLE 21

2-(4-Benzyloxycarbonylpiperazino)-5,6-dihydro-6-ethyl-5-oxopyrido[4,3-d]pyrimidine-8-carbaldehydooxime

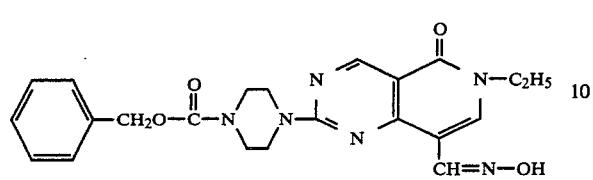

Dissolved in 20 ml of chloroform was 1.0 g of the 2-(4-benzyloxycarbonylpiperazino)-5,6-dihydro-6-ethyl-5-oxopyrido[4,3-d]pyrimidine-8-carbaldehyde obtained in Referential Example 20, to which an aqueous solution of 0.25 g of hydroxylamine hydrochloride and 0.24 g of potassium hydroxide was added at room temperature. Thereafter, the resulting mixture was heated with stirring at 60° C. for 2.5 hours. After allowing the reaction mixture to cool down, the chloroform layer was collected and dried with anhydrous magnesium sulfate. Chloroform was distilled off under reduced pressure and the resultant crude crystals were washed with n-hexane to obtain 0.81 g of light yellowish crystals (yield: 81%).

Melting point: 170.9° C.
Mass spectrum: 436 (molecular ion peak).
Infrared adsorption spectrum (nujol, cm$^{-1}$): 1645, 1583, 1491, 1348.
$^1$H-NMR spectrum (CDCl$_3$ solution, δ ppm): 1.37 (3H, t, J=7.0 Hz), 3.61 (4H, m), 3.96 (6H, m), 5.19 (2H, s), 7.36 (5H, s), 7.93 (1H, s), 8.61 (1H, s), 9.25 (1H, s).

REFERENTIAL EXAMPLE 22

2-(4-Benzyloxypiperazino)-5,6-dihydro-6-ethyl-5-oxopyrido[4,3-d]pyrimidine-8-carbonitrile

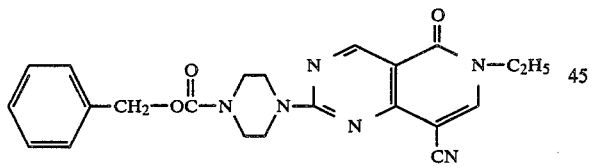

The above-identified compound was synthesized in the same manner as in Referential Example 20 except that the reaction was carried out at room temperature for 12 hours by using 2-(4-benzylpiperazino)-5,6-dihydro-6-ethyl-5-oxo[4,3-d]pyrimidine-8-carbonitrile (Referential Example 19) instead of 2-(4-benzylpiperazino)-5,6-dihydro-6-ethyl-5-oxopyrido[4,3-d]pyrimidine-8-carbaldehyde (slightly yellowish crystals, yield: 79%).

Melting point: 184°–186° C.
Infrared absorption spectrum (KBr tablet, cm$^{-1}$): 2239 (CN), 1709, 1662, 1623, 1580.
$^1$H-NMR spectrum (CDCl$_3$ solution, δ ppm): 1.40 (3H, t, J=7.2 Hz), 3.60 (4H, m), 4.10 (6H, m), 5.20 (2H, s), 7.39 (5H, s), 7.89 (1H, s), 9.20 (1H, s).

Incidentally, the present compound may also be synthesized by dehydrating the compound of Referential Example 21 in the same manner as in Referential Example 19.

REFERENTIAL EXAMPLE 23

5,6-Dihydro-6-ethyl-5-oxo-2-piperazinopyrido[4,3-d]pyrimidine-8-carbaldehyde

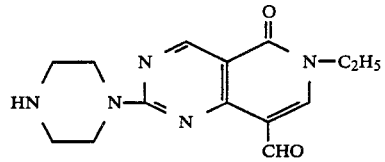

Dissolved in a 25% hydrogen bromide solution of acetic acid was 0.2 g of the 2-(4-benzyloxycarbonylpiperazino)-5,6-dihydro-6-ethyl-5-oxopyrido[4,3-d]pyrimidine-8-carbaldehyde obtained in Referential Example 20. The resulting mixture was stirred at room temperature for 1 hour. Hydrogen bromide, acetic acid and resulting benzyl bromide were distilled off under reduced pressure. After neutralizing the residue with a saturated aqueous solution of sodium carbonate, the mixture was extracted with chloroform and the chloroform layer was dried with anhydrous magnesium sulfate. Chloroform was distilled off under reduced pressure to obtain 0.13 g of light yellowish crystals (yield: 95%).

Melting point: over 300° C.
Infrared absorption spectrum (nujol, cm$^{-1}$): 3400, 1688, 1655.
$^1$H-NMR spectrum (CDCl$_3$ solution, δ ppm): 1.40 (3H, t, J=7.0 Hz), 2.95 (4H, m), 4.08 (6H, m), 8.19 (1H, s), 9.20 (1H, s), 10.55 (1H, s).

The following compound was also synthesized in a similar manner. (The raw material was synthesized in Referential Example 20.)

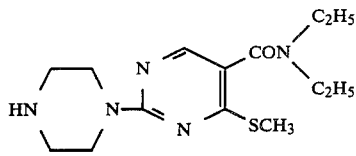

REFERENTIAL EXAMPLE 24

5,6-Dihydro-6-ethyl-5-oxo-2-piperazinopyrido[4,3-d]pyrimidine-8-carbonitrile

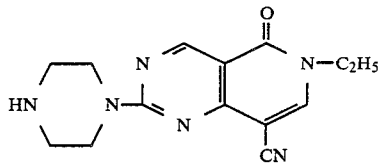

To 0.4 g of the 2-(4-benzyloxycarbonylpiperazino)-5,6-dihydro-6-ethyl-5-oxopyrido[4,3-d]pyrimidine-8-carbonitrile obtained in Referential Example 22, 15 ml of ethanol, 1 ml of acetic acid and 0.2 g of 5% Pd-C were added. The resulting mixture was stirred at 50° C. for 2 hours in a hydrogen atmosphere of normal pressure. Pd-C was removed from the reaction mixture by filtration and the resultant filtrate was concentrated under reduced pressure. The concentrate was added with 20 ml of water and 1 ml of 2M-HCl and then washed with chloroform. The water layer was neutralized with potassium carbonate and then extracted with chloroform. The chloroform solution was dried with anhydrous sodium sulfate and chloroform was then driven off under reduced pressure, thereby obtaining 80 mg of slightly yellowish crystals (yield: 29%).

Melting point: 204°–206° C. (decomposed).

Infrared absorption spectrum (KBr tablet, cm$^{-1}$): 2230 (CN), 1671, 1620, 1578.

$^1$H-NMR spectrum (CDCl$_3$ solution, δ ppm): 1.40 (3H, t, J=7.2 Hz), 1.65 (1H, s), 2.95 (4H, m), 4.00 (6H, m), 7.88 (1H, s), 9.19 (1H, s).

REFERENTIAL EXAMPLE 25

5,6-Dihydro-6-ethyl-5-thioxo-2-piperazinopyrido[4,3-d]pyrimidine

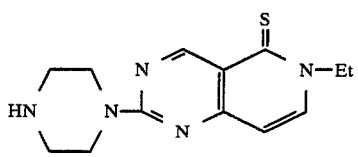

In pyridine (20 ml), 2 g (7.7 mmol) of the 5,6-dihydro-6-ethyl-5-oxo-2-piperazinopyrido[4,3-d]pyrimidine obtained in Referential Example 14 and 6 g (27 mmol) of phosphorus pentasulfide were reacted at 100° C. for 3 hours. Thereafter, pyridine was distilled off under reduced pressure and the residue was taken up in hot water. The resultant aqueous solution was extracted with chloroform. The chloroform layer was dried with anhydrous magnesium sulfate, followed by its concentration. The residue was purified by silica gel column chromatography (eluent: chloroform/methanol=95/5) to obtain 0.3 g of the intended product (yield: 14%).

$^1$H-NMR spectrum (CDCl$_3$ solution, δ ppm): 1.44 (3H, t, J=7.0 Hz), 3.52 (4H, m), 3.98 (2H, m), 4.38 (4H, m), 6.58 (1H, d, J=7.5 Hz), 7.55 (1H, d, J=7.5 Hz), 9.79 (1H, s).

REFERENTIAL EXAMPLE 26

2,4-Dichloro-5-chlorocarbonylpyrimidine

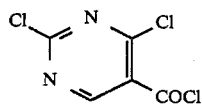

Twenty grams of 2,4-dihydroxypyrimidine-5-carboxylic acid and 220 ml of phosphorus oxychloride were reacted under reflux for 10 hours. Thereafter, the reaction mixture was cooled to room temperature and 100 g of phosphorus pentachloride was added. The contents were again reacted at 120° C. for 7 hours. After completion of the reaction, phosphorus oxychloride was distilled off and the reaction product was purified by its distillation under reduced pressure (b.p. 130°–140° C./1 mmHg, yield: 35%).

REFERENTIAL EXAMPLE 27

2-4-Dichloro-N-ethyl-5-carboxylic acid amide

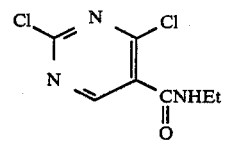

To a solution of 1.02 g (4.8 mmol) of the 2,4-dichloro-5-chlorocarbonylpyrimidine synthesized in Referential Example 26 in methylene chloride (5 ml), 0.6 ml of ethylamine was added at −20° C. The resultant mixture was then reacted at room temperature for 2 hours. Water was added to the reaction mixture, followed by extraction with methylene chloride. After drying the methylene chloride layer with magnesium sulfate, methylene chloride layer was distilled off under reduced pressure to obtain 0.97 g of the intended product as yellowish solid (yield: 91%).

$^1$H-NMR spectrum (CDCl$_3$ solution, δ ppm): 1.28 (3H, t, J=7.2 Hz), 3.52 (2H, m), 8.92 (1H, s).

REFERENTIAL EXAMPLE 28

2-Chloro-N-ethyl-4-methylthio-5-carboxylic acid amide

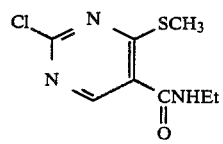

An NaSCH$_3$/MeOH solution, which had been prepared on the side, was added dropwise to 1.15 g (5.2 mmol) of the 2,4-dichloro-N-ethyl-5-carboxylic acid amide prepared in Referential Example 27. Reaction course was monitored by TLC. Upon consumption of the raw material, the reaction mixture was concentrated and was then added with water, followed by extraction with chloroform. The chloroform layer was dried with anhydrous magnesium sulfate. Under reduced pressure, chloroform was distilled off. The residue was purified by silica gel column chromatography to obtain 0.7 g of the intended product (yield: 54%).

Melting point: 188°–190° C.

$^1$H-NMR spectrum (CDCl$_3$ solution, δ ppm): 1.27 (3H, t, J=7.4 Hz), 2.59 (3H, s), 3.50 (2H, d.q, J=5.7 and 7.4 Hz), 6.12 (1H, br.t), 8.47 (1H, s).

The following compound was synthesized in the same manner except that the ethyl 2-(4-benzyl-piperazino)-4-chloropyrimidine-5-carboxylate obtained in Referential Example 63 was used in place of 2,4-dichloro-N-ethyl-5-carboxylic acid amide.

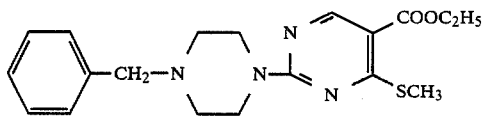

REFERENTIAL EXAMPLE 29

2-(4-Benzylpiperazino)-N-ethyl-4-methylthio-5-carboxylic acid amide

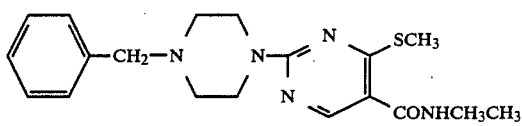

One milliliter of benzylpiperazine was added to 10 ml of a butanol solution in which 1.0 g of the 2-chloro-N-ethyl-4-methylthio-5-carboxylic acid amide synthesized in Referential Example 28 was dissolved. The resultant mixture was refluxed for 2 hours. The reaction mixture was cooled, the precipitated benzylpiperazine hydrochloride was filtered off, and the filtrate was then concentrated under reduced pressure. The concentrate was recrystallized from ethyl acetate, thereby obtaining 600 mg of the intended product as colorless crystals (yield: 41%).

Melting point: 145°–148° C.

$^1$H-NMR spectrum (CDCl$_3$ solution, δ ppm): 1.23 (3H, t, J=7.2 Hz), 2.46 (3H, s), 2.56 (4H, m), 3.46 (2H, d.q, J=5.7 and 7.2 Hz), 3.55 (2H, s), 3.90 (4H, m), 6.20 (1H, br.t), 8.36 (1H, s).

REFERENTIAL EXAMPLE 30

N-Ethyl-2-piperazino-5-carboxylic acid amide

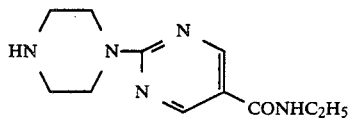

An ethanol solution (10 ml) of 100 mg of the 2-(4-benzylpiperazino)-N-ethyl-4-methylthio-5-carboxylic acid amide synthesized in Referential Example 29 was added with 500 mg of Raney nickel and was then refluxed for 2.5 hours. Raney nickel was filtered off from the reaction mixture and the filtrate was concentrated under reduced pressure. The concentrate was added with 10 ml of methylene chloride and 1 ml of water. The resultant mixture was then allowed to separate into layers. After drying the methylene chloride layer with anhydrous sodium sulfate, it was concentrated to obtain 40 mg of the intended product as a colorless oil (yield: 64%).

$^1$H-NMR spectrum (CDCl$_3$ solution, δ ppm): 1.23 (3H, t, J=7.0 Hz), 2.95 (4H, m), 3.45 (2H, d.q, J=5.3 and 7.0 Hz), 3.85 (4H, m), 6.20 (1H, br.t), 8.71 (2H, s).

REFERENTIAL EXAMPLE 31

1,4,5,6-Tetrahydro-6-ethyl-5-oxo-2-(4-benzylpiperazino)pyrido[4,3-d]pyrimidine

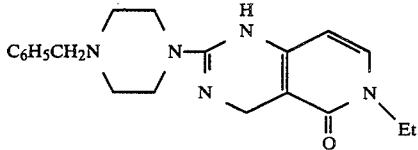

Added at room temperature to a suspension of 0.80 (21 mmol) of lithium aluminum hydride in THF (20 ml) was 1.5 g of 5,6-dihydro-6-ethyl-5-oxo-2-(4-benzylpiperazino)pyrido[4,3-d]pyrimidine (Referential Example 11). After refluxing the reaction mixture for 4 hours, the reaction mixture was added with water to decompose excess lithium aluminum hydride. An aqueous solution of sodium hydroxide and chloroform were added to the resultant mixture to extract the latter. After washing the chloroform layer with water, it was dried with anhydrous magnesium sulfate and was then concentrated to obtain 1.4 g of light yellowish crystals. The crude crystals were immersed in ethyl acetate to obtain 1.1 g of 1,4,5,6-Tetrahydro-6-ethyl-5-oxo-2-(4-benzylpiperazino)pyrido[4,3-d]pyrimidine as colorless crystals (yield: 72%).

Melting point: 200°–203° C.

Mass spectrum: 351 (M+).

Infrared absorption spectrum (CHCl$_3$ solution, cm$^{-1}$): 1640, 1565, 1529.

$^1$H-NMR spectrum (CDCl$_3$ solution, δ ppm): 1.30 (3H, t, J=7 Hz), 2.50 (4H, m), 3.54 (6H, m), 3.90 (2H, q, J=7 Hz), 4.42 (2H, s), 4.87 (1H, brs), 5.92 (1H, d, J=7.5 Hz), 7.03 (1H, d, J=7.5 Hz), 7.32 (5H, m).

The following compound was also synthesized in a similar manner.

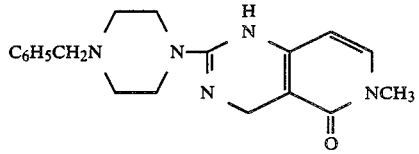

(m.p. 181–183° C.)

REFERENTIAL EXAMPLE 32

1,4,5,6-Tetrahydro-6-ethyl-5-oxo-2-piperazinopyrido[4,3-d]pyrimidine

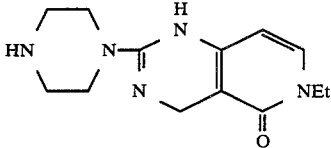

Dissolved in 20 ml of ethanol was 1.0 g of the 1,4,5,6-tetrahydro-6-ethyl-5-oxo-2-(4-benzylpiperazino)-pyrido[4,3-d]pyrimidine obtained in Referential Example 31, followed by an addition of 10% Pd-C. The resultant mixture was stirred at 70° C. for 2.5 hours in a hydrogen atmosphere. After removal of the catalyst by filtration, the filtrate was concentrated to obtain 0.7 g of 1,4,5,6-Tetrahydro-6-ethyl-5-oxo-2-piperazinopyrido[4,3-d]pyrimidine as crystals (yield: 95%).

Melting point: 117°–120° C. (decomposed, deliquescent).

Mass spectrum: 247 (M+).

$^1$H-NMR spectrum (CDCl$_3$ solution, δ ppm): 1.30 (3H, t, J=7 Hz), 2.90 (4H, m), 3.55 (4H, m), 3.88 (2H, q, J=7 Hz), 4.40 (2H, s), 5.98 (1H, d, J=7.5 Hz), 7.03 (1H, d, J=7.5 Hz).

The following compound was also synthesized in a similar manner.

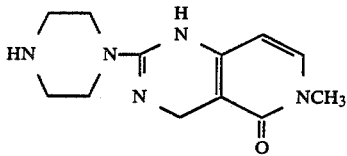

REFERENTIAL EXAMPLE 33

Ethyl 3-ethylaminopropionate

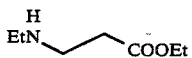

Dissolved in 500 ml of ethanol was 50 g (0.50 mol) of ethyl acrylate. While stirring the thus-prepared solution while ice cooling, a liquid mixture of 36 g (0.55 mol) of a 70% aqueous solution of ethylamine and 100 ml of ethanol was added dropwise over 3.5 hours. After allowing the reaction to proceed for further 3 hours, the solvents were distilled off. The residue was distilled under reduced pressure to obtain 50.5 g of the intended product as colorless liquid (yield: 70%).

Boiling point: 65° C./10 mmHg.

Infrared absorption spectrum (neat, cm$^{-1}$): 3320 (broad), 1735.

$^1$H-NMR spectrum (CDCl$_3$ solution, δ ppm): 1.0–1.4 (6H, m), 2.4–3.0 (6H, m), 4.16 (2H, q, J=7.0 Hz).

REFERENTIAL EXAMPLE 34

Ethyl N-ethoxycarbonylacetyl-3-ethylaminopropionate

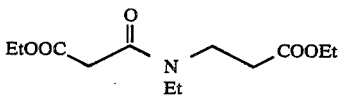

While stirring with ice-cooling a mixture of 45 g (0.30 mol) of the ethyl 3-ethylaminopropionate obtained in Referential Example 33, 37.3 g (0.27 mol) of potassium carbonate, 250 ml of toluene and 250 ml of water, 67.7 g (0.45 mol) of ethylmalonyl chloride was dropped over 0.5 hour. After mixing the resultant mixture at room temperature for further 3 hours, the reaction mixture was allowed to separate into layers. The toluene layer was washed successively with 5% hydrochloric acid, saturated aqueous solution of sodium bicarbonate, and saturated saline, and was then dried with anhydrous magnesium sulfate. Toluene was distilled off under reduced pressure to obtain 64.3 g of the intended product as colorless liquid (yield: 83%).

Infrared absorption spectrum (neat, cm$^{-1}$): 1735, 1648.

$^1$H-NMR spectrum (CDCl$_3$ solution, δ ppm): 1.1–1.3 (6H), 2.64 (2H), 3.2–3.8 (6H), 4.0–4.2 (4H).

REFERENTIAL EXAMPLE 35

3-Carboethoxy-1-ethylpiperidine-2,4-dione

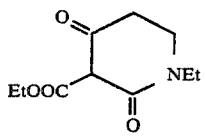

To an ethanol solution of sodium ethoxide which had been synthesized by adding 5.8 g of metallic sodium to 300 ml of ethanol, 62.2 g of ethyl N-ethoxycarbonylacetyl-3-ethylaminopropionate (Referential Example 34) was added. The resultant mixture was refluxed for 4 hours. After allowing the reaction mixture to cool down, ethanol was distilled off. Ethyl acetate and a dilute aqueous solution of hydrogen chloride were added. The resulting mixture was shaken. After washing the organic layer with water, it was dried and concentrated to obtain 36.3 g of 3-carboethoxy-1-ethylpiperidine-2,4-dione as an oily substance (yield: 71%).

$^1$H-NMR spectrum (CDCl$_3$ solution, δ ppm): 1.28 (6H, m), 2.66 (2H, m), 3.44 (4H, m), 4.32 (2H, m).

REFERENTIAL EXAMPLE 36

1-Ethylpiperidine-2,4-dione

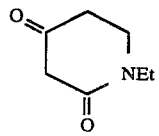

Added to 36.0 g of 3-carboethoxy-1-ethylpiperidine-2,4-dione (Referential Example 35) was 300 ml of a 10% aqueous solution of hydrochloric acid. The resultant mixture was refluxed for 40 minutes. After allowing the reaction mixture to cool down, it was extracted with chloroform. The chloroform layer was washed with water, dried and then concentrated, thereby obtaining 16.6 g of 1-ethylpiperidine-2,4-dione as a light yellowish oily substance (yield: 70%).

$^1$H-NMR spectrum (CDCl$_3$ solution, δ ppm): 1.20 (3H, t, J=7 Hz), 2.64 (2H, t, J=7 Hz), 3.36 (2H, s), 3.54 (4H, m).

REFERENTIAL EXAMPLE 37

1-Ethyl-3-methoxymethylenepiperidine-2,4-dione

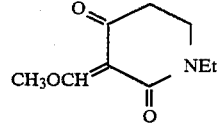

Added to 8.3 g of 1-ethylpiperidine-2,4-dione were 11 g of methyl orthoformate and 20 ml of acetic anhydride. The resultant mixture was refluxed for 7 hours. After allowing the reaction mixture to cool down, excess methyl orthoformate and acetic anydride were distilled off under reduced pressure. The brown residue was distilled under reduced pressure in a Kugelroll apparatus (0.5 mmHg; bath temperature: 200°–250° C.) to obtain 2.7 g of 1-ethyl-3-methoxymethylenepiperidine-2,4- dione as crystals (yield: 25%). The crystals were recrystallized from a mixed solvent of ethyl acetate and hexane to obtain needles.

$^1$H-NMR spectrum (CDCl$_3$ solution, δ ppm): 1.20 (3H, m), 2.64 (2H, t, J=7 Hz), 3.50 (4H, m), 4.12 (3H, s), 7.86 (1H, two singlets).

REFERENTIAL EXAMPLE 38

2-(4-Benzylpiperazino)-6-ethyl-5-oxo-5,6,7,8-tetrahydropyrido[4,3-d]pyrimidine

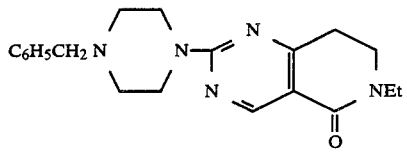

To a suspension which had been obtained by adding 1.56 g of 1-amidino-4-benzylpiperazine sulfate to an ethanol solution of 0.23 g of sodium hydroxide, 1.07 g of 1-ethyl-3-methoxymethylenepiperidine-2,4-dione (Referential Example 37) was added. The resultant mixture was refluxed for 2 hours. After distilling off ethanol, water was added to the residue, followed by extraction with chloroform. After drying the chloroform layer, it was concentrated to obtain 1.4 g of 2-(4-benzylpiperazino)-6-ethyl-5-oxo-5,6,7,8-tetrahydropyrido[4,3-d]pyrimidine (yield: 69%).

Melting point: 128°–130° C.

$^1$H-NMR spectrum (CDCl$_3$ solution, δ ppm): 1.20 (3H, t, J=7 Hz), 2.50 (4H, m), 2.94 (2H, t, J=8 Hz), 3.55 (6H, m), 3.92 (4H, m), 7.32 (5H, m), 8.92 (1H, s).

REFERENTIAL EXAMPLE 39

6-Ethyl-5-oxo-2-piperazino-5,6,7,8-tetrahydropyrido[4,3-d]pyrimidine

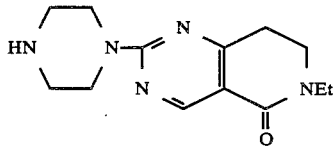

Dissolved in 20 ml of ethanol was 0.70 g of 2-(4-benzylpiperazino)-6-ethyl-5-oxo-5,6,7,8-tetrahydropyrido[4,3-d]pyrimidine (Referential Example 38), followed by an addition of 10% Pd-C. The resultant mixture was stirred at 60° C. for 4 hours in a hydrogen atmosphere. After allowing the reaction mixture to cool down, the catalyst was filtered off and the filtrate was concentrated to obtained 0.50 g of 6-ethyl-5-oxo-2-piperazino-5,6,7,8-tetrahydropyrido[4,3-d]pyrimidine as crystals (yield: 96%). The crystals were purified by their immersion in ethyl acetate.

Melting point: 205°–210° C.

$^1$H-NMR spectrum (CDCl$_3$ solution, δ ppm): 1.20 (3H, t, J=7 Hz), 3.00 (6H, m), 3.60 (4H, m), 3.94 (4H, m), 8.84 (1H, s).

REFERENTIAL EXAMPLE 40:

Ethyl 4-chloro-2-ethoxymethylacetoacetate

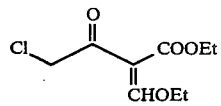

After heating and stirring 10 g (60.7 mmol) of ethyl 4-chloroacetoacetate, 18 g (121 mmol) of ethyl orthoformate and 25 g (245 mmol) of acetic anhydride at 110° C. for 3 hours, excess ethyl orthoformate and acetic anhydride were distilled off under reduced pressure and the residue was recrystallized from hexane to obtain 12.1 g of a solid substance as needles (yield: 90%).

Melting point: 86.5° C.

$^1$H-NMR spectrum (CDCl$_3$ solution, δ ppm): 1.35 (3H, t, J=7 Hz), 1.44 (3H, t, J=7 Hz), 4.30 (2H, q, J=7 Hz), 4.33 (2H, q, J=7 Hz), 4.56 (2H, s), 7.88 (1H, s).

Infrared absorption spectrum (KBr tablet, cm$^{-1}$): 2900, 2830, 1686, 1670, 1575, 1250, 1018.

REFERENTIAL EXAMPLE 41

Ethyl 4-chloromethyl-2-(4-benzylpiperazino)pyrimidine-5-carboxylate

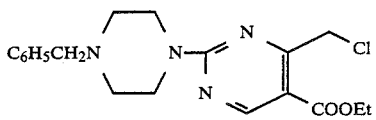

A solution, which had been prepared by dissolving 1.5 g of NaOH in 15 ml of H$_2$O, was added to a suspension of 9.7 g (36.4 mmol) of 1-amidino-4-benzylpiperazine sulfate and 185 ml of THF to neutralize the suspension.

Thereafter, a solution of 8 g (36.4 mmol) of the ethyl 4-chloro-2-ethoxymethyleneacetoacetate obtained in Referential Example 40 in 200 ml of THF was added dropwise at 20° C. After completion of the dropwise addition, 300 ml of ether was added. The resultant mixture was washed three times with water. After drying the organic layer with anhydrous MgSO$_4$, the solvent was distilled off under reduced pressure to obtain 11.8 g of the intended product with a light yellowish color (yield: 86.7%).

$^1$H-NMR spectrum (CDCl$_3$ solution, δ ppm): 1.37 (3H, t, J=7 Hz), 2.51 (4H, t, J=6 Hz), 3.75 (2H, s), 3.97 (4H, t, J=6 Hz), 4.34 (2H, q, J=7 Hz), 4.88 (2H, s), 7.32 (5H, s), 8.87 (1H, s).

Infrared absorption spectrum (neat, cm$^{-1}$): 2873, 2780, 1706, 1582, 1526, 1445, 1350, 1250, 1090, 1000, 742, 696.

REFERENTIAL EXAMPLE 42

2-(4-Benzylpiperazino)-5-oxo-5,6-dihydro(7H)pyrrolo[3,4-d]pyrimidine

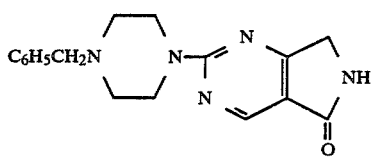

Dissolved in 10 ml of ethanol was 2.25 g (6 mmol) of ethyl 4-chloromethyl-2-(4-benzylpiperazino)pyrimidine-5-carboxylate (Referential Example 41), followed by an addition of 10 ml (59 mmol) of a 30% aqueous NH4OH solution at 20° C. The resultant mixture was stirred for 12 hours. The reaction mixture was poured in a 10% aqueous NaHCO3 solution, followed by extraction with CHCl3. The solvent was then distilled off and the residue was recrystallized from toluene.

Yield: 0.70 g (38%).

Melting point: 172° C.

$^1$H-NMR spectrum (DMSO-$d_6$ solution, δ ppm): 2.45 (4H, t, J=6 Hz), 3.50 (2H, s), 3.83 (4H, t, J=6 Hz), 4.20 (2H, s), 7.30 (5H, s), 8.20 (1H, br.s), 8.57 (1H, s).

Infrared absorption spectrum (nujol, cm$^{-1}$): 2900, 1715, 1674, 1607, 1562, 1218, 1145, 730, 720.

REFERENTIAL EXAMPLE 43

2-Piperazino-5-oxo-5,6-dihydro(7H)pyrrolo[3,4-d]pyrimidine

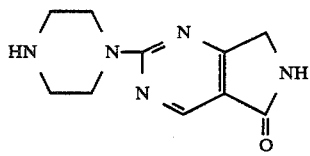

While heating at 60° C. 1.6 g (5.18 mmol, Referential Example 42) of 2-(4-benzylpiperazino)-5-oxo-5,6-dihydro(7H)pyrrolo[3,4-d]pyrimidine, 0.16 g of 10% Pd-C and 30 ml of AcOH, H2 was bubbled. One hour later, Pd-C was filtered off and then the solvent was distilled off. The residue was suspended in a 10% aqueous NaHCO3 solution.

Insoluble matter was collected by filtration. Toluene was added to the solid and then toluene was distilled off under reduced pressure to obtain 0.75 g of the intended product (yield: 66%; oil).

$^1$H-NMR spectrum (DMSO-$d_6$ solution, δ ppm): 2.80 (4H, br.s), 3.24 (1H, br.s), 3.78 (4H, br.s), 4.23 (2H, s), 8.18 (1H, br.s), 8.58 (1H, s).

Infrared absorption spectrum (KBr tablet, cm$^{-1}$): 3210, 3100, 2920, 2880, 1700, 1612, 1260, 1150, 980.

REFERENTIAL EXAMPLE 44

6-Ethyl-2-(4-benzylpiperazino)-5-oxo-5,6-dihydro(7H)pyrrolo[3,4-d]pyrimidine

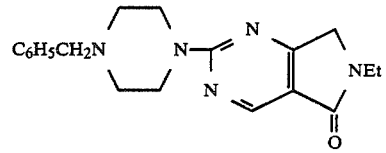

Dissolved in 10 ml of ethanol was 1.0 g (2.7 mmol, Referential Example 41) of ethyl 4-chloromethyl-2-(4-benzylpiperazino)pyrimidine-5-carboxylate, followed by an addition of 5 g (59 mmol) of a 70% aqueous solution of ethylamine at 20° C. The resultant mixture was stirred for 2 hours and was stirred for further 0.5 hour at 80° C.

After completion of the reaction, the reaction mixture was poured in water, neutralized with a 10% aqueous NaHCO3 solution, and then extracted with ether. After drying the organic layer, the solvent was distilled off and the residue was recrystallized from toluene/hexane [yield: 0.82 g (91%)].

Melting point: 159.2° C.

$^1$H-NMR spectrum (CDCl3 solution, δ ppm): 1.22 (3H, t, J=7 Hz), 2.50 (4H, t, J=6 Hz), 3.55 (2H, s), 3.59 (2H, q, J=7 Hz), 3.93 (4H, t, J=6 Hz), 4.18 (2H, s), 7.32 (5H, s), 8.64 (1H, s).

Infrared absorption spectrum (nujol, cm$^{-1}$): 2900, 1666, 1624, 1566, 1280, 1148, 1000, 975, 795, 733.

Each of the following four compounds was also obtained in a similar manner.

6-Methyl-2-(4-benzylpiperazino)-5-oxo-5,6-dihydro(7H)pyrrolo[3,4-d]pyrimidine

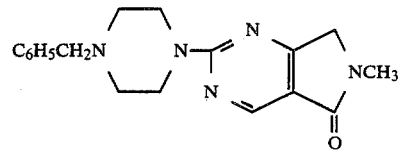

Yield: 94%.

Melting point: 178°–179° C.

$^1$H-NMR spectrum (CDCl3 solution, δ ppm): 2.52 (4H, m), 3.15 (3H, s), 3.58 (2H, s), 3.96 (4H, m), 4.20 (2H, s), 7.36 (5H, m), 8.65 (H, s).

Infrared absorption spectrum (CHCl3, cm$^{-1}$): 1685, 1618, 1522, 1350.

6-Isopropyl-2-(4-benzylpiperazino)-5-oxo-5,6-dihydro(7H)pyrrolo[3,4-d]pyrimidine

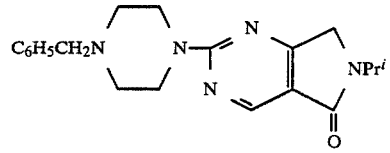

Yield: 39%.

Melting point: 173°–174° C.

$^1$H-NMR spectrum (CDCl3 solution, δ ppm): 1.25 (6H, d, J=7 Hz), 2.52 (4H, m), 3.58 (2H, s), 3.96 (4H, m), 4.16 (2H, s), 4.64 (1H, sept., J=7 Hz), 7.36 (5H, m), 8.66 (1H, s).

Infrared absorption spectrum (CHCl$_3$, cm$^{-1}$): 1680, 1618, 1530, 1345.

6-n-Propyl-2-(4-benzylpiperazino)-5-oxo-5,6-dihydro(7H)pyrrolo[3,4-d]pyrimidine

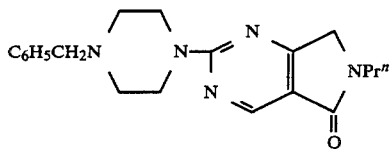

Yield: 67%.
Melting point: 148°–150° C.
$^1$H-NMR spectrum (CDCl$_3$ solution, δ ppm): 0.95 (3H, t, J=7 Hz), 1.65 (2H, hextet, J=7 Hz), 2.52 (4H, m), 3.52 (2H, t, J=7 Hz), 3.58 (2H, s), 3.96 (4H, m), 4.21 (2H, s), 7.37 (5H, s), 8.68 (1H, s).

Infrared absorption spectrum (CHCl$_3$, cm$^{-1}$): 3000, 1680, 1610, 1520, 1342, 1000.

6-n-Butyl-2-(4-benzylpiperazino)-5-oxo-5,6-dihydro(7H)pyrrolo[3,4-d]pyrimidine

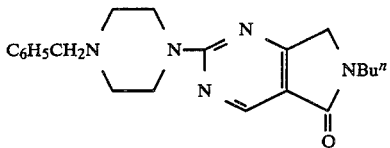

Yield: 62%.
Melting point: 144°–146° C.
$^1$H-NMR spectrum (CDCl$_3$ solution, δ ppm): 0.96 (3H, t, J=7 Hz), 1.16–1.80 (4H), 2.52 (4H, m), 3.57 (2H, s), 3.57 (2H, t, J=7 Hz), 3.96 (4H, m), 4.20 (2H, s), 7.37 (5H, s), 8.68 (1H, s).

Infrared absorption spectrum (CHCl$_3$, cm$^{-1}$): 3010, 1680, 1610, 1520, 1342, 1000.

REFERENTIAL EXAMPLE 45

6-Ethyl-2-piperazino-5-oxo-5,6-dihydro(7H)pyrrolo[3,4-d]pyrimidine

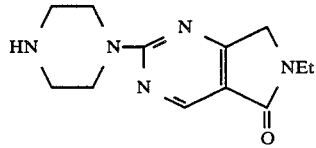

Added to 20 ml of AcOH were 1.5 g (4.45 mmol, Referential Example 44) of 6-ethyl-2-(4-benzylpiperazino)-5-oxo-5,6-dihydro(7H)pyrrolo[3,4-d]pyrimidine and 0.15 g of 10% Pd-C. While bubbling H$_2$ at 80° C., the reaction was conducted for 1 hour.

After completion of the reaction, Pd-C was filtered off, AcOH was distilled off under reduced pressure, the residue was dissolved in chloroform, and the chloroform solution was neutralized with a 10% aqueous NaHCO$_3$ solution. Thereafter, the organic layer was dried with anhydrous MgSO$_4$, the solvent was distilled off, and the residue was purified by silica gel column chromatography [yield: 0.50 g (45%)].

Melting point: 58.5° C.
$^1$H-NMR spectrum (CDCl$_3$ solution, δ ppm): 1.24 (3H, t, J=7 Hz), 2.12 (1H, br.s), 2.95 (4H, br.s), 3.62 (2H, q, J=7 Hz), 3.92 (4H, br.s), 4.21 (2H, s), 8.66 (1H, s).

Infrared absorption spectrum (KBr tablet, cm$^{-1}$): 3480, 3300, 2900, 1650, 1618, 1520, 1438, 1236, 1160, 862.

Each of the following four compounds was also obtained in a similar manner.

6-Methyl-2-piperazino-5-oxo-5,6-dihydro(7H)pyrrolo[3,4-d]pyrimidine

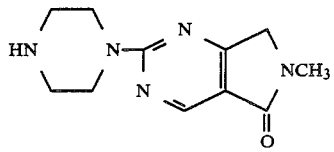

Yield: about 100%.
Melting point: 176°–177° C.
$^1$H-NMR spectrum (CDCl$_3$ solution, δ ppm): 2.98 (4H, m), 3.18 (3H, s), 3.96 (4H, m), 4.24 (2H, s), 8.70 (1H, s).

Infrared absorption spectrum (CHCl$_3$, cm$^{-1}$): 1685, 1618, 1522, 1350.

6-Isopropyl-2-piperazino-5-oxo-5,6-dihydro(7H)pyrrolo[3,4-d]pyrimidine

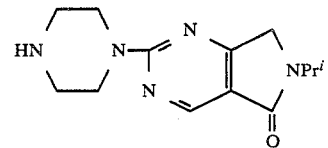

Yield: 96%
Melting point: 161°–162° C.
$^1$H-NMR spectrum (CDCl$_3$ solution, δ ppm): 1.28 (6H, d, J=7 Hz), 2.96 (4H, m), 3.94 (4H, m), 4.18 (2H, s), 4.65 (1H, sept., J=7 Hz), 8.70 (1H, s).

Infrared absorption spectrum (CHCl$_3$, cm$^{-1}$): 1680, 1618, 1520, 1345.

6-n-Propyl-2-piperazino-5-oxo-5,6-dihydro(7H)pyrrolo[3,4-d]pyrimidine

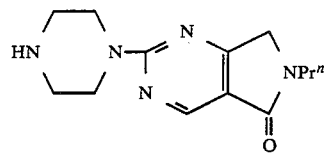

Yield: about 100%.
Melting point: 133°–137° C.
$^1$H-NMR spectrum (CDCl$_3$ solution, δ ppm): 0.96 (3H, t, J=7 Hz), 1.66 (2H, hextet, J=7 Hz), 1.83 (1H, s), 2.96 (4H, m), 3.53 (2H, t, J=7 Hz), 3.93 (4H, m), 4.22 (2H, s), 8.70 (1H, s).

Infrared absorption spectrum (CHCl$_3$, cm$^{-1}$): 3400, 3340, 3000, 2970, 1680, 1610, 1570, 1520, 1345, 1260.

6-n-Butyl-2-piperazino-5-oxo-5,6-dihydro(7H)pyrrolo[3,4-d]pyrimidine

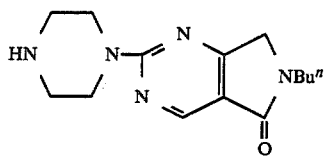

Yield: about 100%.
Melting point: 108°–112° C.
$^1$H-NMR spectrum (CDCl$_3$ solution, δ ppm): 0.95 (3H, t, J=7 Hz), 1.65 (2H, hextet, J=7 Hz), 2.52 (4H, m), 3.52 (2H, t, J=7 Hz), 3.58 (2H, s), 3.96 (4H, m), 4.21 (2H, s), 7.37 (5H, s), 8.68 (1H, s).
Infrared absorption spectrum (CHCl$_3$, cm$^{-1}$): 3430, 3340, 3000, 2960, 2930, 1680, 1610, 1575, 1520, 1455, 1435, 1350.

REFERENTIAL EXAMPLE 46

2-Dimethylaminomethylenecyclohexane-1,3-dione

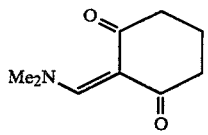

While stirring 5.60 g (50 mmol) of cyclohexane-1,3-dione under ice-cooling, 11.9 g (100 mmol) of N,N-dimethylformamidodimethylacetal was added dropwise. They were reacted at 25° C. for further 7 hours. Low b.p. fractions were distilled off under reduced pressure from the reaction mixture. The residue was recrystallized from ethyl acetate-hexane to obtain 7.7 g of the intended product as yellowish crystals (yield: 92%).
Melting point: 106°–107° C.
$^1$H-NMR spectrum (CDCl$_3$ solution, δ ppm): 1.92 (2H, m), 2.47 (4H, m), 3.18 (3H, s), 3.40 (3H, s), 8.05 (1H, s).

REFERENTIAL EXAMPLE 47

2-(4-Benzylpiperazino)-5-oxo-5,6,7,8-tetrahydroquinazoline

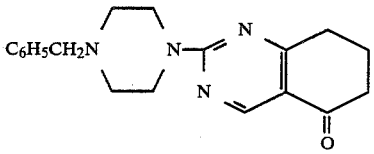

To an ethanol suspension (60 ml) of 10.73 g (40 mmol) of 1-amidino-4-benzylpiperazine sulfate, were added an ethanol solution (80 ml) of 1.6 g (40 mmol) of sodium hydroxide and then 6.69 g (40 mmol) of the 2-dimethylaminomethylenecyclohexane-1,3-dione obtained in Referential Example 46. The resultant mixture was heated under reflux for 4 hours. After cooling the reaction mixture to room temperature, the solvent was distilled off. The residue was added with 100 ml of water and then extracted twice with 200 ml of ethyl acetate. The ethyl acetate layer was washed with saturated saline and then dried with anhydrous magnesium sulfate. Ethyl acetate was the distilled off under reduced pressure. The residue was purified by silica gel column chromatography (eluent: ethyl acetate/hexane=3/7) to obtain 9.90 g of the intended product as light yellowish crystals (yield: 77%).
Melting point: 96°–97° C.
Infrared absorption spectrum (KBr tablet, cm$^{-1}$): 1665, 1590, 1530, 1515.
$^1$H-NMR spectrum (CDCl$_3$ solution, δ ppm): 2.08 (2H, m), 2.5 (6H, m), 2.80 (2H, m), 3.54 (2H, s), 3.96 (4H, m), 7.32 (5H, s), 8.83 (1H, s).

REFERENTIAL EXAMPLE 48

2-Piperazino-5-oxo-5,6,7,8-tetrahydroquinazoline

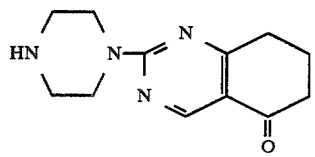

Dissolved in 30 ml of ethanol and 10 ml of acetic acid was 0.64 g (2 mmol, Referential Example 47) of 2-(4-benzylpiperazino)-5-oxo-5,6,7,8-tetrahydroquinazoline, followed by an addition of 64 mg of 10% Pd-C. The quinazoline derivative was hydrogenated at 50° C. for 1 hour under atmospheric pressure. After cooling the reaction mixture to room temperature, the catalyst was filtered off and the solvent was distilled off from the filtrate under reduced pressure. The residue was recrystallized from ethyl acetate to obtain 0.42 g of the intended product as light yellowish crystals (yield: 90%).
Melting poing: 161°–162° C.
Infrared absorption spectrum (KBr tablet, cm$^{-1}$): 3400 (broad), 1670, 1600, 1530.
$^1$H-NMR spectrum (CDCl$_3$ solution, δ ppm): 2.10 (2H, m), 2.60 (2H, m), 2.84 (2H, m), 3.06 (4H, m), 4.08 (4H, m), 8.85 (1H, s).

REFERENTIAL EXAMPLE 49

2-(4-Benzylpiperazino)-5,6,7,8-tetrahydro-5-hydroxyiminoquinazoline

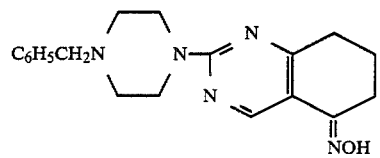

Added to 30 ml of methanol were 2.6 g (8.07 mmol, Referential Example 48) of 2-(4-benzylpiperazino)-5-oxo-5,6,7,8-tetrahydroquinazoline and 0.67 g (9.64 mmol) of hydroxylamine hydrochloride. The resultant mixture was heated with stirring at 60° C. for 2 hours. The reaction mixture was cooled to 20° C. and the resultant precipitate was collected by filtration, thereby obtaining 2.85 g of white solid (yield: 95%).
Melting point: over 300° C. (decomposed).
$^1$H-NMR spectrum (CDCl$_3$ solution, δ ppm): 1.80 (2H, m), 2.40–2.90 (8H, m), 3.58 (2H, s), 3.92 (4H, t, J=6 Hz), 7.34 (5H, s), 8.91 (1H, s).
Infrared absorption spectrum (KBr tablet, cm$^{-1}$): 3150, 2920, 2444, 1618, 1582, 1510, 1500, 1275, 1032, 955.

REFERENTIAL EXAMPLE 50

2-(4-Benzylpiperazino)-5,6,7,8-tetrahydro-5-(p-toluenesulfonyl)iminoquinazoline

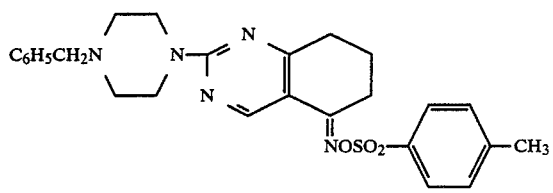

Added to a mixture of 30 ml of acetone, 2 g (5.35 mmol, Referential Example 49) of 2-(4-benzylpiperazino)-5,6,7,8-tetrahydro-5-hydroxyiminoquinazoline, and 1.6 g (8.4 mmol) of p-toluenesulfonyl chloride was a solution of 0.7 g (11 mmol) of KOH in 10 ml of water. The resultant mixture was stirred at 20° C. for 4 hours.

After completion of the reaction, the reaction mixture was poured in saline and then extracted with ethyl acetate. The organic layer was dried to solid and the residue was purified by silica gel column chromatography (eluent: CHCl$_3$-ethanol), thereby obtaining 1.5 g of white solid (yield: 59%).

Melting point: 180.6° C.

$^1$H-NMR spectrum (CDCl$_3$ solution, δ ppm): 1.68–1.98 (2H, m), 2.44 (3H, s), 2.46–2.85 (8H, m), 3.57 (2H, s), 3.90 (4H, t, J=6 Hz), 7.26–7.40 (7H, m), 7.86 (1H, s), 7.95 (1H, s), 8.69 (1H, s).

Infrared absorption spectrum (KBr tablet, cm$^{-1}$): 2920, 1578, 1526, 1424, 1188, 1176, 1005, 992.

REFERENTIAL EXAMPLE 51

2-(4-Benzylpiperazino)-6-oxo-6,7,8,9-tetrahydro(5H-)pyrimido[5,4-b]azepine

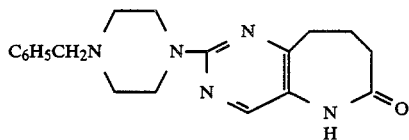

Dissolved in 30 ml of acetic acid was 1.3 g (4 mmol, Referential Example 50) of 2-(4-benzylpiperazino)-5,6,7,8-tetrahydro-5-(p-toluenesulfonyl)iminoquinazoline). The resultant mixture was heated at 100° C. for 4 hours. After completion of the reaction, acetic acid was distilled off. The residue was dissolved in CHCl$_3$. After neutralizing and washing the thus-obtained chloroform solution with a 10% aqueous NaHCO$_3$ solution, the solvents were distilled off and the residue was recrystallized from toluene to obtain 0.70 g of white solid (yield: 97%).

Melting point: 210.7° C.

$^1$H-NMR spectrum (CDCl$_3$ solution, δ ppm): 2.26–2.40 (4H, m), 2.49 (4H, t, J=6 Hz), 2.83 (2H, t, J=7 Hz), 3.55 (2H, s), 3.82 (4H, t, J=6 Hz), 7.32 (5H, s), 7.83 (1H, s), 7.94 (1H, s).

Infrared absorption spectrum (KBr tablet, cm$^{-1}$): 3150, 2900, 2830, 1660, 1595, 1346, 1010, 982.

REFERENTIAL EXAMPLE 52

5-Ethyl-2-(4-benzylpiperazino)-6-oxo-6,7,8,9-tetrahydro(5H)pyrimido[5,4-b]azepine

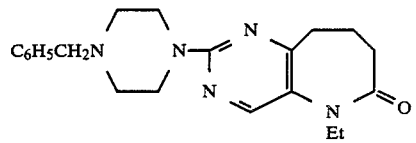

Added to 30 ml of THF were 0.65 g (1.84 mmol, Referential Example 51) of 2-(4-benzylpiperazino)-6-oxo-6,7,8,9-tetrahydro(5H)pyrimido[5,4-b]azepine and 0.15 g (3.75 mmol) of 60% NaH. The resultant mixture was stirred at 20° C. for 30 minutes. Thereafter, 3 g (27.8 mmol) of ethyl bromide was added and the reaction mixture was heated to 60° C. at which the reaction was conducted for 5 hours. After completion of the reaction, the solvent was distilled off and the residue was purified by silica gel column chromatography to obtain 0.65 g of a colorless oil (yield: 92%).

$^1$H-NMR spectrum (CDCl$_3$ solution, δ ppm): 1.15 (3H, t, J=7 Hz), 2.16–2.38 (4H, m), 2.53 (4H, t, J=6 Hz), 2.74 (2H, t, J=5.5 Hz), 2.58 (2H, s), 3.80 (2H, q, J=7 Hz), 3.87 (4H, t, J=6 Hz), 7.35 (5H, s), 8.13 (1H, s).

Infrared absorption spectrum (KBr tablet, cm$^{-1}$): 2920, 1657, 1589, 1444, 1250, 1000, 980.

REFERENTIAL EXAMPLE 53

5-Ethyl-2-piperazino-6-oxo-6,7,8,9-tetrahydro(5H-)pyrimido[5,4-b]azepine

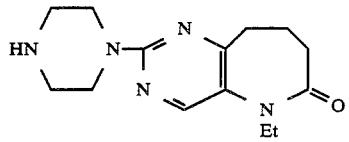

To a mixed solvent of 30 ml of acetic acid and 10 ml of ethanol, 0.6 g (2.18 mmol, Referential Example 52) of 5-ethyl-2-(4-benzylpiperazino)-6-oxo-6,7,8,9-tetrahydro(5H)pyrimido[5,4-b]azepine and 0.06 g of 10% Pd-C were added. While causing hydrogen gas to flow through the reaction mixture, the reaction was allowed to proceed at 100° C. for 4 hours. Thereafter, the Pd/C was filtered off and the filtrate was dried to obtain 0.5 g of a light yellowish oily substance (yield: about 100%).

$^1$H-NMR spectrum (CDCl$_3$ solution, δ ppm): 1.16 (3H, t, J=7 Hz), 2.21–2.40 (4H, m), 2.75 (2H, t, J=5.5 Hz), 2.96 (4H, t, J=6 Hz), 3.70–4.05 (6H, m), 8.15 (1H, s).

Infrared absorption spectrum (neat, cm$^{-1}$): 3460, 3300, 2940, 1650, 1595, 1445, 1128, 984.

Similarly, the following compound was also obtained by the following procedure.

2-Piperazino-6-oxo-6,7,8,9-tetrahydro(5H-)pyrimido[5,4-b]azepine

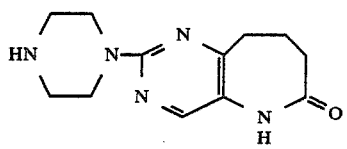

Added to 20 ml of ethanol were 0.1 g (0.3 mmol, Referential Example 51) of 2-(4-benzylpiperazino)-6-oxo-6,7,8,9-tetrahydro(5H)pyrimido[5,4-b]azepine and 0.01 g of 10% Pd-C. In a hydrogen atmosphere, they were reacted at 50° C. for 4 hours. After filtering off the Pd-C, the filtrate was dried to solid to obtain 0.074 g of colorless crystals in a quantitative yield.

Melting point: 175°–178° C.

$^1$H-NMR spectrum (CDCl$_3$ solution, δ ppm): 2.2–2.5 (4H, m), 2.7–3.0 (2H, m), 2,94 (4H, t, J=4.5 Hz), 3.81 (4H, t, J=4.5 Hz), 7.00 (1H, br.s), 7.98 (1H, s).

Infrared absorption spectrum (nujol, cm$^{-1}$): 1685, 1600, 1505, 1350, 1255.

REFERENTIAL EXAMPLE 54

2-(4-Benzylpiperazino)-5,6-dihydro-7-ethyl-6-oxo(7H-)pyrrolo[2,3-d]pyrimidine

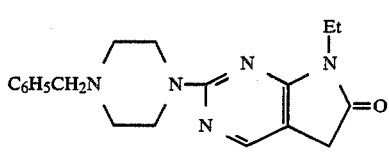

A mixture of 1.41 g (3.76 mmol, Referential Example 71) of ethyl 2-(4-benzylpiperazino)-4-chloropyrimidine-5-acetate, 5 ml of ethylamine and 20 ml of isopropanol was placed in a pressure vessel, in which they were heated at 120° C. for 2 hours. The solvent was then driven off under reduced pressure. The residue was added with water, followed by extraction with chloroform. After drying the organic layer with MgSO$_4$, it was concentrated. The residue was purified by silica gel column chromatography to obtain 0.58 of the above-identified compound (yield: 46%).

Melting point: 110°–113° C.

Infrared absorption spectrum (CDCl$_3$ solution, cm$^{-1}$): 1725, 1620, 1570.

$^1$H-NMR spectrum (CDCl$_3$ solution, δ ppm): 1.25 (3H, t, J=7.0 Hz), 2.49 (4H, t, J=5.2 Hz), 3.37 (2H, s), 3.54 (2H, s), 3.75 (2H, q, J=7.2 Hz), 3.83 (4H, t, J=5.2 Hz), 7.31 (5H, s), 7.89 (1H, s).

Similarly, the following two compounds were also obtained.

2-(4-Benzylpiperazino)-5,6-dihydro-7-methyl-6-oxo(7H)-pyrrolo[2,3-d]pyrimidine

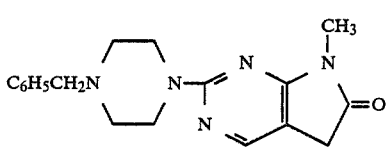

Yield: 72%.
Melting point: 172°–174° C.

$^1$H-NMR spectrum (CDCl$_3$ solution, δ ppm): 2.50 (4H, m), 3.18 (3H, s), 3.40 (2H, s), 3.54 (2H, s), 3.84 (4H, m), 7.34 (5H, m), 7.90 (1H, s).

Infrared absorption spectrum (KBr tablet, cm$^{-1}$): 1735, 1630, 1575, 1520, 1480, 1340, 1245.

2-(4-Benzylpiperazino)-5,6-dihydro-7-isopropyl-6-oxo(7H)pyrrolo[2,3-d]pyrimidine

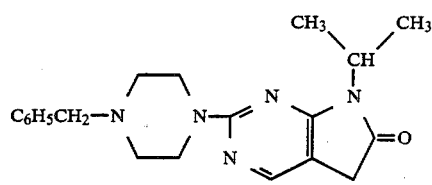

Yield: 36%.
Melting point: 125°–127° C.

$^1$H-NMR spectrum (CDCl$_3$ solution, δ ppm): 1.48 (6H, d, J=7 Hz), 2.50 (4H, m), 3.36 (2H, s), 3.56 (2H, s), 3.82 (4H, m), 4.62 (1H, sept., J=7 Hz), 7.33 (5H, m), 7.89 (1H, s).

Infrared absorption spectrum (KBr tablet, cm$^{-1}$): 1730, 1620, 1580, 1440, 1220, 1100.

REFERENTIAL EXAMPLE 55

5,6-Dihydro-7-ethyl-6-oxo-2-piperazino(7H)-pyrrolo[2,3-d]pyrimidine

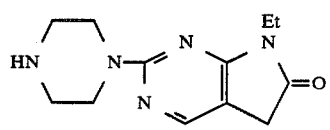

Using as a solvent 15 ml of ethanol which contained 0.12 ml of formic acid, 0.54 g (1.60 mmol, Referential Example 54) of 2-(4-benzylpiperazino)-5,6-dihydro-7-ethyl-6-oxo(7H)pyrrolo[2,3-d]pyrimidine was hydrogenated at normal pressure in the presence of 0.1 g of 10% Pd-C. After being refluxed for 4.5 hours, the catalyst was filtered off and ethanol was distilled off under reduced pressure. The residue was added with an aqueous solution of sodium carbonate, followed by extraction with chloroform. The organic layer was dried with MgSO$_4$ and then concentrated, thereby obtaining 0.36 g of the above-identified compound as an oily product (yield: 91%).

$^1$H-NMR spectrum (CDCl$_3$ solution, δ ppm): 1.27 (3H, t, J=7.0 Hz), 2.02 (1H, br.s), 2.92 (4H, t, J=5.2 Hz), 3.40 (2H, s), 3.80 (6H, m), 7.91 (1H, s).

The following compounds were also obtained in a similar manner.

5,6-Dihydro-7-methyl-6-oxo-2-piperazino(7H)pyrrolo[2,3-d]pyrimidine

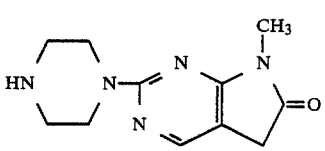

Yield: 70%.
Melting point: 145°–147° C.

¹H-NMR spectrum (CDCl₃ solution, δ ppm): 1.86 (1H, br.s), 2.94 (4H, m), 3.21 (3H, s), 3.43 (2H, s), 3.82 (4H, m), 7.93 (1H, s).

Infrared absorption spectrum (KBr tablet, cm⁻¹): 3340, 1738, 1630, 1580, 1450, 1105.

5,6-Dihydro-7-isopropyl-6-oxo-2-piperazino(7H)pyrrolo[2,3-d]pyrimidine

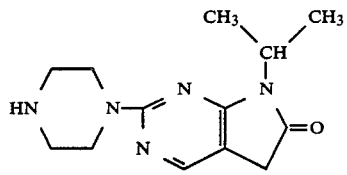

Yield: 83%.
Melting point: 113°–115° C.
¹H-NMR spectrum (CDCl₃ solution, δ ppm): 1.52 (6H, d, J=7 Hz), 2.08 (1H, br.s), 2.93 (4H, m), 3.40 (2H, s), 3.80 (4H, m), 4.65 (1H, sept., J=7 Hz), 7.47 (1H, s), 7.93 (1H, s).

Infrared absorption spectrum (neat, cm⁻¹): 3330, 1725, 1622, 1575, 1440, 1220, 1110.

REFERENTIAL EXAMPLE 56

8-Ethyl-5-oxo-2-piperazino-5,6,7,8-tetrahydropyrido[2,3-d]pyrimidine

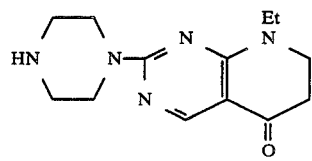

A mixture, which consisted of 2.5 g (11.3 mmol) of 8-ethyl-5-oxo-2-methylthio-5,6,7,8-tetrahydropyrido[2,3-d]pyrimidine (synthesized by the process described in Japanese Patent Laid-Open No. 18600/1978), 2.93 g (34.0 mmol) of anhydrous piperazine and 20 ml of dimethylsulfoxide, was heated at 120° C. for 3.5 hours and then at 140° C. for 6.5 hours. Dimethylsulfoxide was distilled off under reduced pressure. The residue was added with water, followed by extraction with chloroform. The organic layer was dried with MgSO₄ and then concentrated to obtain 3.08 g of the above-identified compound as an oily product (yield: 90%).

¹H-NMR spectrum (CDCl₃ solution, δ ppm): 1.20 (3H, t, J=7.2 Hz), 1.77 (1H, s), 2.61 (2H, dd, J=6.6, 6.7 Hz), 2.90 (4H, m), 3.59 (4H, m), 3.88 (4H, m), 8.59 (1H, s).

REFERENTIAL EXAMPLE 57

6,9-Dimethyl-2-methylthio-5-oxo-5,6,7,8-tetrahydro(9H)pyrimido[4,5-e]diazepine

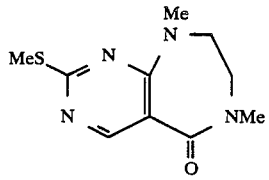

To a mixture of 4.58 ml (4.30 mmol) of N,N′-dimethylethylenediamine [synthesized by the process described in J. Am. Chem. Soc., 65, 350(1943)], 150 ml of EtOH and 2.51 g of Na₂CO₃, an ethanol solution (50 ml) of 5.0 g (21.5 mmol) of ethyl 4-chloro-2-methylthiopyrimidine-5-carboxylate was added dropwise over 50 minutes. After being refluxed for 13 hours, ethanol was distilled off under reduced pressure. The residue was added with water, followed by extraction with chloroform. The organic layer was dried and then concentrated. The residue was purified by silica gel column chromatography to obtain 3.55 g of the above-identified compound (yield: 69%).

Melting point: 153°–155° C.
¹H-NMR spectrum (CDCl₃ solution, δ ppm): 2.52 (3H, s), 3.13 (3H, s), 3.23 (3H, s), 3.63 (4H, ABqualt.), 8.72 (1H, s).

REFERENTIAL EXAMPLE 58

6,9-Dimethyl-2-(4-benzylpiperazino)-5-oxo-5,6,7,8-tetrahydro(9H)pyrimido[4,5-e]diazepine

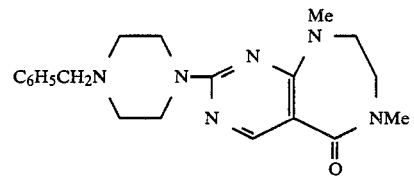

Continuously stirred at 140°–170° C. for 28 hours were 1.3 g (5.46 mmol) of 6,9-dimethyl-2-methylthio-5-oxo-5,6,7,8-tetrahydro(9H)pyrimido[4.5-e]diazepine and 4 g (22.69 mmol) of 1-benzylpiperazine. After cooling the reaction mixture, ethyl acetate was added to the reaction mixture and insoluble matter was filtered off. Then, the ethyl acetate solution was concentrated and the residue was purified by column chromatography to obtain 0.2 g of the intended product as reddish brown oil (yield: 10%).

¹H-NMR spectrum (CDCl₃ solution, δ ppm): 2.47 (4H, m), 3.11 (3H, s), 3.12 (3H, s), 3.55 (6H, m), 3.84 (4H, m), 7.32 (5H, m), 8.72 (1H, s).

REFERENTIAL EXAMPLE 59

6,9-Dimethyl-2-piperazino-5-oxo-5,6,7,8-tetrahydro(9H)pyrimido[4,5-e]diazepine

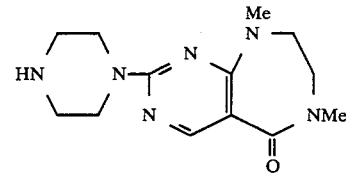

Dissolved in 10 ml of ethanol was 0.2 g (0.55 mmol) of 6,9-dimethyl-2-(4-benzylpiperazino)-5-oxo-5,6,7,8-tetrahydro(9H)pyrimido[4,5-e]diazepine, followed by an addition of 20 mg of 10% Pd-C. Under reflux, the reactant was hydrogenated at atmospheric pressure for 2 hours. After cooling the reaction mixture to room temperature, the catalyst was filtered off and the filtrate was concentrated under reduced pressure. The residue was purified by column chromatography to obtain 0.1 g of the intended product (yield: 67%).

$^1$H-NMR spectrum (CDCl$_3$ solution, δ ppm): 3.59 (6H, s), 3.27 (4H, m), 3.62 (4H, br.s), 4.20 (4H, m), 8.70 (1H, s).

REFERENTIAL EXAMPLE 60

Ethyl 4-amino-2-(4-benzylpiperazino)pyrimidine-5-carboxylate and 2-(4-benzylpiperazino)-5-cyano-4-hydroxypyrimidine

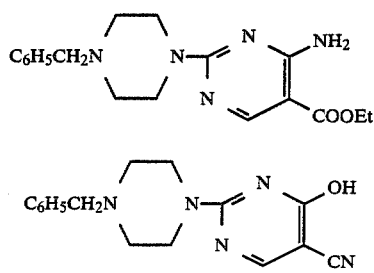

Mixed were 26.8 g of 1-amidino-4-benzylpiperazine sulfate and 133 ml of a 3% ethanol solution of sodium hydroxide, followed by an addition of 17.0 g of ethyl 2-cyano-3-ethoxyacrylate. After being refluxed for 5 hours, the reaction mixture was allowed to cool down. After distilling off ethanol from the reaction mixture, the residue was added with water and ethyl acetate. The resultant mixture was shaken. Precipitated colorless crystals of 2-(4-benzylpiperazino)-5-cyano-4-hydroxypyrimidine were collected by filtration, washed with water and then dried, thereby obtaining 7.4 g of 2-(4-benzylpiperazino)-5-cyano-4-hydroxypyrimidine (yield: 25%).

Melting point: 243°–244° C.

$^1$H-NMR spectrum (CDCl$_3$ solution, δ ppm): 2.45 (4H, m), 3.45 (2H, m), 3.50 (2H, s), 3.73 (2H, m), 7.32 (5H, m), 8.12 (1H, s).

The filtrate was shaken, and the organic layer was dried and concentrated to obtain solid matter. The solid matter was added with ether. After removing insoluble matter, ether was distilled off to obtain 11.2 g of ethyl 4-amino-2-(4-benzylpiperazino)pyrimidine-5-carboxylate as light yellowish crystals.

Melting point: 224°–245° C.

$^1$H-NMR spectrum (CDCl$_3$ solution, δ ppm): 1.34 (3H, t, J=7 Hz), 2.46 (4H, m), 3.53 (2H, s), 3.86 (4H, m), 4.27 (2H, q, J=7 Hz), 7.32 (5H, m), 8.63 (1H, s).

REFERENTIAL EXAMPLE 61

Ethyl 4-acetylamino-2-(4-benzylpiperazino)pyrimidine-5-carboxylate

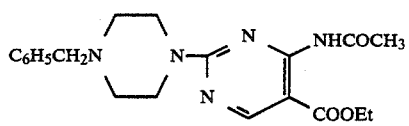

In acetic anhydride, 1.00 g of ethyl 4-amino-2-(4-benzylpiperazino)pyrimidine-5-carboxylate (the compound synthesized in Referential Example 60) was refluxed for 1 hour. After allowing the reaction mixture to cool down, acetic anhydride was distilled off and the resulting viscous oil was purified by silica gel column chromatography to obtain 0.68 g of the above-identified compound (yield: 61%).

$^1$H-NMR spectrum (CDCl$_3$ solution, δ ppm): 1.36 (3H, t, J=7 Hz), 2.48 (3H, s), 2.52 (4H, m), 3.56 (2H, s), 3.92 (4H, m), 4.33 (2H, q, J=7 Hz), 7.33 (5H, m), 8.78 (1H, s).

REFERENTIAL EXAMPLE 62

Ethyl 2-(4-benzylpiperazino)-4-hydroxypyrimidine-5-carboxylate

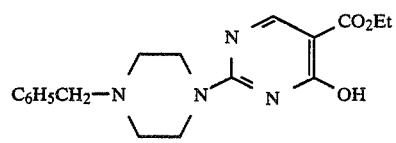

An ethanol solution of 25.2 g of sodium hydroxide was added with 160 g (0.60 mol) of 1-amidino-4-benzylpiperazine sulfate, followed by a dropwise addition of 129.4 g (0.60 mol) of diethyl ethoxymethylenemalonate over 20 minutes. After being refluxed for 5.5 hours, the reaction mixture was cooled and the precipitated crystals were collected by filtration. The thus-obtained crystals were washed with water and then dried, thereby obtaining 131.4 g of the above-identified compound (yield: 64%).

Melting point: 151°–153° C.

$^1$H-NMR spectrum (CDCl$_3$ solution, δ ppm): 1.36 (3H, t, J=7 Hz), 2.49 (4H, m), 3.54 (2H, s), 3.93 (4H, m), 4.35 (2H, q, J=7 Hz), 7.31 (5H, s), 8.63 (1H, s).

REFERENTIAL EXAMPLE 63

Ethyl 2-(4-benzylpiperazino)-4-chloropyrimidine-5-carboxylate

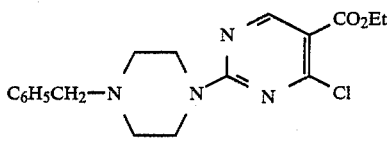

A mixture of 130.0 g (0.38 mol) of ethyl 2-(4-benzylpiperazino)-4-hydroxypyrimidine-5-carboxylate (the compound snythesized in Referential Example 62) and 390 ml of thionyl chloride was refluxed for 10 hours. After adding 600 ml of toluene, the resultant mixture was distilled to remove excess thionyl chloride. The reaction mixture was ice-cooled and was then added with an aqueous solution of sodium hydroxide to render it alkaline. It was then extracted with chloroform. After drying the chloroform layer with MgSO$_4$, chloroform was distilled off under reduced pressure to obtain 120.2 g of the above-identified compound as an oily product (yield: 88%).

$^1$H-NMR spectrum (CDCl$_3$ solution, δ ppm): 1.36 (3H, 5, J=7 Hz), 2.50 (4H, m), 3.56 (2H, br.s), 3.92 (4H, m), 4.32 (2H, q, J=7 Hz), 7.35 (5H, s), 8.79 (1H, s).

REFERENTIAL EXAMPLE 64

Ethyl 2-(4-benzylpiperazino)-4-ethylaminopyrimidine-5-carboxylate

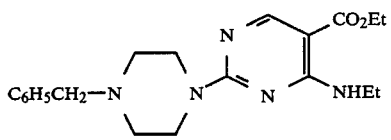

To a mixture of 101.3 g (0.28 mol) of ethyl 2-(4-benzylpiperazino)-4-chloropyrimidine-5-carboxylate (the compound synthesized in Referential Example 63) and 590 ml of chloroform, 72.3 g (1.12 mol) of a 70% aqueous solution of ethylamine was added dropwise over 15 minutes. The resultant mixture was stirred at room temperature for 2 hours. The reaction mixture was added with water, followed by extraction with chloroform. After drying the chloroform layer with $MgSO_4$, chloroform was distilled off to obtain 103.5 g of the above-identified compound as an oily product (yield: about 100%).

$^1$H-NMR spectrum ($CDCl_3$ solution, δ ppm): 1.22 (3H, t, J=7 Hz), 1.32 (3H, t, J=7 Hz), 2.47 (4H, m), 3.46 (2H, d, q, J=5, 7 Hz), 3.54 (2H, s), 3.88 (4H, m), 4.25 (2H, q, J=7 Hz), 7.31 (5H, s), 8.00 (1H, br.t, J=5 Hz), 8.58 (1H, s).

Each of the following compounds was also prepared in a similar manner.

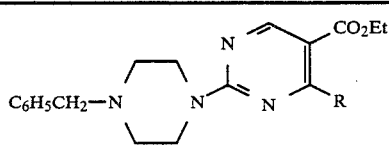

| R | |
|---|---|
| NHCH$_3$ (m.p. 71–74° C.) | (synthesized from the compound of Ref. Ex. 63) |
| NHPr$^i$ | (synthesized from the compound of Ref. Ex. 63) |
| N(CH$_3$)$_2$ | (synthesized from the compound of Ref. Ex. 63) |
| NEt$_2$ | (synthesized from the compound of Ref. Ex. 63) |

REFERENTIAL EXAMPLE 65

Methyl 2-(4-benzylpiperazino)-4-ethylaminopyrimidine-5-carboxylate

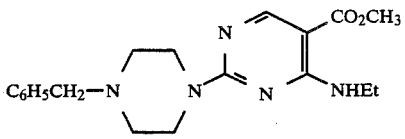

To a methanol solution (10 ml) containing 0.24 g (4.44 mmol) of sodium methoxide, was added a methanol solution (10 ml) of 0.80 g (2.17 mmol) of ethyl 2-(4-benzylpiperazino)-4-ethylaminopyrimidine-5-carboxylate (the compound synthesized in Referential Example 64). The resultant mixture was refluxed for 2 hours. Methanol was distilled off under reduced pressure. Water was added to the residue, followed by extraction with ethyl acetate. The organic layer was dried with $MgSO_4$ and ethyl acetate was distilled off under reduced pressure, thereby obtaining 0.75 g of the above-identified compound as an oily product (yield: 97%).

$^1$H-NMR spectrum ($CDCl_3$ solution, δ ppm): 1.22 (3H, t, J=7 Hz), 2.48 (4H, m), 3.47 (2H, d, q, J=5, 7 Hz), 3.54 (2H, s), 3.79 (3H, s), 3.83 (4H, m), 7.31 (5H, s), 7.96 (1H, br. t, J=5 Hz), 8.56 (1H, s).

The following compounds were also synthesized in a similar manner.

| Structural formula | |
|---|---|
| 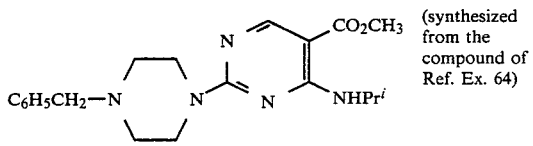 | (synthesized from the compound of Ref. Ex. 64) |
| 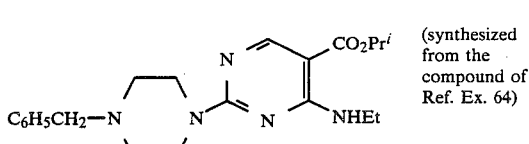 | (synthesized from the compound of Ref. Ex. 64) |

REFERENTIAL EXAMPLE 66

Methyl 2-(4-benzylpiperazino)-4-methoxypyrimidine-5-carboxylate

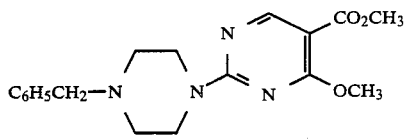

To a methanol solution (50 ml) of 1.88 g (34.8 mmol) of sodium methoxide, a methanol solution (40 ml) of 10.1 g (28.0 mmol) of ethyl 2-(4-benzylpiperazino)-4-chloropyrimidine-5-carboxylate (the compound synthesized in Referential Example 63) was added dropwise over 10 minutes. The resultant mixture was stirred at room temperature for 1 hour. Methanol was distilled off under reduced pressure and water was added, followed by extraction with chloroform. After drying the chloroform layer with $MgSO_4$, chloroform was distilled off under reduced pressure and the residue was recrystallized from methanol-ethyl acetate to obtain 7.9 g of the above-identified compound (yield: 79%).

Melting point: 135°–138° C.

$^1$H-NMR spectrum ($CDCl_3$ solution, δ ppm): 2.49 (4H, m), 3.54 (2H, s), 3.82 (3H, s), 3.90 (4H, m), 3.97 (3H, s), 7.32 (5H, s), 8.71 (1H, m).

REFERENTIAL EXAMPLE 67

2-(4-Benzylpiperazino)-4-ethylaminopyrimidine-5-carboxylic acid

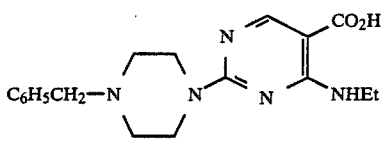

After refluxing for 1 hour a mixture of 106.4 g (0.29 mol) of ethyl 2-(4-benzylpiperazino)-4-ethylaminopyrimidine-5-carboxylate (the compound synthesized in Referential Example 64), 38.0 g (0.58 mol) of a 85% aqueous solution of potassium hydroxide, 100 ml of water and 400 ml of ethanol, ethanol was distilled off under reduced pressure. The residue was added with water and then neutralized with hydrochloric acid. The precipitated crystals were collected by filtration and were then dried to obtain 80.3 g of the above-identified compound (yield: 82%).

Melting point: 158°–160° C.

$^1$H-NMR spectrum (DMSO-$d_6$ solution, δ ppm): 1.18 (3H, t, J=7 Hz), 2.66 (4H, m), 3.44 (2H, d, q, J=5, 7 Hz), 3.75 (2H, s), 3.91 (4H, m), 7.35 (5H, s), 8.19 (1H, br. t, J=5 Hz), 8.45 (1H, s).

Each of the following compounds was also synthesized in a similar manner.

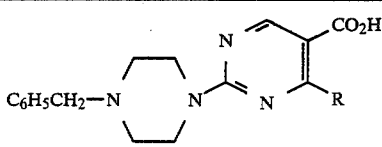

| R | m.p. | |
|---|---|---|
| NH$_2$ | 158–160° C. | (synthesized from the compound of Ref. Ex. 60) |
| NHCH$_3$ | 184–186° C. | (synthesized from the compound of Ref. Ex. 64) |
| NHPr$^i$ | | (synthesized from the compound of Ref. Ex. 64) |
| OCH$_3$ | 208–210° C. | (synthesized from the compound of Ref. Ex. 66) |
| SCH$_3$ | | (synthesized from the compound of Ref. Ex. 76) |

REFERENTIAL EXAMPLE 68

2-(4-Benzylpiperazino)-4-ethylaminopyrimidine-5-carboxylic acid diethylamide

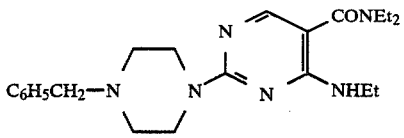

A mixture of 0.5 g (1.46 mmol) of 2-(4-benzylpiperazino)-4-ethylaminopyrimidine-5-carboxylic acid (the compound synthesized in Referential Example 67) and 20 ml of chloroform was added with 0.2 ml (1.43 mmol) of triethylamine, followed by a further addition of 0.22 ml (3.02 mmol) of thionyl chloride. The resultant mixture was stirred at room temperature for 1 hour. After adding 1.0 ml (9.67 mmol) of diethylamine and stirring the resultant mixture for 1 hour, water was added. The resultant mixture was extracted with chloroform. After drying the chloroform layer with MgSO$_4$, the solvent was distilled off under reduced pressure and the residue was purified by silica gel column chromatography to obtain 0.37 g of the above-identified compound (yield: 64%).

$^1$H-NMR spectrum (CDCl$_3$ solution, δ ppm): 1.20 (3H, t, J=7 Hz), 1.21 (3H, t, J=7 Hz), 1.25 (3H, t, J=7 Hz), 2.48 (4H, m), 3.45 (6H), 3.54 (2H, s), 3.84 (4H, m), 6.98 (1H, br. t, J=5 Hz), 7.32 (5H, s), 7.90 (1H, s).

Each of the following compounds was also synthesized in a similar manner.

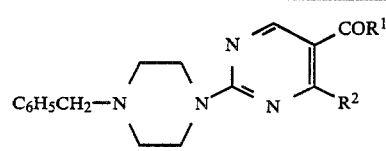

| R$^1$ | R$^2$ | m.p. | Ref. Ex. No. of corres. starting compound |
|---|---|---|---|
| NHCH$_3$ | NHCH$_3$ | | 67 |
| NHEt | NH$_2$ | 163–164° C. | 67 |
| NHET | NHET | | 67 |
| N(CH$_3$)$_2$ | NHCH$_3$ | | 67 |
| N(CH$_3$)$_2$ | NHEt | | 67 |
| NEt$_2$ | NH$_2$ | 116–120° C. | 67 |
| NEt$_2$ | NHCH$_3$ | | 67 |
| NEt$_2$ | NHPr$^i$ | | 67 |
| NEt$_2$ | OCH$_3$ | | 67 |
| NEt$_2$ | SCH$_3$ | | 67 |
| NPr$_2{}^n$ | NHEt | | 67 |

REFERENTIAL EXAMPLE 69

2-Piperazino-4-ethylaminopyrimidine-5-carboxylic acid diethylamide

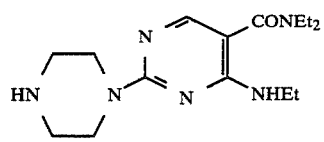

Using 20 ml of ethanol and 0.1 ml of 99% formic acid as solvents and 0.1 g of 10% Pd-C as a catalyst, 0.33 g (0.83 mmol) of 2-(4-benzylpiperazino)-4-ethylaminopyrimidine-5-carboxylic acid diethylamide (the compound synthesized in Referential Example 68) was refluxed for 1 hour for its hydrodecomposition. The catalyst was filtered off and the solvents were distilled off under reduced pressure, thereby obtaining 0.26 g of the above-identified compound as an oily product (yield: about 100%).

$^1$H-NMR spectrum (CDCl$_3$ solution, δ ppm): 1.23 (9H), 3.36 (4H, m), 4.47 (6H), 4.21 (4H, m), 7.05 (1H, br. t, J=5 Hz), 7.27 (5H, s), 7.90 (1H, s).

Each of the following compounds was also obtained in a similar manner.

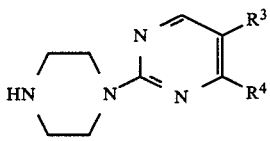

| $R^3$ | $R^4$ | m.p. | Ref. Ex. No. of corres. starting compound |
|---|---|---|---|
| $CO_2CH_3$ | NHEt | 190–192° C. | 65 |
| $CO_2CH_3$ | $NHPr^i$ | | 65 |
| $CO_2Et$ | OH | 221–223° C. | 62 |
| $CO_2Et$ | $NH_2$ | 208–210° C. | 60 |
| $CO_2Et$ | $NHCH_3$ | | 64 |
| $CO_2Et$ | $N(CH_3)_2$ | | 64 |
| $CO_2Et$ | NHEt | | 64 |
| $CO_2Et$ | $NEt_2$ | | 64 |
| $CO_2Et$ | $NHPr^i$ | | 64 |
| $CO_2Et$ | $NHCOCH_3$ | 232–233° C. | 61 |
| $CO_2Pr^i$ | NHEt | | 65 |
| $CONHCH_3$ | $NHCH_3$ | | 68 |
| CONHEt | $NH_2$ | | 68 |
| CONHEt | NHEt | | 68 |
| $CON(CH_3)_2$ | $NHCH_3$ | | 68 |
| $CON(CH_3)_2$ | NHEt | | 68 |
| $CONEt_2$ | $NH_2$ | 248–250° C. | 68 |
| $CONEt_2$ | $NHCH_3$ | | 68 |
| $CONEt_2$ | $NHPr^i$ | | 68 |
| $CONEt_2$ | $OCH_3$ | | 68 |
| $CONEt_2$ | $SCH_3$ | | 68 |
| $CONPr_2^n$ | NHEt | | 68 |
| CN | OH | | 60 |
| $CH_2CONHEt$ | NHEt | | 72 |

REFERENTIAL EXAMPLE 70

Ethyl 2-(4-benzylpiperazino)-4-hydroxypyrimidine-5-acetate

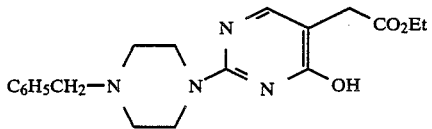

Added to an ethanol solution of sodium ethoxide, which had been prepared from 0.57 g (24.8 mmol) of sodium and 30 ml of EtOH, was 6.61 g (24.7 mmol) of 1-amidino-4-benzylpiperazine sulfate, followed by a dropwise addition of an ethanol solution (10 ml) of 5.0 g (24.7 mmol) of ethyl 2-formylsuccinate [the compound described in Ann. 363, 340] over 15 minutes. The resultant mixture was then refluxed for 4.5 hours. After cooling the reaction mixture, crystals were collected by filtration and then washed with water to obtain 3.65 g of the above-identified compound (yield: 41%).

Melting point: 203°–205° C.

$^1$H-NMR spectrum (CDCl$_3$ solution, δ ppm): 1.17 (3H, t, J=7 Hz), 2.50 (4H, m), 3.26 (2H, s), 3.54 (2H, s), 3.71 (4H, m), 4.01 (2H, q, J=7 Hz), 7.31 (5H, s), 7.66 (1H, s).

REFERENTIAL EXAMPLE 71

Ethyl 2-(4-benzylpiperazino)-4-chloropyrimidine-5-acetate

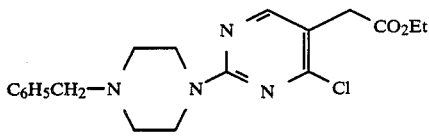

A mixture of 3.0 g (8.00 mmol) of ethyl 2-(4-benzylpiperazino)-4-hydroxypyrimidine-5-acetate (the compound synthesized in Referential Example 70) and 50 ml of toluene was added with 1.12 ml (8.03 mmol) of triethylamine and 0.90 ml (9.66 mmol) of phosphorus oxychloride. The resultant mixture was stirred at room temperature for 2 hours and was then refluxed for 1 hour. The mixture was poured in water, followed by extraction with chloroform. The chloroform layer was dried with MgSO$_4$ and the solvent was distilled off under reduced pressure. The residue was purified by alumina column chromatography to obtain 1.85 g of the above-identified compound as an oily product (yield: 59%).

$^1$H-NMR spectrum (CDCl$_3$ solution, δ ppm): 1.25 (3H, t, J=7 Hz), 2.48 (4H, m), 3.53 (4H, s), 3.81 (4H, m), 4.17 (2H, q. J=7 Hz), 7.31 (5H, s), 8.10 (1H, s).

REFERENTIAL EXAMPLE 72

2-(4-Benzylpiperazino)-4-ethylaminopyrimidine-5-acetic acid ethylamide

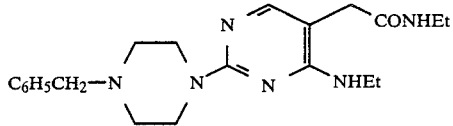

A mixture of 1.41 g (3.76 mmol) of ethyl 2-(4-benzylpiperazino)-4-chloropyrimidine-5-acetate [the compound synthesized in Referential Example 71], 5 ml of ethylamine and 20 ml of isopropanol was placed in a pressure vessel and was then heated at 120° C. for 2 hours. Thereafter, the solvent was driven off under reduced pressure and water was added, followed by extraction with chloroform. The organic layer was dried with MgSO$_4$ and then concentrated. The residue was purified by silica gel column chromatography, thereby obtaining 0.58 g of the above-identified compound (yield: 40%).

Melting point: 103°–107° C.

$^1$H-NMR spectrum (CDCl$_3$ solution, δ ppm): 1.07 (3H, t, J=7 Hz), 1.21 (3H, t, J=7 Hz), 2.48 (4H, m), 3.16 (2H, s), 2.20–2.50 (4H), 3.54 (2H, s), 7.32 (5H, s), 7.59 (1H, s).

REFERENTIAL EXAMPLE 73:

2-Piperazino-6,7-dimethoxyquinazoline

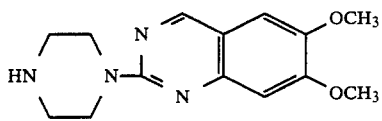

Refluxed for 2 hours in isoamyl alcohol (15 ml) were 0.63 g of 2-chloro-6,7-dimethoxyquinazoline (synthesized by the method described in Japanese Patent Laid-Open No. 36390/1972) and 0.72 g of anhydrous piperazine. Isoamyl alcohol was thereafter distilled off under reduced pressure, followed by extraction with 2N—NaOH and chloroform. The chloroform layer was washed with saturated saline and then dried with anhydrous magnesium sulfate. Chloroform was distilled off under reduced pressure to obtain 0.7 g of the intended product (yield: 91%).

The following compound was also synthesized in a similar manner.

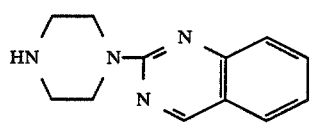

REFERENTIAL EXAMPLE 74

2-Chloro-5-methyl-4-methylthio-5,6,7,8-tetrahydrobenzo[1]thieno[2,3-d]pyrimidine

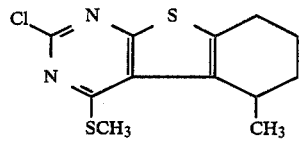

To 2.65 g of 2,4-dichloro-5-methyl-5,6,7,8-tetrahydrobenzo[1]thieno[2,3-d]pyrimidine [synthesized by the process described in M. Robba, P. Touzot and R. M. Riquelme, C. R. Acd. Sci. Ser. C., 276(1), 93(1973)] and 50 ml of acetone, a MeOH solution (15 ml) of 0.68 g of MeSNa which was prepared on the side was added. The resultant mixture was stirred at room temperature for 1 hour. The solvent was distilled off under reduced pressure, followed by extraction with water and chloroform. The chloroform layer was dried with magnesium sulfate and chloroform was distilled off under reduced pressure. The residue was purified by column chromatography to obtain 0.9 g of the intended product (yield: 31%).

REFERENTIAL EXAMPLE 75

5-Methyl-4-methylthio-2-piperazino-5,6,7,8-tetrahydrobenzo[1]thieno[2,3-d]pyrimidine

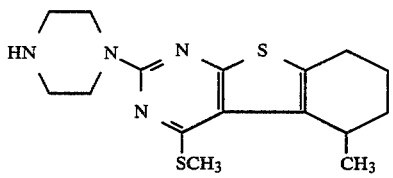

In methylene chloride, 0.9 g of the 2-chloro-5-methyl-4-methylthio-5,6,7,8-tetrahydrobenzo[1]thieno[2,3-d]pyrimidine obtained in Referential Example 74, 0.35 g of 1-piperazinecarboxyaldehyde and 0.6 g of triethylamine were reacted for 3 hours. The reaction mixture was poured in water, followed by extraction with methylene chloride. The methylene chloride layer was dried with anhydrous magnesium sulfate and was then concentrated under reduced pressure. The residue was added with 10 ml of HCl-saturated ethanol and the resultant mixture was stirred at 80° C. for 2 hours. After concentration of the reaction mixture, the concentrate was extracted with chloroform. The chloroform layer was washed with 2N—NaOH and then with saturated saline. The chloroform layer was dried with anhydrous magnesium sulfate and was then concentrated. The residue was purified by column chromatography to obtain 0.6 g of the intended product (yield: 58%).

REFERENTIAL EXAMPLE 76

2-(4-Benzylpiperazino)-5-ethoxypyrido[4,3-d]pyrimidine

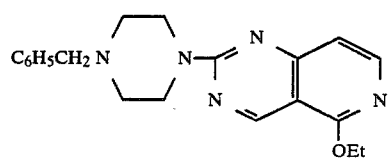

Phosphorus oxychloride (5 ml) was added to 0.56 g (1.74 mmol) of 2-(4-benzyl-1-piperazino)-5-oxopyrido[4,3-d]pyrimidine. They were reacted at 110° C. for 1 hour. The reaction mixture was then added dropwise to a mixture of ice, sodium hydrogencarbonate and chloroform. After decomposition, the oil layer was washed with saturated saline and then dried with sodium sulfate. After distilling off chloroform under reduced pressure, an ethanol solution (50 ml) of 1.48 g (21.7 mmol) of sodium ethoxide was added at 0° C. The resultant mixture was heated under reflux for 1 hour. After distilling off ethanol under reduced pressure, water was added, followed by extraction with ethanol. The oil layer was washed with saturated saline and then dried with sodium sulfate. Chloroform was distilled off under reduced pressure to obtain 0.55 g of light yellowish oil (yield: 90%).

$^1$H-NMR spectrum (CDCl$_3$ solution, δ ppm): 1.47 (3H, t, J=8 Hz), 2.54 (2H, m), 3.57 (2H, s), 4.00 (2H, m), 4.31 (2H, q. J=8 Hz), 6.87 (1H, d, J=7 Hz), 7.34 (5H, s), 8.04 (1H, d, J=7 Hz), 9.24 (1H, s).

REFERENTIAL EXAMPLE 77

5-Ethoxy-2-piperazinopyrido[4,3-d]pyrimidine

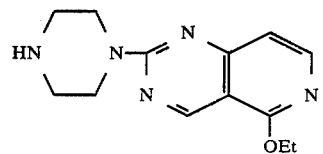

In a hydrogen atmosphere, a mixture of 0.5 g (1.43 mmol) of the 2-(4-benzylpiperazino)-5-ethoxypyrido[4,3-d]pyrimidine obtained in Referential Example 76, 0.05 g of 10% Pd-C and 30 ml of ethanol was heated under reflux for 5 hours. After cooling, the catalyst was filtered off and washed with ethanol. The solvent was distilled off from the mother liquor. Upon recrystallization from ethyl acetate, 0.3 g of white crystals were obtained (yield: 80%).

Melting point: 196°–198° C.

Infrared absorption spectrum (KBr tablet, cm$^{-1}$): 3400, 2860, 2790, 1615, 1575, 1560, 1500, 1425, 1330, 1270, 830.

$^1$H-NMR spectrum (CDCl$_3$ solution, δ ppm): 1.30 (3H, t, J=8 Hz), 3.35 (2H, m), 4.40 (2H, m), 4.56 (2H, q, J=8 Hz), 6.93 (1H, d, J=7 Hz), 8.14 (1H, d, J=7 Hz), 9.31 (1H, s).

REFERENTIAL EXAMPLE 78

2-(4-Benzylhomopiperazino)-4-methylpyrimidine-5-carboxylic acid

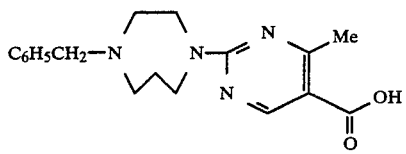

Dissolved in 10 ml of isoamyl alcohol were 4 g of ethyl 4-methyl-2-methylthiopyrimidine-5-carboxylate [synthesized by the process described in Acta. Chim. Sinia., 23, 145(1957)] and 5.39 g of N-benzylhomopiperazine (synthesized by the process described in Japanese Patent Laid-Open No. 18488/1975). They were reacted for 5 hours while being heated under reflux. Thereafter, isoamyl alcohol and excess N-benzylhomopiperazine were distilled off under reduced pressure. The residue was added with 3.4 g of potassium hydroxide and 40 ml of ethanol. While being heated under reflux, they were reacted for 2.5 hours. After cooling the reaction mixture, ethanol was distilled off. The residue was dissolved in water and the resultant aqueous solution was adjusted to pH 3-4 with conc. hydrochloric acid. By filtration, 2.70 g of the intended product was obtained as crystals. Yield: 44% (based on 5-ethoxycarbonyl-6-methyl-2-methylthiopyrimidine).

Melting point: 77°-80° C.

$^1$H-NMR spectrum (DMSO-d$_6$ solution, δ ppm): 2.20 (2H, m), 2.60 (3H, s), 3.32 (8H, m), 4.28 (2H, s), 7.46 (5H, s), 8.76 (1H, s).

g of the intended product (melting point: 255°-259° C.; yield: 83%).

$^1$H-NMR spectrum (DMSO-d$_6$ solution, δ ppm): 1.25 (3H, t, J=7 Hz), 3.88 (16H, m), 6.27 (1H, d, J=8 Hz), 6.79 (1H, s), 7.12 (2H, br. s), 7.44 (1H, s), 7.72 (1H, d, J=8 Hz), 9.08 (1H, s).

Dissolved in methanol-chloroform was 33.4 g of the free base obtained in the above preparation process, followed by an addition of equimolar amount of HCl in ethanol. Thereafter, excess hydrogen chloride and solvent were distilled off to obtain 36 g of the hydrochloride of the above-identified compound.

Melting point: 273°-275° C.

$^1$H-NMR spectrum (DMSO-d$_6$ solution, δ ppm): 1.22 (3H, t, J=7 Hz), 3.84 (3H, s), 4.02 (10H, m), 6.22 (1H, d, J=8 Hz), 7.62 (1H, s), 7.67 (1H, d, J=8 Hz), 7.68 (1H, s), 8.54 (1H, br. s), 8.90 (1H, br. s), 9.03 (1H, s), 12.42 (1H, br. s).

IR spectrum (KBr tablet, cm$^{-1}$): 1635, 1620, 1590, 1570, 1245.

Each of the following acid addition salts was synthesized in a similar manner.

| Acetate | m.p. 255-256° C. |
|---|---|
| Fumarate | m.p. 242-244° C. |
| Maleate | m.p. 242-244° C. |
| Benzoate | m.p. 224-226° C. |
| Citrate | m.p. 222-226° C. |
| Tartrate | m.p. 237-241° C. |
| Hydrogenbromide | m.p. 249-252° C. |
| Methanesulfonate | m.p. >300° C. |
| Sulfate | m.p. 278-280° C. |
| Phosphate | m.p. 292-295° C. |

EXAMPLE 2

4-Amino-6,7-dimethoxy-2-(4-(4-ethylamino-5-methoxycarbonylpyrimidine-2-yl)piperazino)quinazoline hydrochloride

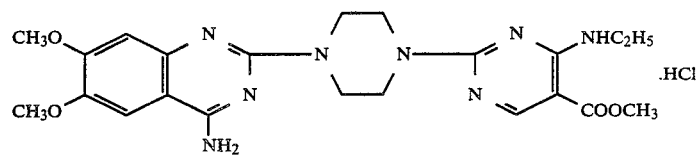

In 20 ml of n-butanol, 1.1 g of 4-amino-2-chloro-6,7-dimethoxyquinazoline and 1.22 g of the 4-ethylamino-5-methoxycarbonyl-2-piperazinopyrimidine obtained in Referential Example 69 were refluxed for 4 hours. After allowing the reaction mixture to cool down, the precipitated crystals were collected by filtration. The crystals were washed with ethanol and then with ethyl acetate to obtain 1.8 g of the above-identified compound (yield: 78%).

Melting point: 269°-270° C. (decomposed).

EXAMPLE 1

4-Amino-6,7-dimethoxy-2-(4-(5,6-dihydro-6-ethyl-5-oxopyrido[4,3-d]pyrimidin-2-yl)piperazino)quinazoline and acid addition salts thereof

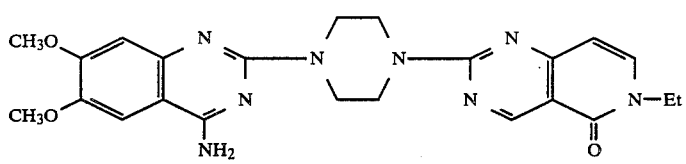

In 600 ml of isoamyl alcohol as a solvent, 24.5 g of 4-amino-2-chloro-6,7-dimethoxyquinazoline, 27.8 g of the 5,6-dihydro-6-ethyl-5-oxo-2-piperazinopyrido[4,3-d]pyrimidine and 10.8 g of triethylamine were refluxed for 4 hours. After allowing the reaction mixture to cool down, the precipitated crystals were collected by filtration. The crystals were then recrystallized from a mixed solvent of methanol and dichloromethane to obtain 39.4

¹H-NMR spectrum (DMSO-d₆ solution, δ ppm): 1.2 (3H, t, J=7 Hz), 3.78 (3H, s), 3.86 (3H, s), 3.92 (3H, s), 3.97 (8H, m), 7.43 (1H, s), 7.74 (1H, s), 8.54 (1H, s).

EXAMPLES 3 TO 80

Following the procedure of Example 1 or 2, a variety of compounds of this invention were prepared. Results are summarized in Table 1, in which Preparation Processes A and B correspond to Examples 1 and 2 respectively. In addition, the number of one of the Referential Example is given in parenthesis under each Preparation Process. This number indicates the Referential Example in which the corresponding starting material was prepared.

TABLE 1

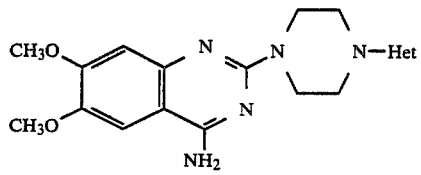

| Ex. No. | Het | Prep'n (Ref. Ex. No.) | Yield (%) | Isolated form (m.p. °C.) | ¹H—NMR spectrum, δ ppm | IR spectrum (cm⁻¹) |
|---|---|---|---|---|---|---|
| 3 | (pyrimidinyl-pyridinone, NH) | B (14) | 50 | HCl salt >300 | CDCl₃—CD₃OD 3.98(3H,s),4.04(3H,s), 4.08(8H,m),6.40(1H,d,J=8Hz),7.32(1H,s),7.34 (1H,s),7.40(1H,d,J=8Hz), 9.24(1H,s). | KBr tablet 3425,3155,1645, 1625,1578,1496, 1432,1250,1238, 1109,984. |
| 4 | (pyrimidinyl-pyridinone, NCH₃) | B (14) | 79 | HCl salt 277–278 | DMSO—d₆ 3.44(3H,s),3.86(3H,s), 3.92(3H,s),4.05(8H,m), 6.31(1H,d,J=8Hz),7.50 (1H,s),7.76(1H,s),7.80 (1H,d,J=8Hz),8.78(2H,br.s), 9.12(1H,s) | |
| 5 | (pyrimidinyl-pyridinone, NPrⁿ) | B (14) | 97 | HCl salt 269 (dec'd) | DMSO—d₆ 0.89(3H,t,J=7Hz),1.48– 1.80(2H,m),3.40(2H,t, J=7Hz),3.89(3H,s),3.91 (3H,s),4.08(8H,br.s),6.27 (1H,d,J=8Hz),7.72(1H,s), 7.78(1H,s),7.79(1H,d,J= 8Hz),8.68(2H,br.s),9.07 (1H,s),12.61(1H,br.s). | KBr tablet 3330,3180,1642, 1628,1596,1576, 1506,1440,1248. |
| 6 | (pyrimidinyl-pyridinone, NPrⁱ) | B (14) | 68 | HCl salt 276 (dec'd) | DMSO—d₆ 1.33(6H,d,J=8Hz),3.87(3H, s),3.91(3H,s),4.07(8H, br.s),5.07(1H,septet,J= 8Hz),6.35(1H,d,J=9Hz), 7.65(1H,s),7.77(1H,s), 7.86(1H,d,J=9Hz),8.77 (2H,br.s),9.11(1H,s). | KBr tablet 3340,3170,1642, 1598,1576,1514, 1442,1246. |
| 7 | (pyrimidinyl-pyridinone, NCH₂CH₂OH) | B (16) | 39 | HCl salt 260–262 (dec'd) | DMSO—d₆ 3.7(4H,br.),3.86(3H,s), 3.90(3H,s),4.05(8H,br.), 6.30(1H,d,J=7Hz),7.58 (1H,s),7.70(1H,d,J= 7Hz),7.75(1H,s),8.8(2H), 9.10(1H,s). | KBr tablet 3320,3170,1620, 1590,1570. |
| 8 | (pyrimidinyl-pyridinone, NCH₂CH₂OCH₃) | B (14) | 14 | HCl salt 274 | DMSO—d₆ 3.30(3H,s),3.88(3H,s), 3.91(3H,s),4.04(10H,m), 6.50(1H,d,J=7Hz),7.40– 7.68(3H,m),9.10(1H,s). | Nujol 3300,3100,1640, 1376,1107. |
| 9 | (pyrimidinyl-pyridinone, NC₆H₅) | B (14) | 57 | HCl salt 291–293 (dec'd) | DMSO—d₆ 3.85(3H,s),3.90(3H,s), 4.04(8H,br.s),6.39(1H,d, J=8Hz),7.3–7.6(5H),7.6– 7.9(3H),8.6(2H,br.s), 9.13(1H,s). | KBr tablet 3180,1630,1580, 1500. |

TABLE 1-continued

Structure: 3,4-dimethoxyphenyl group with C(=N-)(NH2) amidine, N connected to C(=N-piperazinyl-N-Het)

| Ex. No. | Het | Prep'n (Ref. Ex. No.) | Yield (%) | Isolated form (m.p. °C.) | ¹H—NMR spectrum, δ ppm | IR spectrum (cm⁻¹) |
|---|---|---|---|---|---|---|
| 10 | [pyrimidine with N—CH₂C₆H₅ pyridone] | B (14) | 57 | HCl salt 269–270 (dec'd) | CDCl₃ 3.86(3H,s),3.89(3H,s), 4.04(8H,m),5.11(2H,s),6.34 (1H,d,J=7Hz),7.32(5H,s), 7.62(1H,s),7.76(1H,s), 7.88(1H,d,J=7Hz),8.80(2H, br.s),9.11(1H,s). | KBr tablet 3340,3200,1640, 1620,1595,1570. |
| 11 | [pyrimidine with N-cyclopropyl pyridone] | B (14) | 30 | Free base / HCl salt m.p. 263–265 (dec'd) | CDCl₃ 1.07(4H,m),3.24(1H,m), 3.86(14H,m),5.38(2H,br.s), 6.27(1H,d,J=8Hz),6.88 (1H,s),6.94(1H,s),7.33 (1H,d,J=8Hz),9.26(1H,s). | |
| 12 | [pyrimidine with CH₃, NEt pyridone] | B (14) | 85 | HCl salt 280–292 (dec'd) | DMSO—d₆ 1.23(3H,t,J=7Hz),2.15 (3H,d,J=0.9Hz),3.85(3H, s),3.91(3H,s),3.8–4.2 (10H,m),7.32(1H,br.s),7.69 (1H,br.s),7.73(1H,br.s), 8.65(2H,br.s),9.11(1H,s). | KBr tablet 1650,1638,1594, 1577,1501,1437, 1251,1115,989. |
| 13 | [pyrimidine with CN, NEt pyridone] | B (24) | 55 | HCl salt >300 | DMSO—d₆ 1.29(3H,t,J=7Hz),3.88(3H, s),3.92(3H,s),3.9–4.1 (10H,m),7.34(1H,s),7.69 (1H,s),8.40(2H,br.s),8.8 (1H,s),9.12(1H,s). | KBr tablet 2230,1678,1619, 1600,1578,1520, 1436,1253,1107, 996,810. |
| 14 | [pyrimidine with CHO, NEt pyridone] | B (23) | 56 | HCl salt >300 | DMSO—d₆ 1.27(3H,t,J=7Hz),3.84 (3H,s),3.89(3H,s),4.02 (8H,m),7.12(1H,s),7.63 (1H,s),8.58(1H,s),9.14 (1H,s),10.49(1H,s). | Nujol 3330,3160,1685, 1668,1604. |
| 15 | [pyrimidine with CH₂C₆H₅, NEt pyridone] | B (14) | 69 | HCl salt 256.5 | DMSO—d₆ 1.25(3H,t,J=6Hz),3.88(3H, s),3.92(3H,s),3.92–4.20 (10H,m),7.20–7.40(5H,m), 7.56(1H,s),7.54(1H,s), 8.88(1H,s),8.70(1H,m), 9.08(1H,s). | KBr tablet 3300,3150,1650, 1598,1490,1430, 1390,1345,1248, 1112,983. |
| 16 | [pyrimidine with NEt thione] | B (25) | 36 | Free base 158–162 | CDCl₃ 1.46(3H,t,J=7Hz),3.90 (14H,m),4.59(2H,t,J= 7Hz),5.24(2H,br.s),6.64 (1H,d,J=7Hz),6.83(1H, s),6.97(1H,s),7.52(1H,d, J=7Hz),9.87(1H,s). | |
| 17 | [dihydropyrimidine with NEt pyridone] | A (39) | 48 | Free base 268–270 / HCl salt 275–276 | CDCl₃—CD₃OD 1.23(3H,t,J=7Hz),2.98 (2H,t,J=8Hz),3.62(4H,m), 4.00(14H,m),7.20(1H,s), 7.36(1H,s),8.80(1H,s). | |

TABLE 1-continued

[Structure: 4,5-dimethoxybenzene with substituents - amidine group with NH₂, and N=C-N connected to piperazine-N-Het]

| Ex. No. | Het | Prep'n (Ref. Ex. No.) | Yield (%) | Isolated form (m.p. °C.) | ¹H—NMR spectrum, δ ppm | IR spectrum (cm⁻¹) |
|---|---|---|---|---|---|---|
| 18 | [pyrimidine fused with ring containing COOEt, NEt, C=O] | B (14) | 61 | 279 | | KBr tablet 3320,3145,1734, 1678,1636,1604, 1576,1538. |
| 19 | [pyrimidine fused with ring containing C₆H₅, NH, C=O] | B (14) | 60 | 287 (dec'd) | DMSO—d₆ 3.12(2H,br.d,J=6Hz), 3.87(3H,s),3.92(3H,s), 4.05(8H,br.s),4.77(1H,t, J=6Hz),7.19(5H,s),7.63 (1H,s),7.78(1H,s),8.43 (1H,br.s),8.55(1H,s), 8.76(2H,br.s),12.48(1H, br.s). | KBr tablet 3345,3180,1590, 1514,1254. |
| 20 | [pyrimidine fused ring with Et on N, C=O] | A* | 76 | Free base<br><br>HCl salt 259 (dec'd) | DMSO—d₆ 1.32(3H,t,J=7Hz),3.80(3H, s),3.88(3H,s),3.82(8H,br. s),4.16(2H,q,J=7Hz),5.98 (1H,d,J=8Hz),6.74(1H,s), 7.13(2H,br.s),7.44(1H,s), 7.87(1H,d,J=8Hz),8.98(1H,s). | |
| 21 | [pyrimidine fused ring with Et on N, C=O, saturated] | A (56) | 82 | HCl salt 287-288 | DMSO—d₆ 1.16(3H,t,J=7Hz),2.72(2H, t,J=7Hz),3.44(4H),3.90 (8H,br.s),4.08(6H,s),7.78 (1H,s),7.84(1H,s),8.21(1H, s),8.71(1H,br.s),9.11(1H, br.s),12.80(1H,br.s). | |
| 22 | [pyrimidine fused with ring containing NH, C=O] | B (43) | 91 | HCl salt 300 (dec'd) | Not measured due to insolubility in DMSO MASS 422(M⁺—HCl) | KBr tablet 3300,3160,2900, 1705,1605,1585, 1328,1245,1112, 1020,985,835. |
| 23 | [pyrimidine fused with ring containing NEt, C=O] | B (45) | 92 | HCl salt 272 (dec'd) | 1.17(3H,t,J=9Hz),3.20-3.60(10H,m),3.88(3H,s), 3.92(3H,s),4.40(2H,s), 7.57(1H,s),7.76(1H,s), 8.66(1H,s),8.90(2H,br.s). | KBr tablet 3290,1663,1590, 1510,1430,1253, 1112,984,870, 793. |
| 24 | [pyrimidine fused with ring containing NCH₃, C=O] | B (45) | 94 | HCl salt 280-281 (dec'd) | 3.04(3H,s),3.88(3H,s), 3.94(3H,s),4.05(8H,m), 4.42(2H,s),7.44(1H,s), 7.78(1H,s),8.72(1H,s), 8.76(2H,brs). | Nujol 3600-2700,1665, 1615,1598,1520, 1260. |
| 25 | [pyrimidine fused with ring containing NPrⁱ, C=O] | B (45) | 76 | HCl salt 263-264 | DMSO—d₆ 1.22(6H,d,J=7Hz),3.88(3H, s),3.94(3H,s),4.05(8H,m), 4.38(3H,m),7.48(1H,s), 7.78(1H,s),8.72(1H,s), 8.80(2H,br.s). | Nujol 3400-2600,1665, 1615,1595,1515, 1254,1232,986. |

TABLE 1-continued

[Structure: 4,5-dimethoxy-2-(4-Het-piperazin-1-yl-methylidene-amino)benzamidine shown at top]

| Ex. No. | Het | Prep'n (Ref. Ex. No.) | Yield (%) | Isolated form (m.p. °C.) | $^1$H—NMR spectrum, δ ppm | IR spectrum (cm$^{-1}$) |
|---|---|---|---|---|---|---|
| 26 | [pyrimidine fused with NPr$^n$-pyrrolidinone] | B (45) | 63 | HCl salt 250–252 | DMSO—d$_6$ 0.87(3H,t,J=7Hz),1.60(2H, hextet,J=7Hz),3.43(2H,t, J=7Hz),3.88(3H,s),3.92 (3H,s),4.06(8H,s),4.41 (2H,s),7.64(1H,s),7.81 (1H,s),8.72(1H,s),8.73 (1H,br.),8.99(1H,br.), 12.46(1H,br.). | KBr tablet 3390,3120,2960, 2930,2870,1660, 1615,1590,1515, 1435,1255,1110, 985. |
| 27 | [pyrimidine fused with NBu$^n$-pyrrolidinone] | B (45) | 47 | HCl salt 263–265 | DMSO—d$_6$ 0.92(3H,t,J=7Hz),1.05– 1.76(4H),3.47(2H,t,J= 7Hz),3.89(3H,s),3.92 (3H,s),4.08(8H,s), 4.41(2H,s),7.68(1H,s), 7.82(1H,s),8.70(1H,s), 8.73(1H,br), 9.01(1H,br), 12.55(1H,br). | KBr tablet 3350,3120,2950, 2870,1660,1615, 1590,1510,1435, 1260,1230,1110, 985. |
| 28 | [pyrimidine fused with N-Et-pyrrolidinone] | B (55) | 72 | HCl salt 284–285 | DMSO—d$_6$ 1.20(3H,t,J=7Hz),3.50(2H, s),3.68(2H,q,J=7Hz),3.87 (3H,s),3.89(3H,s),3.93 (8H,br.s),7.61(1H,s), 7.75(1H,s),8.01(1H,s), 8.68(2H,br.s). | |
| 29 | [pyrimidine fused with N-CH$_3$-pyrrolidinone] | B (55) | 73 | HCl salt >300 | DMSO—d$_6$ 3.12(3H,s),3.50(2H,s), 3.88(14H,m),7.50(1H,s), 7.70(1H,s),8.03(1H,s). | KBr tablet 3125,1735,1670, 1635,1605,990. |
| 30 | [pyrimidine fused with N-CH(CH$_3$)$_2$-pyrrolidinone] | B (55) | 66 | HCl salt 284 (dec'd) | CD$_3$OD—CDCl$_3$ 1.54(6H,d,J=7Hz),3.42(2H, s),3.98(3H,s),4.03(11H, m),7.36(1H,s),7.57(1H,s), 7.98(1H,s). | KBr tablet 3380,3160,1745, 1660,1630,1595, 1445,1118. |
| 31 | [pyrimidine fused with NH-azepinone] | B (53) | 61 | HCl salt 300 (dec'd) | DMSO—d$_6$ 2.1–2.3(4H,m),2.6–2.9(2H, m),3.85(3H,s),3.90(3H,s), 3.7–4.2(8H,m),7.52(1H,s), 7.74(1H,s),8.03(1H,s), 8.83(2H,br.s),9.30(1H,s). | Nujol 3180,1690,1655, 1630,1590,1255. |
| 32 | [pyrimidine fused with N-Et-azepinone] | B (53) | 71 | HCl salt 228.5 | DMSO—d$_6$ 1.02(3H,t,J=9Hz),2.10– 2.30(4H,m),2.68(2H,br.s), 3.20–3.50(10H,m),3.85(3H, s),3.96(3H,s),7.56(1H,s), 7.74(1H,s),8.38(H,s), 8.66(1H,br.s),8.90(1H, br.s). | KBr tablet 3450,3330,3160, 2960,1632,1585, 1435,1255,1110, 980,850,770. |

TABLE 1-continued

Structure (shown at top of table):
4,5-dimethoxy-2-[N=C(piperazinyl-N-Het)]-benzamidine core

| Ex. No. | Het | Prep'n (Ref. Ex. No.) | Yield (%) | Isolated form (m.p. °C.) | $^1$H—NMR spectrum, δ ppm | IR spectrum (cm$^{-1}$) |
|---|---|---|---|---|---|---|
| 33 | (2-imino-cyclohexanone fused pyrimidine-type) | B (48) | 47 | HCl salt 279–280 | DMSO—$d_6$ 2.06(2H,m),2.58(2H,m), 2.88(2H,m),3.88(3H,s), 3.92(3H,s),3.46(8H,br. s),7.55(1H,s),7.78(1H,s), 8.79(1H,s). | KBr tablet 3350(broad), 3160(broad), 1655,1578,1515. |
| 34 | (NHCH$_3$ amide substituted dihydropyridine) | B (32) | 40 | HCl salt 260–265 (dec'd) | DMSO—$d_6$—CD$_3$OD 3.47(3H,s),3.94(14H,m), 4.28(2H,s),6.36(1H,d,J= 8Hz),7.36(1H,s),7.66(1H,d, J=8Hz),7.68(1H,s). | |
| 35 | (NEt amide substituted dihydropyridine) | A (32) | 25 | Free base<br><br>HCl salt 260–264 | CDCl$_3$—CD$_3$OD 1.32(3H,t,J=7Hz),3.9(16H, m),4.32(2H,s),6.06(1H,d, J=8Hz),6.92(1H,s),7.15 (1H,d,J=8Hz),7.20(1H,s). | |
| 36 | (CH$_3$, COCH$_3$ pyrimidine) | B (10) | 92 | HCl salt 293–294 (dec'd) | DMSO—$d_6$ 2.49(3H,s),2.58(3H,s), 3.87(3H,s),3.91(3H,s), 4.04(8H,br.s),7.60(1H, s),7.75(1H,s),8.62(1H,br. s),8.87(2H,br.s),11.34 (1H,br.s). | |
| 37 | (CONHEt pyrimidine) | B (30) | 90 | HCl salt 271–276 (dec'd) | DMSO—$d_6$ 1.13(3H,t,J=7Hz),3.40(2H, dq,J=5.3,7.0Hz),3.88(3H, s),3.93(3H,s),4.00(8H, br.s),7.40(1H,br.s),7.71 (1H,br.s),8.40(1H,br.s), 8.60(1H,br.s),8.83(2H,s), 8.83(1H,br.t). | |
| 38 | (Et, CONHEt pyrimidine) | B (10) | 42 | HCl salt 254–256 (dec'd) | DMSO—$d_6$ 1.12(3H,t,J=7Hz),1.20(3H, t,J=7Hz),2.82(2H,q,J= 7Hz),3.5(2H,m),3.86(3H,s), 3.90(3H,s),4.00(8H,m), 7.54(1H,s),7.75(1H,s), 8.38(1H,s). | KBr tablet 3320,3160,1630, 1580. |
| 39 | (CH$_3$, COOEt pyrimidine) | A (10) | 78 | Free base<br><br>HCl salt 267–269 | CDCl$_3$ 1.36(3H,t,J=7Hz),2.67(3H, s),3.95(14H,m),4.31(2H,q, J=7Hz),5.24(2H,br.s),6.82 (1H,s),6.95(1H,s), 8.84(1H,s). | |
| 40 | (CH$_3$, CONH$_2$ pyrimidine) | B (10) | 80 | HCl salt >300 | DMSO—$d_6$ 2.51(3H,s),3.91(6H,m), 3.97(6H,s),7.46(1H,s), 7.72(1H,s),8.50(1H,s), 8.70(2H,br.s). | KBr tablet 3340,3160,1650, 1626,1585. |

TABLE 1-continued

Structure at top:
- 4,5-dimethoxyphenyl group with: CH3O at position 4, CH3O at position 5
- substituents: C(=N—)(NH2) and N=C(—N(piperazine)N—Het)

| Ex. No. | Het | Prep'n (Ref. Ex. No.) | Yield (%) | Isolated form (m.p. °C.) | $^1$H—NMR spectrum, δ ppm | IR spectrum (cm$^{-1}$) |
|---|---|---|---|---|---|---|
| 41 | pyrimidine-CH3, CONHEt | B (10) | 30 | Free base; HCl salt 283–286 | CDCl3 1.23(3H,t,J=8Hz),2.52 (3H,2),3.44(2H,m),3.90 (14H,m),5.4(2H,br.s), 5.92(1H,br.s),6.88(1H,s), 6.94(1H,s),8.34(1H,s) | |
| 42 | pyrimidine-CH3, CONEt2 | B (10) | 23 | 212 (dec'd) | DMSO—d6 1.19(6H,t,J=8Hz),2.29(3H, s),3.45(4H,q,J=8Hz),3.88 (3H,s),3.90(3H,s),4.00 (8H,br.s),7.81(1H,s),7.86 (1H,s),8.25(1H,s),8.66(1H, br.s),9.07(1H,br.s). | KBr tablet 3380,1630,1594, 1534,1440,1278, 1256,1240. |
| 43 | pyrimidine-CH3, CONHC6H5 | B (10) | 69 | HCl salt 250 | DMSO—d6 2.51(3H,s),3.87(3H,s), 3.89(3H,s),4.03(8H,m), 7.00–7.45(3H,m),7.60–7.86 (4H,m),8.55(1H,s),8.74 (2H,br.s),10.30(1H,s). | Nujol 3455,3180,3120, 1630,1598. |
| 44 | pyrimidine-CH3, CONHCH2C6H5 | B (10) | 61 | HCl salt 277 | DMSO—d6 2.48(3H,s),3.73(3H,s), 3.89(3H,s),3.80–4.20 (8H,br.s),4.23(2H,d, J=5.6Hz),7.34(5H,s), 7.58(1H,s),7.74(1H,s), 8.50(1H,s),8.80(2H,br.s) | Nujol 3415,3260,3100, 1630,1587. |
| 45 | pyrimidine-CH3, CONH-cyclohexyl | B (10) | 62 | HCl salt 275–276 (dec'd) | CDCl3 1.0–2.0(10H),2.44(3H,s), 3.85(3H,s),3.90(3H,s), 3.97(8H,br.s),4.00(1H), 7.56(1H,s),7.75(1H,s),8.08 (1H,d,J=8Hz),8.36(1H,s), 8.80(2H,br.s). | KBr tablet 3280,1630,1585. |
| 46 | pyrimidine-CH3, CON(CH3)2 | B (10) | 65 | HCl salt 212–215 | DMSO—d6 2.28(3H,s),2.94(6H,br.s), 3.86(3H,s),3.90(3H,s),3.97 (8H,m),7.62(1H,s),7.78(1H, s),8.26(1H,s),8.70(1H,br. s),8.94(1H,br.s). | |
| 47 | pyrimidine-CH3, CONHN(CH3)2 | B (10) | 44 | HCl salt 282–284 (dec'd) | DMSO—d6 2.43(3H,s),2.59(6H,s), 3.85(3H,s),3.90(3H,s), 3.97(8H,br.s),7.55(1H,s), 7.66(1H,s),8.35(1H,s). | |
| 48 | pyrimidine-CH3, CONHCH2CF3 | B (10) | 39 | HCl salt 194–197 (dec'd) | DMSO—d6 2.47(3H,s),3.84(3H,s), 3.89(3H,s),3.96(10H),7.38 (1H,br.s),7.70(1H,br.s), 8.47(1H,s),8.70(1H,br.s), 8.90(1H,br.s),8.93(1H,br.t), J=5.5Hz). | |
| 49 | pyrimidine-CH3, CON-pyrrolidinyl | B (10) | 77 | HCl salt 246.5 | DMSO—d6 1.88(4H,br.s),2.35(3H,s), 3.18–3.60(4H,m),3.88(3H, s),3.91(3H,s),3.99(8H, br.s),7.60(1H,s),7.77(1H, s),8.32(1H,s),8.60(2H, br.s). | KBr tablet 3450,3120,1628, 1580,1526,1435, 1255,1110,985. |

TABLE 1-continued

[Structure: 4,5-dimethoxy-2-(piperazinyl-Het substituted amidine)benzamidine core]

| Ex. No. | Het | Prep'n (Ref. Ex. No.) | Yield (%) | Isolated form (m.p. °C.) | $^1$H—NMR spectrum, δ ppm | IR spectrum (cm$^{-1}$) |
|---|---|---|---|---|---|---|
| 50 | [pyrimidine with OH, COOEt, CH3] | B (69) | 75 | HCl salt 255–257 | DMSO—$d_6$ 1.28(3H,t,J=7Hz),3.86(3H, s),3.90(3H,s),3.98(8H, br.s),4.22(2H,q,J=7Hz), 7.53(1H,s),7.74(1H,s),8.49 (1H,s),8.65(1H,br.s),8.92 (1H,br.s),12.27(1H,br.s). | |
| 51 | [pyrimidine with OH, CN, CH3] | A (69) | 15 | Free base HCl salt 287–290 | CDCl$_3$—CD$_3$OD 3.97(14H,m),7.08(1H,s), 7.30(1H,s),8.10(1H,s). | |
| 52 | [pyrimidine with OCH3, CONEt2, CH3] | B (69) | 85 | HCl salt 278–281 (dec'd) | DMSO—$d_6$ 1.27(6H,br.t,J=6Hz),3.50 (4H,br.q,J=6Hz),4.07(9H, br.s),4.18(8H,br.s),7.92 (1H,s),8.01(1H,s),9.34(1H, s),8.87(1H,br.s),9.22(1H, br.s). | |
| 53 | [pyrimidine with SCH3, CONEt2, CH3] | B (69) | 51 | HCl salt 226–227 | DMSO—$d_6$ 1.14(3H,t,J=7Hz),1.22 (3H,t,J=7Hz),2.56(3H,s), 3.35(4H,m),3.92(6H,m),4.04 (8H,m),7.72(1H,s),7.83 (1H,s),8.10(1H,s),8.69 (1H,br.s),9.01(1H,br.s). | |
| 54 | [pyrimidine with NH2, COOEt, CH3] | A (69) | 84 | Free base 271–272 HCl salt 240–245 | CDCl$_3$—CD$_3$OD 1.37(3H,t,J=7Hz),4.00(14H, m),4.31(2H,q,J=7Hz),7.48 (1H,s),7.53(1H,s),8.63(1H,s). CDCl$_3$—CD$_3$OD 1.40(3H,t,J=7Hz),3.98(3H, s),4.04(3H,s),4.12(8H,m), 4.40(2H,q,J=7Hz),7.52(1H, s),7.57(1H,s),8.53(1H,s). | |
| 55 | [pyrimidine with NHCH3, COOEt, CH3] | B (69) | 82 | HCl salt 274–276 | DMSO—$d_6$ 1.29(3H,t,J=8Hz),2.96(3H, d,J=5Hz),3.86(3H,s),3.90 (3H,s),3.99(8H,br.s),4.22 (2H,q,J=8Hz),7.56(1H,s), 7.73(1H,s),8.09(1H,br.d, J=5Hz),8.49(1H,s),8.63(1H, br.s),8.88(1H,br.s),12.28 (1H,br.s). | |
| 56 | [pyrimidine with NMe2, COOEt, CH3] | B (69) | 54 | HCl salt 275–277 | DMSO—$d_6$ 1.26(3H,t,J=7Hz),3.0(6H, s),3.87(3H,s),3.90(3H,s), 3.98(8H,m),4.22(2H,q, J=7Hz),7.62(1H,s),7.78 (1H,s),8.36(1H,s),8.66(1H, br.s),8.94(1H,br.s). | |

TABLE 1-continued

Structure:
CH₃O and CH₃O substituents on benzene ring; benzene bearing -C(=N)-N(piperazinyl-N-Het) and -C(NH₂)=N- (amidine) group. Piperazine N—Het.

| Ex. No. | Het | Prep'n (Ref. Ex. No.) | Yield (%) | Isolated form (m.p. °C.) | ¹H—NMR spectrum, δ ppm | IR spectrum (cm⁻¹) |
|---|---|---|---|---|---|---|
| 57 | 2-methylpyrimidine with 4-NHEt, 5-COOEt | A (69) | 46 | Free base 223–227; HCl salt 223–225 | CDCl₃ 1.25(3H,t,J=7Hz),1.34(3H,t,J=7Hz),3.52(2H,d.q,J=5.7Hz),3.91(3H,s),3.94(3H,s),3.96(8H,s),4.27(2H,q,J=7Hz),5.23(2H,br.s),6.82(1H,s),6.93(1H,s),8.03(1H,br.t,J=5Hz),8.62(1H,s). | |
| 58 | 2-methylpyrimidine with 4-NEt₂, 5-COOEt | B (69) | 50 | Free base; HCl salt 280–282 | CDCl₃ 1.22(6H,t,J=7Hz),1.34(3H,t,J=7Hz),3.47(4H,q,J=7Hz),3.92(8H,m),3.94(3H,s),3.97(3H,s),4.28(2H,q,J=7Hz),5.28(2H,br.s),6.83(1H,s),6.94(1H,s),8.50(1H,s). | |
| 59 | 2-methylpyrimidine with 4-NHPr$^i$, 5-COOEt | B (69) | 91 | Free base; HCl salt 260–263 | CDCl₃ 1.27(6H,d,J=7Hz),1.34(3H,t,J=7Hz),3.96(14H,m),4.26(2H,q,J=7Hz),4.26(1H,m),5.22(2H,br.s),6.82(1H,s),6.95(1H,s),7.95(1H,d,J=7Hz),8.63(1H,s). | |
| 60 | 2-methylpyrimidine with 4-NHCOCH₃, 5-COOEt | A (69) | 49 | Free base 276–277; HCl salt 234–237 | CDCl₃—CD₃OD 1.40(3H,t,J=7Hz),2.50(3H,s),3.98(3H,s),4.03(3H,s),4.07(8H,m),4.40(2H,q,J=7Hz),7.47(1H,s),7.54(1H,s),8.85(1H,s). | |
| 61 | 2-methylpyrimidine with 4-NHEt, 5-COOPr$^i$ | B (69) | 88 | HCl salt 239–241 | DMSO—d₆ 1.24(3H,t,J=7Hz),1.36(6H,d,J=6Hz),3.62(2H,J=7Hz),3.89(3H,s),3.93(3H,s),4.10(8H,br.s),5.14(1H,heptet,J=6Hz),7.70(1H,s),7.79(1H,s),8.38(1H,s),8.64(2H,br.s),8.98(1H,s). | |
| 62 | 2-methylpyrimidine with 4-NHPr$^i$, 5-COOCH₃ | B (69) | 71 | HCl salt 286–289 | DMSO—d₆ 1.46(6H,d,J=6Hz),3.99(3H,s),4.09(3H,s),4.13(3H,s),4.22(8H,m),4.50(1H,m),7.85(1H,s),7.97(1H,s),8.18(1H,d,J=7Hz),8.73(1H,s),8.80(1H,br.s),9.11(1H,br.s). | |
| 63 | 2-methylpyrimidine with 4-NHEt, 5-CH₂CONHEt | B (69) | 51 | HCl salt 257–258 (dec'd) | DMSO—d₆ 1.03(3H,t,J=8Hz),1.18(3H,t,J=8Hz),3.20(4H),3.88(14H),7.37(2H,br.s),7.63(1H,s),7.68(1H,s),8.20(1H,br.t,J=7Hz),8.36(1H,br.s). | |

TABLE 1-continued

Structure: 4,5-dimethoxyphenyl with amidine and N=C(piperazine-N-Het) substituents; piperazine bears N—Het group.

| Ex. No. | Het | Prep'n (Ref. Ex. No.) | Yield (%) | Isolated form (m.p. °C) | $^1$H—NMR spectrum, δ ppm | IR spectrum (cm$^{-1}$) |
|---|---|---|---|---|---|---|
| 64 | pyrimidine with NH$_2$ and CONHEt | A (69) | 55 | Free base 273–275; HCl salt 280–283 | CDCl$_3$—CD$_3$OD 1.24(3H,t,J=7Hz),3.40(2H,q,J=7Hz),3.97(3H,s),4.04(3H,s),4.06(8H,m),7.52(1H,s),7.57(1H,s),8.36(1H,s). | |
| 65 | pyrimidine with NH$_2$ and CONEt$_2$ | A (69) | 48 | Free base 285–286; HCl salt 255–257 | CDCl$_3$ 1.22(6H,t,J=7Hz),3.46(4H,q,J=7Hz),3.90(8H,m),3.93(3H,s),3.97(3H,s),5.37(2H,br.s),5.78(2H,br.s),6.86(1H,s),7.02(1H,s),8.00(1H,s). | |
| 66 | pyrimidine with NHEt and CONHEt | B (69) | 65 | HCl salt 289–290 | DMSO—d$_6$ 1.13(3H,t,J=7Hz),1.21(3H,t,J=7Hz),3.22(2H,q,J=7Hz),3.46(2H,q,J=7Hz),3.87(3H,s),3.90(3H,s),4.03(8H,br.s),7.64(1H,s),7.76(1H,s),8.50(1H,s),8.62(2H,br.s),8.92(1H,br.s),9.48(1H,br.s),12.42(1H,br.s). | |
| 67 | pyrimidine with NHEt and CONEt$_2$ | B (69) | about 100 | HCl salt 236–237 | CDCl$_3$ 1.20(9H),3.42(6H),3.91(6H,s),4.09(8H,br.s),7.80(2H,br.s),8.28(2H,br.s),8.64(1H,br.s),9.08(1H,br.s),12.74(1H,br.s). | |
| 68 | pyrimidine with NHCH$_3$ and CONHCH$_3$ | B (69) | 48 | HCl salt 296–299 (dec'd) | CD$_3$OD 2.87(3H,s),3.06(3H,s),3.98(3H,s),4.04(11H,s),7.31(1H,s),7.58(1H,s),8.27(1H,s). | |
| 69 | pyrimidine with NHCH$_3$ and CON(CH$_3$)$_2$ | B (69) | 58 | HCl salt 260–262 (dec'd) | DMSO—d$_6$ 3.00(9H,s),3.88(3H,s),3.92(3H,s),4.07(8H,br.s),7.65(1H,s),7.75(1H,s),8.19(1H,s),8.25(1H,br.s),8.61(1H,br.s),8.88(1H,br.s),12.46(1H,br.s). | |
| 70 | quinazoline | B (73) | 82 | Free base; HCl salt 284–285 | CDCl$_3$ 3.92(3H,s),3.98(3H,s),4.02(8H,m),6.84(1H,s),6.98(1H,s),7.2(1H,m),7.64(3H,m),9.02(1H,s). | |
| 71 | 6,7-dimethoxyquinazoline | B (73) | 50 | Free base; HCl salt 295–300 | CDCl$_3$ 3.90(20H,m),5.55(2H,br.s),6.90(2H,s),6.96(1H,s),6.98(1H,s),8.82(1H,s) | |

TABLE 1-continued

| Ex. No. | Het | Prep'n (Ref. Ex. No.) | Yield (%) | Isolated form (m.p. °C.) | $^1$H—NMR spectrum, δ ppm | IR spectrum (cm$^{-1}$) |
|---|---|---|---|---|---|---|
| 72 | (structure with NH$_2$, OCH$_3$, OCH$_3$) | A** | 60 | Free base<br><br>HCl salt<br>>300 | DMSO—d$_6$<br>3.80(12H,s),3.85(8H,s),<br>6.78(2H,s),7.18(4H,br.s),<br>7.44(2H,s). | KBr tablet<br>1640,1625,1585,<br>1523,1275,1250. |
| 73 | (structure with N(CH$_3$)$_2$, OCH$_3$, OCH$_3$) | A*** | 56 | Free base<br><br>HCl salt<br>262–263 | CDCl$_3$—CD$_3$OD<br>3.44(6H,s),4.00(20H,m),<br>7.30(1H,s),7.35(1H,s),<br>7.48(1H,s),7.50(1H,s). | |
| 74 | (structure with OEt) | A (77) | 13 | Free base<br><br>HCl salt<br>>300 | CDCl$_3$<br>1.68(3H,t,J=8Hz),3.92(3H,<br>s),3.98(9H,s),4.54(2H,q,<br>J=8Hz),5.34(2H,br.s),6.85<br>(1H,s),6.94(1H,d,J=7Hz),<br>6.97(1H,s),8.07(1H,d,<br>J=7Hz),9.28(1H,s) | |
| 75 | (structure with SCH$_3$, CH$_3$) | B (75) | 83 | HCl salt<br>250<br>(dec'd) | CDCl$_3$—DMSO—d$_6$<br>1.32(3H,d,J=7Hz),1.88(4H,<br>m),2.68(3H,s),2.70(2H,m),<br>3.45(1H,m),3.97(3H,s),<br>4.01(3H,s),4.18(8H,m),<br>7.78(1H,s),8.03(1H,s). | |
| 76 | (structure with CH$_3$, N, O, CH$_3$) | B (59) | 43 | HCl salt<br>265–269 | CD$_3$OD—CDCl$_3$<br>3.14(3H,s),3.23(3H,s),<br>3,69(4H,br.s),4.0(14H,m),<br>7.23(1H,s),7.56(1H,s),<br>8.62(1H,s). | KBr tablet<br>1595,1480,1234. |
| 77 | (structure with NHCH$_3$, CONEt$_2$) | B (69) | 70 | HCl salt<br>271–272 | CD$_3$OD—CDCl$_3$<br>1.24(6H,t,J=7Hz),3.0(3H,<br>s),3.48(4H,q,J=7Hz),4.0<br>(14H,m),7.33(1H,s),7.56<br>(1H,s),7.85(1H,s). | KBr tablet<br>3375,3170,1625,<br>1582,1110. |
| 78 | (structure with NHPr$^i$, CONEt$_2$) | B (69) | 82 | HCl salt<br>261–264 | DMSO—d$_6$—CDCl$_3$<br>1.20(6H,m),3.40(4H,m),<br>3.90(15H,m),7.54(1H,s),<br>7.74(1H,s),7.86(1H,s),<br>8.70(2H,br.s). | KBr tablet<br>3200,3108,2956,<br>1578,1478,1431,<br>1232. |
| 79 | (structure with NHEt, CONMe$_2$) | B (69) | 69 | HCl salt<br>281–282 | CD$_3$OD—CDCl$_3$<br>1.24(3H,t,J=7Hz),3.11(6H,<br>s),3.51(2H,q,J=7Hz),4.0<br>(14H,m),7.31(1H,s),7.56<br>(1H,s),7.91(1H,s). | KBr tablet<br>3300,3160,1585,<br>1113,995. |

TABLE 1-continued

[Structure: 4,5-dimethoxyphenyl with C(=NH)NH2 group and guanidine linked to piperazine-N-Het]

| Ex. No. | Het | Prep'n (Ref. Ex. No.) | Yield (%) | Isolated form (m.p. °C.) | $^1$H—NMR spectrum, δ ppm | IR spectrum (cm$^{-1}$) |
|---|---|---|---|---|---|---|
| 80 | [structure with N, NHEt, CONPr$^n_2$] | B (69) | 90 | HCl salt 249–250 | DMSO—d$_6$—CDCl$_3$ 0.815(6H,t,J=7Hz),1.14 (3H,t,J=6.5Hz),1.51(4H,m), 3.36(6H,m),3.91(14H,m), 7.0(1H,br.s),7.58(1H,s), 7.75(1H,s),7.81(1H,s), 8.8(2H,br.s),12.4(1H,br.s). | KBr tablet 3408,3116,2952, 2916,1580,1487, 1430,1230. |

*The raw material, 5,8-dihydro-8-ethyl-5-oxo-2-piperazinopyrido[2,3-d]pyrimidine, was synthesized by the process described in Japanese Patent Laid-Open No. 18600/1978.
**The raw material, 4-amino-6,7-dimethoxy-2-piperazinoquinazoline, was synthesized by the process described in J. Chem. Soc., 1965, 1759 and J. Med. Chem., 20, 146(1977).
***The raw material, 4-dimethylamino-6,7-dimethoxy-2-piperazinoquinazoline, was synthesized by the process described in J. Chem. Soc., 1965, 1759 and J. Med. Chem., 20, 146(1977).

EXAMPLE 81

4-Amino-6,7,8-trimethoxy-2-(4-(5,6-dihydro-6-ethyl-5-oxopyrido[4,3-d]pyrimidin-2-yl)piperazino)quinazoline hydrochloride

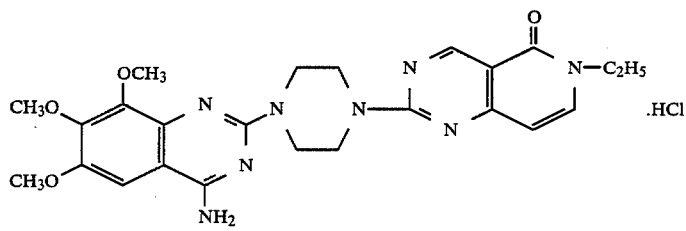

In 20 ml of isoamyl alcohol as a solvent, 1.04 g of 4-amino-2-chloro-6,7,8-trimethoxyquinazoline (synthesized by the process described in Japanese Patent Laid-Open No. 7180/1971) and 1.0 g of the 5,6-dihydro-6-ethyl-5-oxo-2-piperazinopyrido[4,3-d]pyrimidine obtained in Referential Example 14 were refluxed for 4 hours. After allowing the reaction mixture to cool down, the precipitated crystals were collected by filtration and then washed with methanol to obtain 1.16 g of the above-identified compound (yield: 61%).

Melting point: 241°–242° C.

$^1$H-NMR spectrum (DMSO-d$_6$ solution, δ ppm): 1.23 (3H, t, J=7 Hz), 3.96 (17H, m), 6.30 (1H, d, J=8 Hz), 7.80 (1H, s), 7.85 (1H, d, J=8 Hz), 9.12 (1H, s).

EXAMPLE 82

4-Amino-6,7-dimethoxy-2-(4-(5,6-dihydro-6-ethyl-5-oxopyrido[4,3-d]pyrimidin-2-yl)homopiperazino)-quinazoline and its hydrochloride

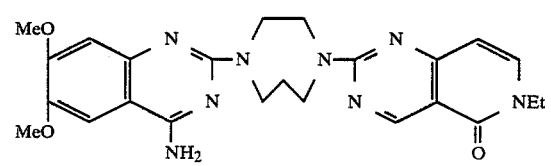

In 20 ml of isoamyl alcohol as a solvent, were refluxed for 9 hours 0.81 g of 4-amino-2-chloro-6,7-dimethoxyquinazoline, 0.88 g of the 5,6-dihydro-6-ethyl-5-oxo-2-homopiperazinopyrimido[4,3-d]pyrimidine obtained in Referential Example 14 and 0.48 g of tri-n-propylamine. After allowing the reaction mixture to cool down, 0.5 g of sodium hydrogencarbonate and 20 ml of water were added. After thoroughly stirring the resultant mixture, the solvent was distilled off. The residue was washed with water and then with hot methanol, thereby obtaining 1.24 g of the intended product (yield: 83%).

$^1$H-NMR spectrum (CDCl$_3$-DMSO-d$_6$ solution, δ ppm): 1.34 (3H, t, J=6 Hz), 2.15 (2H, br. s), 3.93 (18H, m), 6.30 (1H, d, J=7 Hz), 7.20 (1H, s), 7.28 (1H, s), 7.41 (1H, d, J=7 Hz), 9.19 (1H, s).

The free base (1.24 g) obtained in the above preparation process was dissolved in methanoldichloromethane, followed by an addition of 10 ml of HCl-saturated ethanol. Thereafter, excess hydrogen chloride and solvent were distilled off to obtain 1.40 g of the hydrochloride of the above-identified compound.

Melting point: 236°–238° C.

REFERENTIAL EXAMPLE 79

2-(4-Benzylpiperazino)-6-cyclohexyl-5-oxo-5,6-dihydro(7H)pyrrolo[3,4-d]pyrimidine

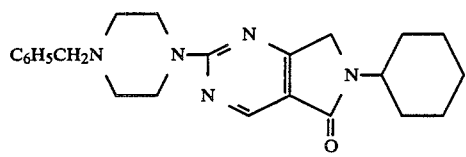

Dissolved in 40 ml of isoamyl alcohol was 2.0 g (5.34 mmol) of ethyl 2(4-benzylpiperazino)-4-chloromethylpyrimidine-5-carboxylate, followed by an addition of 10.5 g (107 mmol) of cyclohexylamine. The resultant mixture was refluxed for 6 hours. After completion of the reaction, the solvent was distilled off and the residue was washed with ether to obtain 1.32 g of the above-identified compound as crystals (yield: 63%).

Melting point: 176°–178° C.

Infrared absorption spectrum (CHCl$_3$ solution, cm$^{-1}$): 3120, 2850, 2800, 1670, 1610, 1572, 1350, 1005.

$^1$H-NMR spectrum (CDCl$_3$ solution, δ ppm): 1.20–2.00 (10H), 2.52 (4H, t, J=5 Hz), 3.58 (2H, s), 3.96 (4H, t, J=5 Hz), 4.18 (2H, s), 7.37 (5H, s), 8.69 (1H, s).

The compounds given in Table 2 were also obtained in a similar manner.

REFERENTIAL EXAMPLE 80

6-Cyclohexyl-5-oxo-2-piperazino-5,6-dihydro(7H)pyrrolo[3,4-d]pyrimidine

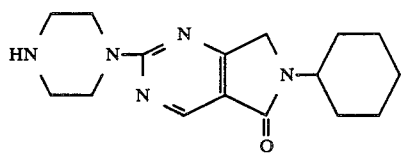

Dissolved in 30 ml of ethanol was 1.2 g (3.07 mmol, Referential Example 79) of 2-(4-benzylpiperazino)-6-cyclohexyl-5-oxo-5,6-dihydro(7H)pyrrolo-[3,4-d]pyrimidine, followed by an addition of 0.16 g of 10% Pd-C. The pyrimidine derivative was hydrogenated at 60° C. After completion of the reaction, Pd-C was filtered off and ethanol was distilled off to obtain 0.92 g of the above-identified compound as crystals (yield: about 100%).

Melting point: 177°–180° C.

Infrared absorption spectrum (CHCl$_3$ solution, cm$^{-1}$): 3330, 2920, 2850, 1670, 1610, 1570, 1345, 978.

$^1$H-NMR spectrum (CDCl$_3$ solution, δ ppm): 1.20–2.00 (10H), 2.94 (4H, t, J=5 Hz), 3.92 (4H, t, J=5 Hz), 4.19 (2H, s), 8.69 (1H, s).

The compounds given in Table 3 were also obtained in a similar manner.

TABLE 2

| R$^2$ | Yield (%) | m.p. (°C.) | $^1$H—NMR spectrum (CDCl$_3$, δ ppm) | IR spectrum (KBr tablet, cm$^{-1}$) |
|---|---|---|---|---|
| —CH$_2$CH$_2$N(CH$_3$)CH$_3$ | 45 | 149–151 | 2.28(6H,s), 2.54(6H,m), 3.56(2H,s), 3.66 (2H,t,J=6Hz), 3.96(4H,m), 4.35(2H,s), 7.36(5H,m), 8.67(1H,s). | 2950, 2820, 1680, 1620, 1530, 1455. |
| —CH$_2$CH$_2$OCH$_3$ | 46 | 97–98 | 2.51(4H,m), 3.36(3H,s), 3.56(2H,s), 3.66 (4H,m), 3.95(4H,m), 4.36(2H,s), 7.35 (5H,m), 8.68(1H,s). | 2860, 1690, 1620, 1515, 1350. |
| —CH$_2$CH$_2$OH | 62 | 160–161 | 2.52(4H,m), 3.15(1H,br.s), 3.58(2H,s), 3.73(2H,m), 3.96(6H,m), 4.36(2H,s), 7.38 (5H,m), 8.66(1H,s). | 3410, 2950, 2870, 1660, 1620, 1560, 1460. |
| —CH$_2$CH$_2$—C$_6$H$_5$ | 59 | 162–164 | 2.52(4H,m), 2.97(2H,t,J=7Hz), 3.57(2H,s), 3.83(2H,t,J=7Hz), 3.94(4H,m), 4.03(2H,s), 7.34(10H,m), 8.68(1H,s). | 2950, 1680, 1620, 1510, 1350. |
| —(CH$_2$)$_6$CH$_3$ | 46 | 135–137 | 0.88–1.6(11H,m), 2.52(4H,m), 3.58(4H,m), 3.96(4H,m), 4.20(2H,s), 7.37(5H,m), 8.68(1H,s). | 2930, 1680, 1620, 1518, 1350, 1110. |

TABLE 3

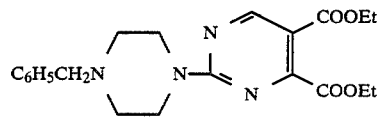

| R | Yield (%) | m.p. (°C.) | $^1$H—NMR spectrum (CDCl$_3$, δ ppm) | IR spectrum (KBr tablet, cm$^{-1}$) |
|---|---|---|---|---|
| —CH$_2$CH$_2$N(CH$_3$)$_2$ | 88 | 166–167 | 1.80(1H,br.s), 2.28(6H,s), 2.54 (2H,t, J=6Hz), 2.94(4H,m), 3.66(2H,t,J=6Hz), 3.92(4H,m), 4.35(2H,s), 8.68(1H,s). | 3220, 2930, 2825, 1670, 1518, 1530. |
| —CH$_2$CH$_2$OCH$_3$ | 99 | 113–115 | 2.98(4H,m), 3.40(3H,s), 3.66(4H,m), 3.97(4H,m), 4.21(2H,s), 8.72(1H,s). | 3250, 2940, 1680, 1620, 1530, 1430. |
| —CH$_2$CH$_2$OH | 94 | 152–154 | 2.32(2H,br.s), 2.96(4H,m), 3.72(2H,m), 3.94(6H,m), 4.39(2H,s), 8.69(1H,s). | 3380, 3320, 1660, 1620, 1520, 1355. |
| —CH$_2$CH$_2$—C$_6$H$_5$ | 97 | 168–170 | 1.72(1H,br.s), 2.99(6H,m), 3.91(6H,m), 4.03(2H,s), 7.30(5H,m), 8.69(1H,s). | 3300, 2900, 1670, 1618, 1530, 1230. |
| —(CH$_2$)$_6$CH$_3$ | 86 | 265–270 (dec'd) | 0.88–1.6(11H,m), 2.96(6H,m), 3.55(2H,m), 3.94(4H,m), 4.21(2H,s), 8.69(1H,s). | 2930, 1685, 1620, 1570, 1525, 1355. |

REFERENTIAL EXAMPLE 81

6-(4-Benzylpiperazino)-2-methyl-3-oxo-2,3-dihydro-1H-pyrazolo[3,4-d]pyrimidine

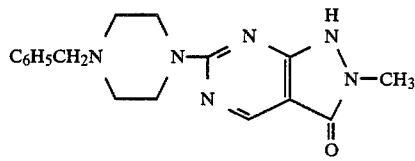

Added at room temperature (about 20° C.) to an EtOH solution (20 ml) of 2.0 g of 2-methylhydrazine was a chloroform solution (12 ml) of 5.3 g of the ethyl 2-(4-benzylpiperazino)-4-chloropyrimidine-5-carboxylate synthesized in Referential Example 63. The resultant mixture was stirred for 3 hours. The solvent was distilled off and ethyl acetate was added to the resultant solid. After thoroughly mixing the thus-obtained mixture, 3 g of crystals were collected by filtration (yield: 63%).

Melting point: 210°–212° C.

$^1$H-NMR spectrum (CDCl$_3$ solution, δ ppm): 2.55 (4H, m), 3.60 (5H, s), 3.96 (4H, m), 6.98 (1H, br.s), 7.36 (5H, m), 8.72 (1H, s).

REFERENTIAL EXAMPLE 82

6-Piperazino-2-methyl-3-oxo-2,3-dihydro-1H-pyrazolo[3,4-d]pyrimidine

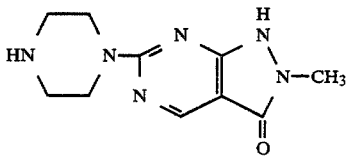

A catalytic amount of 10% Pd-C was added to an EtOH solution (30 ml) of 3.0 g of 6-benzylpiperazino-2-methyl-3-oxo-2,3-dihydro-1H-pyrazolo[3,4-d]pyrimidine. In a hydrogen atmosphere, the resultant mixture was stirred at 60° C. for 3 hours. After allowing the reaction mixture to cool down, the catalyst was filtered off and the filtrate was concentrated to obtain 1.8 g of the above-identified compound as yellowish crystals (yield: 88%).

Melting point: 272°–276° C. (decomposed).

$^1$H-NMR spectrum (DMSO-d$_6$ solution, δ ppm): 3.20 (4H, m), 3.64 (3H, s), 4.24 (2H, m), 8.70 (1H, s).

Infrared absorption spectrum (KBr tablet, cm$^{-1}$): 3600–3300, 1700, 1621, 1565, 1443.

REFERENTIAL EXAMPLE 83

Diethyl 2-(4-benzylpiperazino)-4,5-pyrimidinedicarboxylate

To absolute ethanol with 0.91 g of sodium dissolved therein, 11.5 g of 1-amidino-4-benzylpiperazine sulfate was added. The resultant mixture was stirred at room temperature for 30 minutes, to which 8.8 g of ethyl ethoxymethyleneoxaloacetate [synthesized by the process described in J. Am. Chem. Soc., 73, 3684 (1951)] was added. After allowing them to react at room temperature for 2 days, the reaction was caused to proceed further for 1 hour while heating the reaction mixture under reflux. After cooling the reaction mixture to room temperature, ethanol was distilled off under reduced pressure and the residue was dissolved in a mixture of water and ethyl acetate. After separation of the water layer, the ethyl acetate layer was washed with water and then with saturated saline. After drying the ethyl acetate layer with magnesium sulfate, ethyl acetate was distilled off under reduced pressure to obtain 13.7 g of the above-identified compound as light brown crystals (yield: 96%).

Melting point: 66° C.

Infrared absorption spectrum (nujol, cm⁻¹): 1750, 1715, 1590.

¹H-NMR spectrum (CDCl₃ solution, δ ppm): 1.32 (3H, t, J=7 Hz), 1.39 (3H, t, J=7 Hz), 2.49 (4H, t, J=5 Hz), 3.54 (2H, s), 3.94 (4H, t, J=5 Hz), 4.30 (2H, q, J=7 Hz), 4.42 (2H, q, J=7 Hz), 7.31 (5H, s), 8.85 (1H, s).

REFERENTIAL EXAMPLE 84

N,N'-Diethyl-2-(4-benzylpiperazino)-4,5-pyrimidinedicarboxylic acid amide

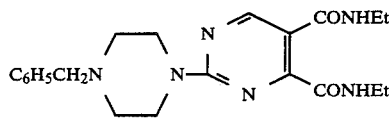

Charged in an autoclave were 1.5 g of the diethyl 2-(4-benzylpiperazino)-4,5-pyrimidinedicarboxylate synthesized in Referential Example 83, 1 ml of ethylamine and 20 ml of DMF. They were reacted at 150° C. for 1 hour. After the reaction, DMF was distilled off and the residue was added with 20 ml of hexane and 5 ml of ethyl acetate. The resultant light yellowish crystals of the above-identified compound were collected by filtration [yield: 0.8 g (54%)].

Melting point: 201° C.

Infrared absorption spectrum (nujol, cm⁻¹): 3290, 1650, 1635, 1585.

¹H-NMR spectrum (CDCl₃ solution, δ ppm): 1.23 (3H, t, J=7 Hz), 1.24 (3H, t, J=7 Hz), 2.54 (4H, t, J=5 Hz), 3.46 (2H, q, J=7 Hz), 3.49 (2H, q, J=7 Hz), 3.56 (2H, s), 3.89 (4H, t, J=5 Hz), 7.32 (5H, s), 7.6 (1H, br.s), 9.16 (1H, s), 9.5 (1H, br.s).

REFERENTIAL EXAMPLE 85

Diethyl 2-piperazine-4,5-pyrimidinedicarboxylate

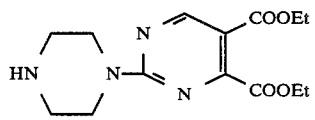

The diethyl 2-(4-benzylpiperazino)-4,5-pyrimidinedicarboxylate (1.5 g) synthesized in Referential Example 83 was dissolved in a mixture of 20 ml of ethanol and 5 ml of acetic acid, followed by an addition of 0.15 g of 10% Pd-C. The resultant mixture was stirred at 70° C. for 1 hour in a hydrogen atmosphere. After the reaction, ethanol and acetic acid were distilled off under reduced pressure and the residue was dissolved in dichloromethane. The dichloromethane solution was washed with a saturated aqueous solution of sodium bicarbonate. Dichloromethane was distilled off under reduced pressure to obtain 0.97 g of the above-identified compound as a yellowish oily product (yield: 81%).

Infrared absorption spectrum (neat, cm⁻¹): 2980, 1745, 1715, 1590, 1540, 1290, 1250.

¹H-NMR spectrum (CDCl₃ solution, δ ppm): 1.33 (3H, t, J=7 Hz), 1.40 (3H, t, J=7 Hz), 2.03 (1H, br.s), 2.92 (4H, t, J=5 Hz), 4.31 (2H, t, J=7 Hz), 4.43 (2H, t, J=7 Hz), 8.87 (1H, s).

REFERENTIAL EXAMPLE 86

N,N'-Diethyl-2-piperazino-4,5-pyrimidinedicarboxylic acid amide

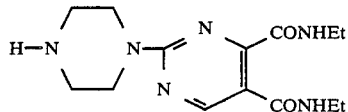

Dissolved in 30 ml of ethanol was 0.8 g of the N,N'-diethyl-2-(4-benzylpiperazino)-4,5-pyrimidinedicarboxylic acid amide synthesized in Referential Example 84, followed by an addition of 0.08 g of 10% Pd-C. The resultant mixture was stirred at 60° C. for 4 hours in a hydrogen atmosphere. After filtering off the 10% Pd-C, ethanol was distilled off under reduced pressure to obtain the above-identified compound as light yellowish crystals [yield: 0.55 g (89%)].

Melting point: 73° C.

Infrared absorption spectrum (KBr tablet, cm⁻¹): 3300, 1640, 1585, 1520, 1450, 1265.

¹H-NMR spectrum (CDCl₃ solution, δ ppm): 1.24 (3H, t, J=7 Hz), 1.26 (3H, t, J=7 Hz), 1.76 (1H, br.s), 2.94 (4H, t, J=5 Hz), 3.42 (2H, dt, J=7 Hz, 2 Hz), 3.49 (2H, dt, J=7 Hz, 2 Hz), 3.86 (4H, t, J=5 Hz), 7.6 (1H, br.s), 9.16 (1H, s), 9.5 (1H, br.s).

REFERENTIAL EXAMPLE 87

3,5-Dinitro-2-piperazinopyridine

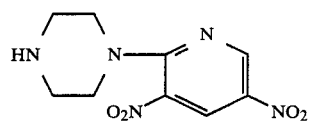

In n-butanol (20 ml), 1 g of 2-chloro-3,5-dinitropyridine and 2.1 g of anhydrous piperazine were refluxed for 2 hours. Thereafter, n-butanol was distilled off under reduced pressure, followed by extraction with 2N-NaOH and chloroform. The chloroform layer was washed with saturated saline and then dried with anhydrous magnesium sulfate. Under reduced pressure, chloroform was distilled off to obtain 0.4 g of the intended product (yield: 32%).

EXAMPLE 83

4-Amino-6,7-dimethoxy-2-(4-(2-methyl-3-oxo-2,3-dihydro-1H-pyrazolo[3,4-d]pyrimidine-6-yl)piperazino)-quinazoline hydrochloride

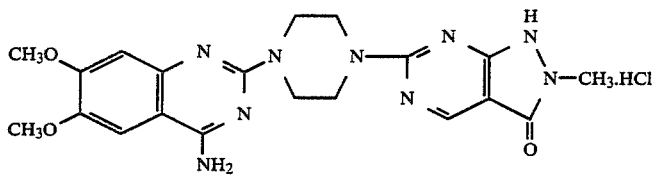

Refluxed for 5 hours in isoamyl alcohol (30 ml) were 1.74 g (7.3 mmol) of 4-amino-2-chloro-6,7-dimethoxyquinazoline and 1.60 g (7.3 mmol) of the 6-piperazino-2-methyl-3-oxo-2,3-dihydro-1H-pyrazolo[3,4-d]pyrimidine synthesized in Referential Example 82. After allowing the reaction mixture to cool down, the resultant crystals were collected by filtration and then washed with ethanol. The thus-obtained crude crystals were added with ethanol and refluxed for 2 hours. After allowing the mixture to cool down, crystals were collected by filtration and then dried to obtain 2.90 g of the above-identified compound (yield: 84%).

Melting point: 272°–276° C. (decomposed).

Infrared absorption spectum (KBr tablet, cm$^{-1}$): 3400, 3180, 1655, 1594, 1530, 1495, 1438, 1257, 1112, 985.

$^1$H-NMR spectrum (DMSO-d$_6$ solution, δ ppm): 3.64 (3H, s), 3.90 (3H, s), 3.94 (3H, s), 4.05 (8H, m), 7.64 (1H, s), 7.70 (1H, br.s), 7.82 (1H, s), 8.76 (1H, br.s), 8.82 (1H, s), 8.98 (1H, br.s), 12.50 (1H, br.s).

EXAMPLES 84 TO 93

Following the procedure of Example 83, the compounds given in Table 4 were obtained by using the piperazinopyrimidine derivatives obtained in their corresponding Referential Examples or the like.

TABLE 4

| Ex. No. | Het | Yield (%) | Isolated form (m.p. °C.) | $^1$H—NMR spectrum, δppm | IR spectrum (cm$^{-1}$) |
|---|---|---|---|---|---|
| 84 | (pyrimidine with COOEt, COOEt) | 90 | HCl salt 291 (dec'd) | DMSO—d$_6$ 1.27(3H,,J=7Hz),1.31(3H,t,J=7Hz), 3.86(3H,s),3.90(3H,s),4.03(8H, br.s),4.27(2H,q,J=7Hz),4.35(2H, q,J=7Hz),7.56(1H,s),7.76(1H,s), 8.7(1H,br.s),8.92(1H,s),9.0(1H,br.s). | nujol 3160,1720,1715, 1665,1640,1605, 1590,1535. |
| 85 | (pyrimidine with CONHEt, CONHEt) | 58 | HCl salt 298 (dec'd) | DMSO—d$_6$ 1.09(3H,t,J=7Hz),1.12(3H,t,J=7Hz), 3.29(4H,q,J=7Hz),3.85(3H,s),3.90 (3H,s),4.00(8H,br.s),7.52(1H,s), 7.74(1H,s),8.25(1H,br.s),8.59(1H, s),8.7(3H,br.s). | nujol 3270,3200,1650, 1585,1500,1255. |
| 86 | (pyrazolopyrimidinone with N—CH$_2$CH$_2$N(CH$_3$)$_2$) | 50 | HCl salt 296–298 (dec'd) | CD$_3$OD—CDCl$_3$ 2.68(6H,s),3.06(2H,t,J=6Hz),3.86 (2H,t,J=6Hz),3,98(3H,s),4.02(3H, s),3.06(8H,m),4.46(2H,s),7.25(1H, s),7.54(1H,s),8.74(1H,s). | KBr tablet 3340,1650,1613, 1580,1435,1240. |
| 87 | (pyrazolopyrimidinone with N—CH$_2$CH$_2$OCH$_3$) | 35 | HCl salt 254–256 | CD$_3$OD—CDCl$_3$ 3.40(3H,s),3.72(4H,m),3.99(3H,s), 4.40(3H,s),4.12(8H,m),4.50(2H,s), 7.28(1H,s),7.62(1H,s),8.74(1H,s). | KBr tablet 3400,1660,1590, 1258. |
| 88 | (pyrazolopyrimidinone with N—CH$_2$CH$_2$OH) | 90 | HCl salt 282–283 (dec'd) | DMSO—d$_6$ 3.58(4H,m),3.88(3H,s),3.92(3H,s), 4.04(8H,s),4.48(2H,m),7.58(1H,s), 7.79(1H,s),8.72(1H,s). | KBr tablet 3320,1660,1612, 1590,1433,1259. |

TABLE 4-continued

[Structure shown: 6,7-dimethoxyquinazoline core with piperazine-N-Het substituent and NH2 group]

| Ex. No. | Het | Yield (%) | Isolated form (m.p. °C.) | ¹H—NMR spectrum, δppm | IR spectrum (cm⁻¹) |
|---|---|---|---|---|---|
| 89 | [pyrimidine fused structure with N—CH₂CH₂—phenyl and C=O] | 57 | HCl salt 270–270.8 | CD₃OD—CDCl₃ 3.00(2H,t,J=7Hz),3.86(2H,t,J=7Hz), 3.98(3H,s),4.03(3H,s),4.06(8H,m), 4.18(2H,s),7.22(1H,s),7.28(5H,m), 7.61(1H,s),8.71(1H,s). | KBr tablet 3320,1650,1590, 1430,1255. |
| 90 | [pyrimidine fused structure with N—(CH₂)₆CH₃ and C=O] | 57 | HCl salt 257.6–258.4 | CD₃OD—CDCl₃ 0.90–1.7(13H,m),3.6(2H,t,J=7H), 3.99(3H,s),4.05(3H,s),4.10(8H,m), 4.39(2H,s),7.30(1H,s),7.61(1H,s), 8.73(1H,s). | KBr tablet 3400,1650,1590, 1430,1255. |
| 91 | [pyrimidine fused structure with N—cyclohexyl and C=O] | 55 | HCl salt 252–254 | DMSO—d₆ 1.00–2.2(10H),3.5(1H,m),3.88(3H, s),3.92(3H,s),4.07(8H,s),4.38(2H, s),7.67(1H,s),7.81(1H,s),8.71(1H, s),9.00(2H,br.d). | KBr tablet 3340,1655,1613, 1595,1520,1260. |
| 92 | [pyridine with O₂N and NO₂ substituents] | 62 | HCl salt 281–291 | DMSO—d₆ 3.86(3H,s),3.89(3H,s),3.98(8H,m), 7.48(1H,s),7.75(1H,s),8.92(1H,d, J=2Hz),9.22(1H,d,J=2Hz). | KBr tablet 3080,1645,1588, 1328,1108. |
| 93 | [pyridine with CONEt₂] | 38 | HCl salt >300 | DMSO—d₆ 1.16(6H,t,J=7Hz),3.24–3.56(12H,m), 3.89(3H,s),3.92(2H,s),6.90(1H,d, J=9Hz),7.52–7.70(2H,m),7.75(1H,s), 8.18(1H,d,J=2Hz),8.60(1H,br.s), 8.90(1H,br.s). | KBr tablet 3350,3120,2900, 1652,1590,1242, 1110,985,765. |

EXAMPLE 94

4-Amino-6,7-dimethoxy-2-(4-(2-quinolyl)piperazino)-quinazoline hydrochloride

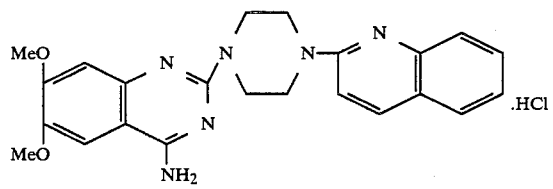

Mixed were 0.72 g (2.5 mmol) of 4-amino-6,7-dimethoxy-2-piperazinoquinazoline, 0.63 g (3.9 mmol) of 2-chloroquinoline, 0.43 g (3 mmol) of tri-n-propylamine and 15 ml of isoamyl alcohol. The mixture was refluxed for 16 hours. After cooling the reaction mixture, the resultant crystals were collected by filtration, followed by their dissolution in a mixed solvent of 10 ml of dichloromethane and 10 ml of methanol. To the solution, 2 ml of a 20% ethanol solution of hydrochloric acid was added. The solvents were distilled off to obtain 0.90 g of the above-identified compound (yield: 80%).

Melting point: 243.5°–244.5° C.

¹H-NMR spectrum (DMSO-d₆ solution, δ ppm): 3.87 (3H, s), 3.91 (3H, s), 3.7–4.1 (8H, br.s), 6.8–8.1 (8H, m).

REFERENTIAL EXAMPLE 88

4,5-Dimethoxy-2-nitrobenzaldehyde

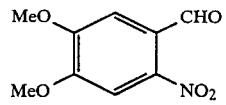

After reacting 135 g of 3,4-dimethoxybenzaldehyde and 500 ml of conc. nitric acid at 10° C. for 20 hours, the reaction mixture was poured in 3 l of ice water and the resultant crystals were collected by filtration. The crystals were dissolved in a mixed solvent of 8 l of toluene and 500 ml of ethyl acetate. After washing the resultant solution once with a saturated aqueous solution of sodium bicarbonate, three times with water and then once with saturated saline, the solution was concentrated to about 500 ml under reduced pressure. The concentrate was cooled to room temperature and the resultant yel-

REFERENTIAL EXAMPLE 89

6,7-Dimethoxy-2-hydroxyquinazoline

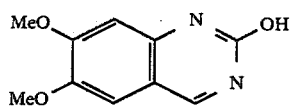

Dissolved in a mixed solvent of 30 ml of dichloromethane and 30 ml of methanol were 3.17 g of the 4,5-dimethoxy-2-nitrobenzaldehyde synthesized in Referential Example 88, followed by an addition of 0.16 g of 5% Pd-C. The resultant mixture was stirred for 4 hours in a hydrogen atmosphere. Pd-C was filtered off and the solvent was distilled off under reduced pressure. The residue was dissolved in 30 ml of acetic acid, followed by an addition of potassium cyanate. After reacting the contents overnight at room temperature, they were heated and reacted for further 1 hour under reflux. The solvent was distilled off under reduced pressure and the residue was purified by column chromatography (silica gel; eluent: 5:1 mixed solvent of dichlromethane and MeOH), thereby obtaining 1.51 g of the above-identified compound as colorless crystals (yield: 49%).

Melting point: 260°–263° C.

REFERENTIAL EXAMPLE 90

2-Hydroxyquinazoline

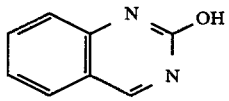

Following the procedure of Referential Example 89, the above-identified compound was obtained from o-nitrobenzaldehyde.

Melting point: 189° C.

REFERENTIAL EXAMPLE 91

2-Chloro-6,7-dimethoxyquinazoline

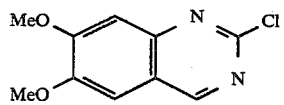

Phosphorus oxychloride (50 ml) was added to 5.0 g of the 6,7-dimethoxy-2-hydroxyquinazoline synthesized in Referential Example 89. They were heated and reacted for 8 hours under reflux. After allowing the reaction mixture to cool down, phosphorus oxychloride was distilled off under reduced pressure and the residue was dissolved in dichloromethane. After washing the dichloromethane solution once with a saturated aqueous solution of sodium bicarbonate, once with water and then once with saturated saline, the solution was dried with anhydrous sodium sulfate. The solvent was distilled under reduced pressure and the residue was purified by column chromatography (silica gel; eluent: 50:1 mixed solvent of dichloromethane and methanol), thereby obtaining 2.1 g of the intended product as crystals (yield: 38%).

Melting point: 237°–238° C.

REFERENTIAL EXAMPLE 92

2-Chloroquinazoline

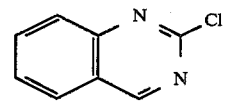

Following the procedure of Referential Example 91, the above-identified compound was obtaind from 2-hydroxyquinazoline.

$^1$H-NMR spectrum (CDCl$_3$ solution, δ ppm): 7.72 (1H, m), 7.96 (3H, m), 9.32 (1H, s).

EXAMPLE 95

6,7-Dimethoxy-2-(4-(5,6-dihydro-6-ethyl-5-oxopyrido[4,3-d]pyrimidine-2-yl)piperazino)quinazoline

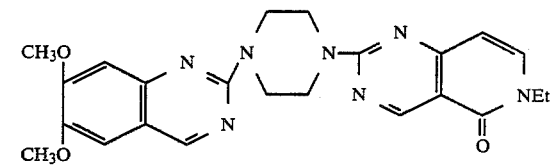

Tri-n-propylamine (0.43 g) was added to 0.67 g of the 2-chloro-6,7-dimethoxyquinazoline synthesized in Referential Example 91 and 0.78 g of the 6-ethyl-2-piperazinopyrido[4,3-d]pyrimidine-5(6H)-one synthesized in Referential Example 14. Using 5 g of isoamyl alcohol as a solvent, they were heated and reacted for 10 hours under reflux. The resultant crystals were collected by filtration and then washed first with ethyl acetate and then with hexane. They were dried to obtain 1.24 g of the above-identified compound as white crystals (yield: 92%).

Melting point: 259°–262° C.

$^1$H-NMR spectrum (CDCl$_3$ solution, δ ppm): 1.36 (3H, t, J=7 Hz), 3.96 (3H, s), 3.97 (2H, q, J=7 Hz), 4.02 (3H, s), 4.05 (8H, br.s), 6.32 (1H, d, J=7 Hz), 6.93 (1H, s), 6.98 (1H, s), 7.30 (1H, d, J=7 Hz), 8.82 (1H, s), 9.28 (1H, s).

EXAMPLE 96

2-(4-(5,6-Dihydro-6-ethyl-5-oxopyrido[4,3-d]pyrimidine-2-yl)piperazino)quinazoline

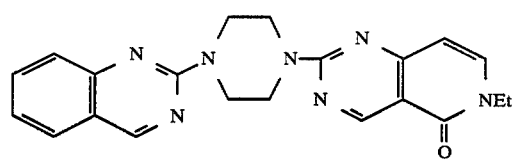

In a manner similar to that employed in Example 95, the above-identified compound was obtained from the 2-chloroquinazoline synthesized in Referential Example 95 and the 6-ethyl-2-piperazinopyrido[4,3-d]pyrimidine-5-(6H)-one synthesized in Referential Example 14 (yield: 30%).

Melting point: 222°–224° C.

$^1$H-NMR spectrum (CDCl$_3$ solution, δ ppm): 1.33 (3H, t, J=7 Hz), 3.92 (2H, q, J=7 Hz), 4.08 (8H, br.s), 6.30 (1H, d, J=7 Hz), 7.22 (1H, d, J=7 Hz), 7.24 (2H, m), 7.62 (1H, m), 9.0 (1H, s), 9.27 (1H, s).

Each of the following Examples, which are directed to preparations, makes use of one of the compounds described in Examples 1 to 96 or one of other pharmaceutical compounds embraced by the general formula [I] as an active component.

EXAMPLE 97

Tablets containing 0.2 mg of their respective active components were individually prepared in the following manner.

|  | per tablet |
| --- | --- |
| Active component | 0.2 mg |
| Starch | 54.8 mg |
| Microcrystalline cellulose | 35 mg |
| Polyvinylpyrrolidone (as 10% aqueous solution) | 4 mg |
| Calcium carboxymethylcellulose | 4.5 mg |
| Magnesium stearate | 0.5 mg |
| Talc | 1.0 mg |
| (Total) | 100 mg |

The active component, starch and microcrystalline were caused to pass through an 80-mesh sieve to mix them intimately. The thus-obtained powder was added with the polyvinylpyrrolidone solution, followed by granulation. The resultant granules were classified through an 18-mesh sieve. The thus-prepared granules were dried at 50°–60° C. and again classified through an 18-mesh sieve. The granules were then added with the calcium carboxymethylcellulose, magnesium stearate and talc which had in advance been classified through an 80-mesh sieve individually. After mixing them together, the resultant mixture was formed into tablets, each having a weight of 100 mg, by a tableting machine.

EXAMPLE 98

Tablets containing 1 mg of their respective active components were individually prepared in the following manner.

|  | per tablet |
| --- | --- |
| Active component | 1 mg |
| Starch | 60 mg |
| Microcrystalline cellulose | 35 mg |
| Light silicic anhydride | 3 mg |
| Magnesium stearate | 1 mg |
| (Total) | 100 mg |

The above components were caused to pass through an 80-mesh sieve, thereby mixing them intimately. The thus-obtained powder was compression-formed to prepare tablets each of which had a weight of 100 mg.

EXAMPLE 99

Capsules containing 0.5 mg of their respective active components were individually prepared in the following manner.

|  | per capsule |
| --- | --- |
| Active component | 0.5 mg |
| Dry starch | 50 mg |
| Microcrystalline cellulose | 47.5 mg |
| Magnesium stearate | 2 mg |
| (Total) | 100 mg |

The above components were mixed and then caused to pass through an 80-mesh sieve, thereby mixing them intimately. The thus-obtained powder was filled 100 mg by 100 mg in capsules.

EXAMPLE 100

Ten parts of ammonium polyacrylate were dissolved in 60 parts of water. On the side, 2 parts of glycerin diglycidylether were dissolved with heating in 10 parts of water. Still on the side, 10 parts of polyethylene glycol (Grade 400), 10 parts of water and 0.1 part of an active component were stirred to dissolve the active component. While stirring the aqueous solution of ammonium polyacrylate, the aqueous solution of glycerin diglycidylether and the aqueous solution, which contained polyethylene glycol and the active component, was added to and mixed with the aqueous solution of ammonium polyacrylate to prepare a drug-containing water-base gel formulation. The gel formulation was then coated on a flexible plastic film to give a coat weight of 0.05 mg per square centimeters in term of the active component. The surface was covered by a release paper web, followed by cutting same into cataplasms, each, of 35 cm$^2$ wide.

EXAMPLE 101

Prepared was a mixed water-base sol formulation of 100 parts of sodium polyacrylate, 100 parts of glycerin, 150 parts of water, 0.2 part of triepoxypropyl isocyanurate, 100 parts of ethanol, 25 parts of isopropyl myristate, 25 parts of propylene glycol and 1 part of an active component. The sol formulation was then coated on the surface of a nonwoven rayon fabric of a composite film, which was composed of the nonwoven rayon fabric and a polyethylene film, to 100 μm thick so that a drug-containing tacky mass layer was formed. The content of the releasing adjuvants (i.e., isopropyl myristate and propylene glycol) in the layer was about 20 wt.%. Thereafter, the tacky mass layer was crosslinked at 25° C. for 24 hours. A release film was applied on the surface of the tacky mass layer, followed by cutting same into cataplasms, each, of 35 cm$^2$ wide.

EXAMPLE 102

Mixed at 70° C. in a kneader was a composition which consisted of 110 parts of a styrene-isoprene-styrene block copolymer, 90 parts of a terpene resin, 60 parts of olive oil, 0.1 part of ethylene glycol diacrylate and 0.5 part of an active component.

From an extruder, the mixture was then extruded and coated at 60° C. onto one side of a polyvinyl chloride film of 100 μm thick to a thickness of 100 μm, thereby forming a drug-containing tacky mass layer. Thereafter, the tacky mass layer was exposed to ionizing radiation to give a dose of 10 Mrad. The thus-exposed layer was brought into a contiguous relation with a release film, followed by cutting same into desired sizes to form cataplasms.

[Effects of the Present Invention]

The present invention has made it clear through treating hypertension in mammals that as mentioned above, the compounds [I] of this invention have extremely strong and long-acting antihypertensive effects and some of the compounds reduce or substantially avoid orthostatic hypotension, which is an undesirable side effect accompanying short-term blood pressure drop, compared with the conventionally-known compounds. The antihypertensive effects of certain compounds of this invention as well as their antihypertensive effects along the passage of time, i.e., their antihypertensive patterns and long-acting properties were investigated on spontaneously hypertensive rats (SHRs). Investigation results are shown in Table 5. Many of the compounds of this invention showed stronger antihypertensive activity, weaker degrees of blood pressure drop upon an elapsed time of 1 hour after the administration of the drugs, and development of milder antihypertensive effects and longer-lasting patterns, all, compared with prazosin employed as Control. Furthermore, the toxicity levels of the compounds of this invention are generally weak. By way of example, their acute toxicity are shown in Table 6. As demonstrated herein, the compounds of this invention are generally believed to serve as drugs which have higher activity and lower toxicity, i.e., higher safety. Hereinafter, biological activities of certain compounds of this invention will be shown in Tests 1 and 2.

Test 1:

The antihypertensive effects of the certain compounds of this invention were studied in the following manner.

Among male, spontaneously hypertensive rats (SHRs) of 20 weeks of age or older and 350–430 g heavy all of which had developed hypertension, those having systolic blood pressures of 180 mmHg or higher were used in groups, each of which was constituted of 3–4 of the rats. Blood pressures were measured indirectly in terms of systolic blood pressures at tail arteries by a hemodynamometer (W+W electronic, BP-8005) under no anesthesia before administration of drugs and upon elapsed time of 1, 3, 6 and 24 hours after the administration. Besides, heart rates were also measured simultaneously. The compounds were each dissolved or suspended in a 0.5% methylcellulose solution and then administered orally. Results are shown in Table 5.

TABLE 5

| | Effects on Blood Pressures and Heart Rates of Spontaneously Hypertensive Rats | | | | |
|---|---|---|---|---|---|
| Compound* | Antihypertensive effects, change (%) in blood pressure | | | | Change (%)** |
| Example # | 1 hour later | 3 hours later | 6 hours later | 24 hours later | in heart rate |
| 1 | −10.7 | −17.3 | −23.0 | −8.2 | +4.1 |
| 2 | −9.0 | −23.9 | −38.8 | −16.4 | +18.4 |
| 3 | −2.5 | −8.0 | −15.1 | −5.0 | +7.1 |
| 4 | −4.4 | −22.1 | −26.5 | −16.7 | +5.7 |
| 5 | 0 | −6.3 | −13.2 | −6.3 | +2.6 |
| 6 | −1.5 | −13.8 | −16.7 | −9.9 | +5.1 |
| 7 | +1.5 | −4.4 | −9.3 | −2.9 | +2.8 |
| 8 | −0.5 | −9.5 | −11.4 | −4.0 | +5.2 |
| 9 | −1.5 | −8.1 | −9.6 | −5.1 | +4.3 |
| 10 | +1.5 | −14.4 | −11.9 | −5.0 | +5.2 |
| 11 | −0.5 | −16.6 | −17.1 | −6.8 | +5.7 |
| 12 | −11.0 | −14.3 | −19.0 | −6.7 | +7.0 |
| 13 | −1.0 | −3.9 | −10.6 | −3.9 | +7.4 |
| 14 | −1.9 | −4.8 | −13.9 | −11.0 | +7.3 |
| 15 | −2.9 | −7.7 | −12.0 | −7.7 | +3.7 |
| 16 | −2.0 | −8.9 | −15.3 | −8.9 | +7.5 |
| 17 | 0 | −20.2 | −27.9 | −12.0 | +10.8 |
| 18 | 0 | −3.9 | −9.8 | −3.9 | +11.1 |
| 19 | −2.4 | −10.1 | −11.1 | −2.9 | +2.9 |
| 20 | +1.5 | −12.5 | −12.0 | −2.0 | +5.7 |
| 21 | −17.2 | −23.2 | −23.6 | −3.4 | +7.4 |
| 22 | −1.5 | −10.1 | −17.1 | −4.0 | +17.7 |
| 23 | −11.7 | −21.9 | −27.0 | −2.6 | +23.1 |
| 24 | −7.2 | −24.8 | −28.6 | −8.7 | +12.0 |
| 25 | −4.3 | −23.9 | −35.4 | −6.7 | +12.9 |
| 26 | −8.8 | −15.2 | −21.6 | −4.9 | +9.8 |
| 27 | −5.4 | −17.6 | −21.0 | −2.4 | +8.3 |
| 28 | −17.2 | −15.3 | −31.6 | −3.3 | +11.7 |
| 29 | −5.2 | −23.0 | −35.2 | −13.1 | +10.1 |
| 30 | −7.4 | −24.7 | −32.1 | −8.8 | +11.7 |
| 31 | −2.8 | −8.5 | −17.8 | −3.8 | +14.5 |
| 32 | −20.2 | −30.5 | −35.2 | −16.4 | +11.0 |
| 33 | −20.4 | −27.0 | −32.1 | −9.7 | +17.5 |
| 34 | +0.5 | −9.1 | −13.9 | −7.2 | +2.3 |
| 35 | −0.5 | −8.7 | −16.3 | −15.9 | +9.1 |
| 36 | −14.6 | −16.5 | −15.0 | −2.4 | +9.5 |
| 37 | −4.7 | −16.4 | −21.1 | −8.5 | +5.8 |
| 38 | −26.6 | −24.1 | −27.6 | −7.9 | +7.9 |
| 39 | −4.4 | −12.7 | −7.3 | +1.5 | +2.2 |
| 40 | −1.4 | −15.9 | −18.4 | −8.2 | +5.8 |
| 41 | −11.2 | −19.5 | −25.9 | −3.9 | +9.2 |
| 42 | −16.5 | −19.5 | −24.0 | −7.5 | +5.2 |
| 43 | +4.5 | +0.5 | −6.5 | −9.5 | +5.7 |
| 44 | +9.1 | 0 | −4.0 | 0 | +7.9 |
| 45 | −1.5 | −2.5 | −8.0 | −5.5 | +4.2 |
| 46 | 0 | −11.9 | −17.5 | −5.7 | +7.4 |
| 47 | −3.5 | −9.0 | −12.5 | −2.5 | +6.3 |
| 48 | −4.5 | −9.0 | −15.0 | −4.0 | +6.9 |
| 49 | −4.5 | −10.6 | −13.1 | −7.5 | +6.3 |
| 50 | −1.5 | −8.7 | −14.6 | −6.3 | +2.9 |
| 51 | +8.6 | 0 | −4.1 | −2.5 | +3.0 |
| 52 | −8.0 | −13.0 | −19.5 | −3.0 | +3.6 |
| 53 | −27.9 | −31.3 | −36.1 | −12.0 | +25.7 |
| 54 | −4.3 | −11.4 | −16.7 | −4.8 | +5.2 |
| 55 | −6.5 | −21.9 | −29.9 | −7.5 | +7.0 |
| 56 | −21.4 | −22.4 | −22.9 | −4.5 | +13.5 |
| 57 | −10.4 | −18.9 | −27.9 | −9.0 | +4.3 |
| 58 | −7.4 | −17.6 | −22.5 | −9.8 | +9.8 |
| 59 | −10.1 | −23.9 | −30.6 | −12.4 | +5.7 |
| 60 | −1.6 | −5.2 | −8.8 | −1.0 | +6.0 |
| 61 | −2.4 | −22.0 | −28.2 | −12.0 | +12.4 |
| 62 | −1.4 | −24.0 | −31.3 | −21.2 | +7.6 |
| 63 | +3.1 | −4.7 | −9.0 | −6.6 | +6.8 |
| 64 | −1.4 | −9.6 | −13.9 | −1.9 | +9.9 |
| 65 | −4.9 | −18.4 | −21.4 | −6.3 | +8.9 |
| 66 | −18.0 | −23.7 | −28.9 | −16.0 | +3.8 |
| 67 | −21.4 | −28.6 | −38.4 | −16.7 | +7.4 |
| 68 | +1.4 | −19.6 | −28.2 | −11.5 | +5.2 |
| 69 | −12.9 | −22.7 | −24.7 | −4.6 | +7.4 |
| 70 | −7.8 | −17.5 | −23.3 | −4.4 | +13.7 |
| 71 | +0.5 | −13.4 | −19.1 | −9.6 | +15.9 |
| 72 | +2.9 | −2.0 | −2.5 | −2.9 | +8.6 |
| 73 | −0.5 | 0 | −7.0 | −8.0 | +4.3 |
| 74 | −0.5 | −14.1 | −23.3 | −12.1 | +9.0 |
| 75 | +12.2 | +0.5 | −7.8 | −3.9 | +8.2 |
| 76 | 0 | −3.8 | −7.2 | −9.6 | +2.9 |
| 77 | −31.0 | −32.9 | −36.2 | −13.8 | +25.1 |
| 78 | −23.4 | −33.7 | −50.2 | −18.5 | +23.7 |
| 79 | −27.9 | −33.7 | −45.2 | −21.2 | +22.3 |
| 80 | −13.9 | −26.0 | −33.2 | −10.1 | +12.3 |
| 81 | −0.5 | −7.3 | −12.1 | −8.7 | +3.8 |
| 82 | +0.5 | −6.9 | −8.8 | −6.4 | +5.8 |
| 83 | −3.9 | −4.4 | −5.3 | −0.5 | +5.6 |
| 84 | +0.5 | 0 | −1.5 | −0.5 | +2.2 |
| 85 | −1.5 | −7.3 | −12.2 | −3.9 | +3.5 |
| 86 | +0.5 | 0 | −6.4 | −0.5 | +7.1 |
| 87 | −6.9 | −15.2 | −21.6 | −2.5 | +17.7 |
| 88 | +0.5 | −4.4 | −6.9 | −2.0 | +5.8 |
| 89 | −2.4 | −13.3 | −13.8 | −2.9 | +5.8 |
| 90 | +2.3 | −6.8 | −15.5 | −2.7 | +8.7 |
| 91 | −4.0 | −8.0 | −12.9 | −2.5 | +8.2 |
| 92 | +1.4 | −3.3 | −9.4 | −6.1 | +8.5 |
| 93 | −4.5 | −9.0 | −10.5 | −5.0 | +8.0 |
| 94 | −0.5 | −12.7 | −22.1 | −5.4 | +5.4 |
| 95 | +2.5 | −2.9 | −6.4 | −3.9 | +5.8 |

TABLE 5-continued

| Compound* Example # | Effects on Blood Pressures and Heart Rates of Spontaneously Hypertensive Rats | | | | |
|---|---|---|---|---|---|
| | Antihypertensive effects, change (%) in blood pressure | | | | Change (%)** in heart rate |
| | 1 hour later | 3 hours later | 6 hours later | 24 hours later | |
| 96 | +3.0 | −2.5 | −8.0 | −6.5 | +2.9 |
| Prazosin | −23.6 | −25.1 | −24.6 | −5.0 | +8.0 |
| Terazosin | −22.4 | −25.9 | −23.4 | −5.4 | +7.2 |
| E-643*** | −4.8 | −12.0 | −13.5 | −6.7 | +8.8 |

*All administered orally at a dosage of 1 mg/Kg except for the compounds of Examples 65 and 92 (10 mg/Kg).
**Each percent change in heart rate is indicated by the corresponding maximum value.
***"E-643" is Eisai's Bunazosin.

Test 2

The acute toxicity of certain compounds of this invention were studied in the following manner.

Namely, male ddy-mice of 5 weeks of age and male Wister rats of 8 weeks of age were fasted for 18 hours and used in groups each of which was constituted of 4–5 of mice or rats. The compounds were each dissolved or suspended in a 0.5% methylcellulose solution and administered orally (P.O.). On the fourteenth day after the administration, their toxicity were judged. Results are shown in Table 6.

TABLE 6

| Compound Ex. No. | Acute Toxicity for Mouse and Rat | | | |
|---|---|---|---|---|
| | Mouse | | Rat | |
| | 1 g/Kg P.O. | 3 g/Kg P.O. | 1 g/Kg P.O. | 3 g/Kg P.O. |
| 1 | 0/5 | 0/5 | 0/5 | 0/5 |
| 2 | 0/5 | 0/5 | 0/5 | 0/5 |
| 4 | 0/5 | 0/5 | 0/5 | 0/5 |
| 17 | 0/5 | — | — | — |
| 21 | 0/4 | — | — | — |
| 23 | 0/5 | 0/5 | — | — |
| 24 | 0/5 | 0/5 | 0/5 | 0/5 |
| 25 | 0/5 | — | — | — |
| 28 | 0/5 | — | — | — |
| 29 | 0/5 | 0/5 | 0/5 | 0/4 |
| 30 | 0/5 | — | — | — |
| 32 | 0/5 | — | — | — |
| 39 | 0/5 | — | — | — |
| 62 | 0/5 | — | 0/5 | — |
| 66 | 0/5 | — | — | — |
| 70 | 0/4 | — | — | — |
| Prazosin | 0/5 | 0/5 | 0/5 | 0/3 |
| Terazosin | 0/5 | 1/5 | — | — |
| E-643* | 0/5 | — | 2/4 | — |

Note:
Each numeral set indicates the number of dead animals/the number of tested animals. Hyphens (—) indicate that no tests were effected.
*"E-643" is Eisai's Bunazosin.

As shown in Table 5, the compounds of this invention exhibited sufficient antihypertensive effects when orally administered at the dosage of 1 mg/Kg. The development of their effects were gradual and their maximum effects were observed 6 hours after their administration or even later. In addition, their effects were observed even 24 hours after their administration. They are thus long-acting compounds. With respect to heart rate, the degrees of its increases were slight. From these results, many of the compounds of this invention are expected to show higher antihypertensive effects, to develop lower degrees of heart rate increases and to be less susceptible of developing orthostatic hypotension due to short-term drop in blood pressure, all, compared with prazosin as Control. These features of the compounds of this invention are believed to make them excellent for the treatment of hypertension of mammals.

Moreover, their acute toxicity are weak as shown in Table 6. In view of their amounts to be required to develop their efficacy as drugs, they are considered to be highly safe compounds.

What is claimed is:

1. A quinazoline compound represented by the following formula I or a pharmacologically acceptable salt thereof:

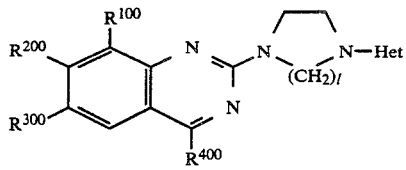

wherein $R^{100}$ means a hydrogen atom or methoxy group, $R^{200}$ and $R^{300}$ denote individually a hydrogen atom or lower alkoxy group, $R^{400}$ is a hydrogen atom or amino group, l stands for 2 or 3, and Het is represented by any one of the following formulae:

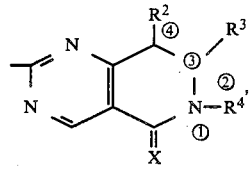

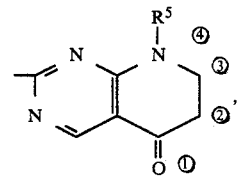

101
-continued

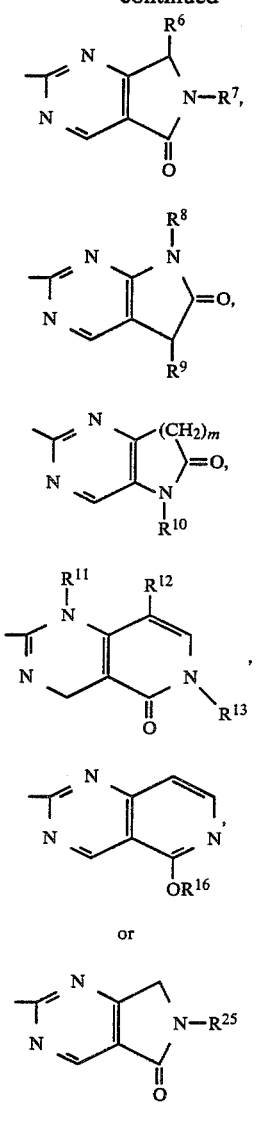

wherein,
in the formula II, either single or double bond is formed between the 3- and 4-positions, $R^2$ means a hydrogen atom or a lower alkyl, aralkyl in which alkyl is $C_1$-$C_4$ and aryl is phenyl, cyano or formyl group, $R^3$ denotes a hydrogen atom or a lower alkoxycarbonyl or phenyl group, $R^4$ is a hydrogen atom or a lower alkyl, lower cycloalkyl, hydroxy—substituted lower alkyl, lower alkoxy-substituted lower alkyl, lower alkoxy-substituted lower alkyl, phenyl or aralkyl in which alkyl is $C_1$-$C_4$ and aryl is phenyl and X stands for an oxygen or sulfur atom,
in the formula III, either single or double bond is formed between the 2- and 3-positions, and $R^5$ means a hydrogen atom or a lower alkyl group,
in the formula IV, $R^6$ and $R^7$ means individually a hydrogen atom or a lower alkyl group,
in the formula V, $R^8$ and $R^9$ mean individually a hydrogen atom or a lower alkyl group,
in the formula VI, m stands for 2 or 3, and $R^{10}$ means a hydrogen atom or a lower alkyl group,

102 in the formula VIII, $R^{11}$, $R^{12}$ and $R^{13}$ mean individually a hydrogen atom or a lower alkyl group,
in the formula X, $R^{16}$ means a lower alkyl group, and
in the formula XIV, $R^{25}$ means a $C_5$-$C_8$ alkyl, $C_4$-$C_7$ cycloalkyl, hydroxy-substituted lower alkyl group, lower alkoxy-substituted lower alkyl, di(lower alkylamino)-substituted lower alkyl or aralkyl in which alkyl is $C_1$-$C_4$ and aryl is phenyl.

2. A quinazoline compound represented by the following formula I' or a pharmacologically acceptable salt thereof:

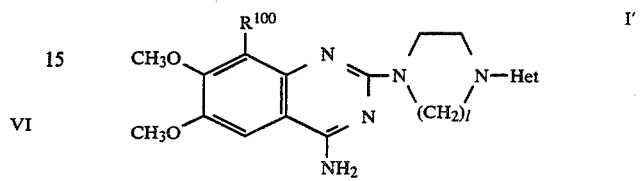

wherein $R^{100}$ means a hydrogen atom or a methoxy group, l stands for 2 or 3, and Het is represented by any one of the following formulae:

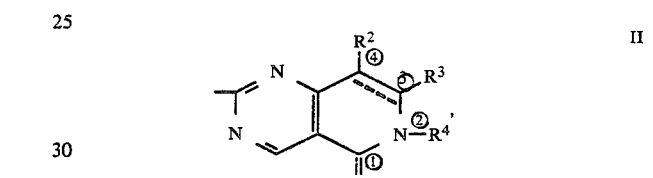

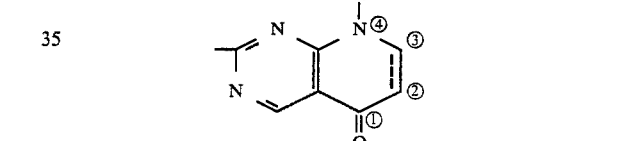

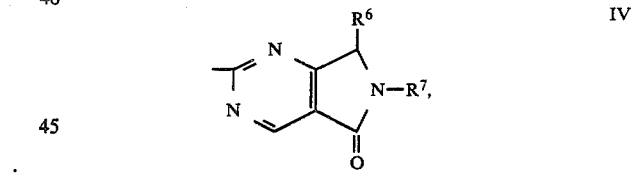

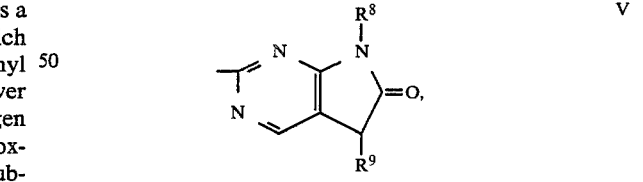

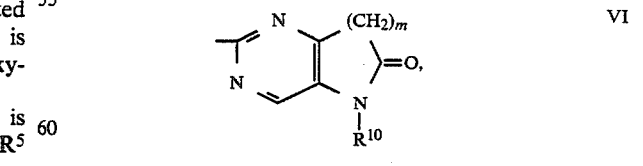

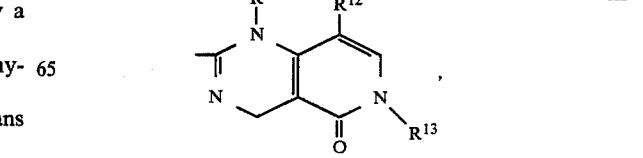

or

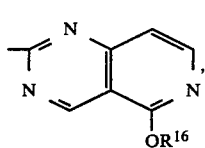

wherein,
- in the formula II, either single or double bond is formed between the 3- and 4-positions, $R^2$ means a hydrogen atom or a lower alkyl, aralkyl in which alkyl is $C_1$-$C_4$ and aryl is phenyl, cyano or formyl group, $R^3$ denotes a hydrogen atom or a lower alkoxycarbonyl or phenyl group, $R^4$ is a hydrogen atom or a lower alkyl, lower cycloalkyl, hydroxy-substituted lower alkyl, lower alkoxy-substituted lower alkyl, phenyl or aralkyl in which alkyl is $C_1$-$C_4$ and aryl is phenyl, and X stands for an oxygen or sulfur atom,
- in the formula III, either single or double bond is formed between the 2- and 3-positions, and $R^5$ means a hydrogen atom or a lower alkyl group,
- in the formula IV, $R^6$ and $R^7$ mean individually a hydrogen atom or a lower alkyl group,
- in the formula V, $R^8$ and $R^9$ mean individually a hydrogen atom or a lower alkyl group,
- in the formula VI, m stands for 2 or 3, and $R^{10}$ means a hydrogen atom or a lower alkyl group,
- in the formula VIII, $R^{11}$, $R^{12}$ and $R^{13}$ mean individually a hydrogen atom or a lower alkyl group, and
- in the formula X, $R^{16}$ means a lower alkyl group.

3. A quinazoline compound represented by the following formula I″ or a pharmacologically acceptable salt thereof:

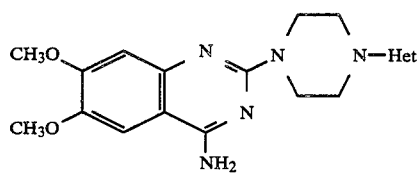

wherein Het is represented by the following formula:

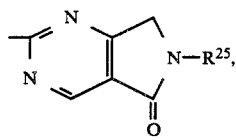

where $R^{25}$ means a $C_5$-$C_8$ alkyl, $C_4$-$C_7$ cycloalkyl, hydroxy-substituted lower alkyl group, lower alkoxy-substituted lower alkyl, di(lower alkylamino)-substituted lower alkyl or aralkyl in which alkyl is $C_1$-$C_4$, alkyl and aryl is phenyl.

4. A quinazoline conpound represented by the following formula I or a pharmacologically acceptable salt thereof:

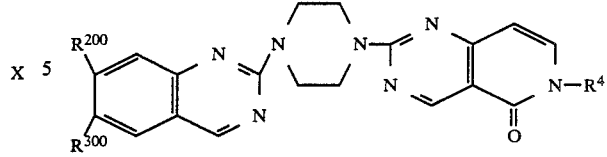

wherein $R^{200}$ and $R^{300}$ mean individually a hydrogen atom or lower alkoxy group, and $R^4$ denotes a lower alkyl group.

5. The compound as claimed in claim 2, wherein Het is represented by the formula II in which either single or double bond is formed between the 3- and 4-positions, $R^2$ means a hydrogen atom or a lower alkyl, aralkyl in which alkyl is $C_1$-$C_4$ and aryl is $C_6$-$C_8$, cyano or formyl group, $R^3$ denotes a hydrogen atom or a lower alkoxycarbonyl or phenyl group, $R^4$ is a hydrogen atom or a lower alkyl, lower cycloalkyl, hydroxy-substituted lower alkyl, lower alkoxy-substituted lower alkyl, phenyl or aralkyl in which alkyl is $C_1$-$C_4$ and aryl is phenyl and X stands for an oxygen or sulfur atom.

6. The compound as claimed in claim 2, wherein Het is represented by the formula III in which either single or double bond is formed between the 2- and 3-positions, and $R^5$ means a hydrogen atom or a lower alkyl group.

7. The compound as claimed in claim 2, wherein Het is represented by the formula IV in which $R^6$ and $R^7$ mean individually a hydrogen atom or a lower alkyl group.

8. The compound as claimed in claim 2, wherein Het is represented by the formula V in which $R^8$ and $R^9$ mean individually a hydrogen atom or a lower alkyl group.

9. The compound as claimed in claim 2, wherein Het is represented by the formula VI in which m stands for 2 or 3, and $R^{10}$ means a hydrogen atom or a lower alkyl group.

10. The compound as claimed in claim 2, wherein Het is represented by the formula VIII in which $R^{11}$, $R^{12}$ and $R^{13}$ mean individually a hydrogen atom or a lower alkyl group.

11. The compound as claimed in claim 2, wherein Het is represented by the formula X in which $R^{16}$ means a lower alkyl group.

12. The compound as claimed in claim 2, wherein Het is represented by the formula XIV in which $R^{25}$ means a $C_5$-$C_8$ alkyl, $C_4$-$C_7$ cycloalkyl, hydroxy-substituted lower alkyl group, lower alkoxy-substituted lower alkyl, di(lower alkylamino)-substituted lower alkyl or aralkyl in which alkyl is $C_1$-$C^4$ and aryl is phenyl.

13. An antihypertensive preparation comprising, as an active component, an effective amount of a quinazoline compound according to claim 1 and a pharmacologically acceptable carrier therefor.

14. An antihypertensive preparation comprising, as an active component, an effective amount of a quinazoline compound according to claim 2, and a pharmaceutically acceptable carrier therefor.

15. An antihypertensive preparation comprising, as an active component, an effective amount of a quinazoline compound according to claim 3 and a pharmacologically acceptable carrier therefor.

16. An antihypertensive preparation comprising, as an active component, a quinazoline compound represented by the following formula I or a pharmacologically acceptable salt thereof:

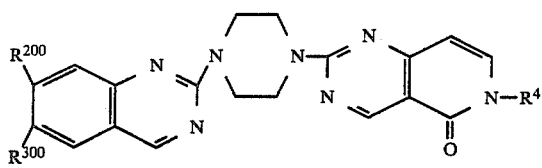

wherein $R^{200}$ and $R^{300}$ mean individually a hydrogen atom or lower alkoxy group, and $R^4$ denotes a lower alkyl group.

17. An antihypertensive preparation according to claim 13 also comprising a pharmaceutically acceptable carrier.

18. An antihypertensive preparation according to claim 13 also comprising a second antihypertensive component, a diuretic or a combination of another active antihypertensive component and a diuretic.

* * * * *

UNITED STATES PATENT AND TRADEMARK OFFICE
CERTIFICATE OF CORRECTION

PATENT NO. : 4,734,418

DATED : March 29, 1988

INVENTOR(S) : YOKOYAMA ET AL

It is certified that error appears in the above-identified patent and that said Letters Patent is hereby corrected as shown below: On the title page Assignee heading should read as follows:

--Mitsui Petrochemical Industries, Ltd., Tokyo, Japan and
  Mitsui Pharmaceutical Co., Ltd., Tokyo, Japan--

Signed and Sealed this

Eighth Day of November, 1988

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,734,418
DATED : March 29, 1988
INVENTOR(S) : Yokoyama et al

It is certified that error appears in the above-identified patent and that said Letters Patent is hereby corrected as shown below:

Please delete Formulas II and III in Claim 1 and insert the following therefor:

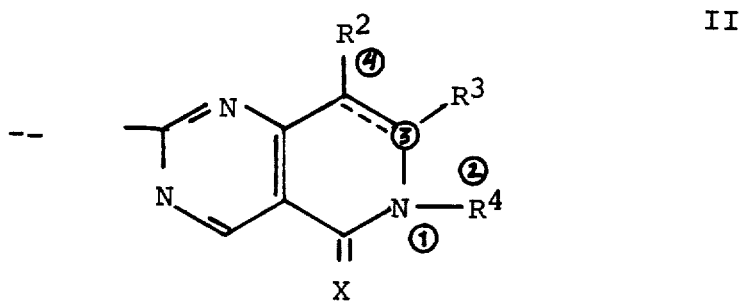

UNITED STATES PATENT AND TRADEMARK OFFICE
CERTIFICATE OF CORRECTION

PATENT NO. : 4,734,418

DATED : March 29, 1988

INVENTOR(S) : Yokoyama et al

It is certified that error appears in the above-identified patent and that said Letters Patent is hereby corrected as shown below:

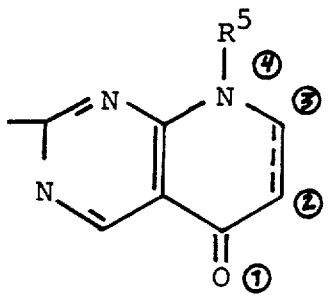

III

--

Signed and Sealed this

Twelfth Day of September, 1989

Attest:

DONALD J. QUIGG

Attesting Officer

Commissioner of Patents and Trademarks